(12) United States Patent
Fushimi et al.

(10) Patent No.: US 7,566,699 B2
(45) Date of Patent: Jul. 28, 2009

(54) FUSED HETEROCYCLIC DERIVATIVE, MEDICINAL COMPOSITION CONTAINING THE SAME, AND MEDICINAL USE THEREOF

(75) Inventors: Nobuhiko Fushimi, Hotaka-machi (JP); Shigeru Yonekubo, Hotaka-machi (JP); Hideyuki Muranaka, Hotaka-machi (JP); Hiroaki Shiohara, Hotaka-machi (JP); Hirotaka Teranishi, Hotaka-machi (JP); Kazuo Shimizu, Hotaka-machi (JP); Fumiaki Ito, Hotaka-machi (JP); Masayuki Isaji, Hotaka-machi (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 71 days.

(21) Appl. No.: 10/551,648

(22) PCT Filed: Mar. 24, 2004

(86) PCT No.: PCT/JP2004/004009

§ 371 (c)(1),
(2), (4) Date: Sep. 29, 2005

(87) PCT Pub. No.: WO2004/087727

PCT Pub. Date: Oct. 14, 2004

(65) Prior Publication Data

US 2006/0247179 A1  Nov. 2, 2006

(30) Foreign Application Priority Data

Mar. 31, 2003  (JP)  ............................. 2003-097152

(51) Int. Cl.
*A01N 43/04* (2006.01)
*A61K 31/70* (2006.01)
*C07H 15/00* (2006.01)
*C07H 17/00* (2006.01)

(52) U.S. Cl. ............................. 514/27; 514/23; 514/25; 514/35; 536/17.3; 536/17.4; 536/17.2; 536/4.1; 548/469

(58) Field of Classification Search .................. None
See application file for complete search history.

(56) References Cited

U.S. PATENT DOCUMENTS 6,515,117 B2    2/2003  Ellsworth et al.
6,683,056 B2 *  1/2004  Washburn et al. ............. 514/25
7,129,220 B2 * 10/2006  Beavers et al. ................. 514/27

FOREIGN PATENT DOCUMENTS

EP    1367060 A1    12/2003
JP    2003-511458 A  3/2003
WO   WO 01/27128 A1  4/2001
WO   WO 01/74844 A1  10/2001
WO   WO 02/64604 A1  8/2002
WO   WO 02/64606 A1  8/2002

* cited by examiner

*Primary Examiner*—Traviss C McIntosh, III
(74) *Attorney, Agent, or Firm*—Sughrue Mion, PLLC

(57) ABSTRACT

The present invention provides fused heterocyclic derivatives represented by the general formula:

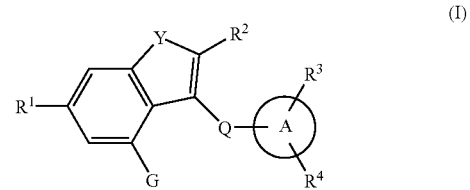

(I)

wherein $R^1$ represents H, halogen, OH, etc.; $R^2$ represents H, halogen or an alkyl group; $R^3$ and $R^4$ represent H, OH, halogen, etc.; Q represents alkylene, etc.; ring A represents aryl or heteroaryl; and G represents

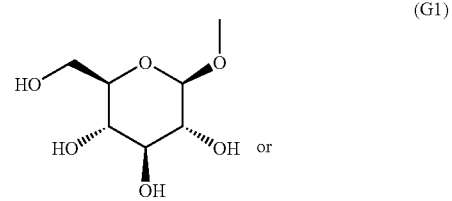

(G1)

or

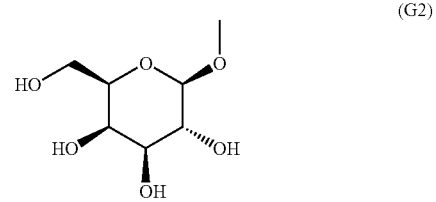

(G2)

or pharmaceutically acceptable salts thereof, or prodrugs thereof, which exhibit an excellent inhibitory activity in human SGLT and are useful as agents for the prevention or treatment of a disease associated with hyperglycemia such as diabetes, postprandial hyperglycemia, impaired glucose tolerance, diabetic complications or obesity, pharmaceutical compositions comprising the same, and pharmaceutical uses thereof.

15 Claims, No Drawings

FUSED HETEROCYCLIC DERIVATIVE, MEDICINAL COMPOSITION CONTAINING THE SAME, AND MEDICINAL USE THEREOF

TECHNICAL FIELD

The present invention relates to fused heterocyclic derivatives, pharmaceutically acceptable salts thereof or prodrugs thereof which are useful as medicaments, pharmaceutical compositions comprising the same and pharmaceutical uses thereof.

More particularly, the present invention relates to fused heterocyclic derivatives having an inhibitory activity in human SGLT, pharmaceutically acceptable salts thereof or prodrugs thereof which are useful as agents for the prevention or treatment of a disease associated with hyperglycemia such as diabetes, impaired glucose tolerance, diabetic complications or obesity, pharmaceutical compositions comprising the same and pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. In addition, it has been confirmed by large-scale clinical trial that it is necessary to practice a long-term strict control of blood sugar level so as to prevent patients with diabetes from occurring and advancing diabetic complications by receiving treatment (for example, see the following References 1 and 2). Furthermore, many epidemiologic studies on impaired glucose tolerance and macroangiopathy show that impaired glucose tolerance as the boundary type is also a risk factor in macroangiopathy as well as diabetes. Thus, needs to improve postprandial hyperglycemia have been focused (for example, see the following Reference 3).

In recent years, development of various antidiabetic agents has been progressing with the background of a rapid increase of patients with diabetes. For example, Antidiabetic agents such as biguanides, sulfonylureas, insulin sensitivity enhancers, α-glucosidase inhibitors and the like have been employed. However, biguanides and sulfonylureas show occasionally adverse effects such as lactic acidosis and hypoglycemia, respectively. Insulin sensitivity enhancers show occasionally adverse effects such as edema, and are concerned for advancing obesity. In addition, α-glucosidase inhibitors, which delay carbohydrate digestion and absorption at the small intestine, are used to improve postprandial hyperglycemia. It has been also reported that a carbose, one of α-glucosidase inhibitors, has an effect of preventing or delaying the incidence of diabetes by applying to patients with impaired glucose tolerance (for example, see the following Reference 4). However, since α-glucosidase inhibitors do not affect elevated glucose levels by ingesting a monosaccharide of glucose (for example, see the following Reference 5), with recently changing compositions of sugars in meals, a wider range of activities inhibiting carbohydrate absorption has been desired.

In recent years, research and development of new type antidiabetic agents have been progressing, which promote urinary glucose excretion and lower blood glucose level by preventing reabsorption of excess glucose at the kidney (for example, see the following Reference 6). In addition, it is reported that SGLT2 (sodium-dependent glucose transporter 2) is present in the S1 segment of the kidney's proximal tubule and participates mainly in reabsorption of glucose filtrated through glomerular (for example, see the following Reference 7). Accordingly, inhibiting a human SGLT2 activity prevents reabsorption of excess glucose at the kidney, subsequently promotes excreting excess glucose though the urine, and normalizes blood glucose level. In addition, since such agents for promoting the excretion of urinary glucose excrete excess glucose though the urine and consequently the glucose accumulation in the body is decreased, they are also expected to have a preventing or alleviating effect on obesity and a diuretic effect. Furthermore, the agents are considered to be useful for various related diseases which occur accompanying the progress of diabetes or obesity due to hyperglycemia.

Furthermore, it has been known that SGLT1, sodium-dependent glucose transporter 1, exists in the small intestine which controls carbohydrate absorption. It has been also reported that insufficiency of glucose and galactose absorption arises in patients with dysfunction due to congenital abnormalities of human SGLT1 (for example, see the following References 8-10). In addition, it has been confirmed that SGLT1 is involved in glucose and galactose absorption (for example, see the following References 11 and 12). Furthermore, it is confirmed that mRNA and protein of SGLT1 increase and absorption of glucoses are accelerated in OLETF rats and rats with streptozotocin-induced diabetic symptoms (for example, see the following References 13 and 14). Generally in patients with diabetes, carbohydrate digestion and absorption are increased. For example, it is confirmed that mRNA and protein of SGLT1 are highly increased in the human small intestine (for example, see the following Reference 15). Therefore, blocking a human SGLT1 activity inhibits absorption of carbohydrates such as glucose at the small intestine, subsequently can prevent increase of blood sugar level. Especially, it is considered that delaying glucose absorption based on the above mentioned mechanism is effective to normalize postprandial hyperglycemia.

Therefore, fast development of antidiabetic agents with novel action mechanism, which have an inhibitory activity in human SGLT, has been desired to improve or solve the above-mentioned problems.

Fused heterocyclic derivatives provided in the present invention are entirely novel compounds. It has not ever been reported that these fused heterocyclic derivatives have an inhibitory activities in SGLT1 and/or SGLT2 and inhibit absorption of glucose and galactose at the small intestine, or are useful as agents to inhibit reabsorption of excess glucose at the kidney.

Reference 1: The Diabetes Control and Complications Trial Research Group, N. Engl. J. Med., 1993.9, Vol. 329, No. 14, pp. 977-986;

Reference 2: UK Prospective Diabetes Study Group, Lancet, 1998.9, Vol. 352, No. 9131, pp. 837-853;

Reference 3: Makoto TOMINAGA, Endocrinology & Diabetology, 2001.11, Vol. 13, No. 5, pp. 534-542;

Reference 4: Jean-Louis Chiasson and 5 persons, Lancet, 2002.6, Vol. 359, No. 9323, pp. 2072-2077;

Reference 5: Hiroyuki ODAKA and 3 persons, Journal of Japanese Society of Nutrition and Food Science, 1992, Vol. 45, p. 27;

Reference 6: Luciano Rossetti and 4 persons, J. Clin. Invest., 1987.5, Vol. 79, pp. 1510-1515;

Reference 7: Yoshikatsu Kanai and 4 persons, J. Clin. Invest., 1994.1, Vol. 93, pp. 397-404;

Reference 8: Tadao BABA and 1 person, Supplementary volume of Nippon Rinsho, Ryoikibetsu Shokogun, 1998, No. 19, pp. 552-554;

Reference 9: Michihiro KASAHARA and 2 persons, Saishin Igaku, 1996.1, Vol. 51, No. 1, pp. 84-90;

Reference 10: Tomofusa TSUCHIYA and 1 person, Nippon Rinsho, 1997.8, Vol. 55, No. 8, pp. 2131-2139;

Reference 11: Yoshikatsu KANAI, Kidney and Dialysis, 1998.12, Vol. 45, extra edition, pp. 232-237;

Reference 12: E. Turk and 4 persons, Nature, 1991.3, Vol. 350, pp. 354-356;

Reference 13: Y. Fujita and 5 persons, Diabetologia, 1998, Vol. 41, pp. 1459-1466;

Reference 14: J. Dyer and 5 persons, Biochemical Society Transactions, 1997, Vol. 25, p. 479S;

Reference 15: J. Dyer and 4 persons, American Journal of Physiology, 2002.2, Vol. 282, No. 2, pp. G241-G248

DISCLOSURE OF THE INVENTION

The present inventors have studied earnestly to find compounds having an inhibitory activity in human SGLT. As a result, it was found that certain fused heterocyclic derivatives represented by the following general formula (I) show an inhibitory activity in human SGLT1 and/or SGLT2 and are excellent agents having inhibitory activity in increase of blood glucose level or lowering blood glucose level as shown below, thereby forming the basis of the present invention.

The present invention is to provide novel compounds which show an inhibitory activity in human SGLT, pharmaceutical compositions comprising the same and pharmaceutical uses thereof.

This is, the present invention relates to

[1] a fused heterocyclic derivative represented by the following general formula (I):

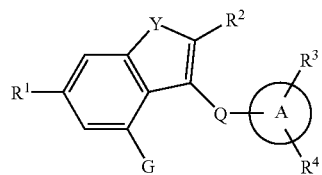

wherein $R^1$ represents a hydrogen atom, a halogen atom, a hydroxy group, an amino group, a mono or di($C_{1-6}$ alkyl)amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a hydroxy($C_{1-6}$ alkoxy) group, a mono or di[hydroxy($C_{1-6}$ alkyl)]amino group, a carboxy group, a $C_{2-7}$ alkoxycarbonyl group, a carbamoyl group or a carbamoyl($C_{1-6}$ alkyl) group;

$R^2$ represents a hydrogen atom, a halogen atom or a $C_{1-6}$ alkyl group;

$R^3$ and $R^4$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group, a hydroxy($C_{1-6}$ alkylthio) group, a carboxy group, a carboxy($C_{1-6}$ alkyl) group, a carboxy($C_{2-6}$ alkenyl) group, a carboxy($C_{1-6}$ alkoxy) group, a carboxy($C_{1-6}$ alkylthio) group, a $C_{2-7}$ alkoxycarbonyl group, a $C_{2-7}$ alkoxycarbonyl-substituted ($C_{1-6}$ alkyl) group, a $C_{2-7}$ alkoxycarbonyl-substituted ($C_{2-6}$ alkenyl) group, a $C_{2-7}$ alkoxycarbonyl-substituted ($C_{1-6}$ alkoxy) group, a $C_{2-7}$ alkoxycarbonyl-substituted ($C_{1-6}$ alkylthio) group, a $C_{1-6}$ alkylsulfinyl group, a $C_{1-6}$ alkylsulfonyl group, —U—V—W—N($R^5$)-Z or any of the following substitutes (i) to (xxviii) which may have 1 to 3 substituents selected from the following substituent group α on the ring;

(i) a $C_{6-10}$ aryl group, (ii) $C_{6-10}$ aryl-O—, (iii) $C_{6-10}$ aryl-S—, (iv) a $C_{6-10}$ aryl-substituted ($C_{1-6}$ alkyl) group, (v) a $C_{6-10}$ aryl-substituted ($C_{1-6}$ alkoxy) group, (vi) a $C_{6-10}$ aryl-substituted ($C_{1-6}$ alkylthio) group, (vii) a heteroaryl group, (viii) heteroaryl-O—, (ix) heteroaryl-S—, (x) a heteroaryl ($C_{1-6}$ alkyl) group, (xi) a heteroaryl($C_{1-6}$ alkoxy) group, (xii) a heteroaryl($C_{1-6}$ alkylthio) group, (xiii) a $C_{3-7}$ cycloalkyl group, (xiv) $C_{3-7}$ cycloalkyl-O—, (xv) $C_{3-7}$ cycloalkyl-S—, (xvi) a $C_{3-7}$ cycloalkyl-substituted ($C_{1-6}$ alkyl) group, (xvii) a $C_{3-7}$ cycloalkyl-substituted ($C_{1-6}$ alkoxy) group, (xviii) a $C_{3-7}$ cycloalkyl-substituted ($C_{1-6}$ alkylthio) group, (xix) a heterocycloalkyl group, (xx) heterocycloalkyl-O—, (xxi) heterocycloalkyl-S—, (xxii) a heterocycloalkyl($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group or (xxvii) an aromatic cyclic amino($C_{1-6}$ alkoxy) group, (xxviii) an aromatic cyclic amino($C_{1-6}$ alkylthio) group, U represents —O—, —S— or a single bond and with the proviso that at least one of V and W is not a single bond, when U is —O— or —S—);

V represents a $C_{1-6}$ alkylene group which may have a hydroxy group, a $C_{2-6}$ alkenylene group or a single bond;

W represents —CO—, —SO$_2$—, —C(=NH)— or a single bond;

Z represents a hydrogen atom, a $C_{2-7}$ alkoxycarbonyl group, a $C_{6-10}$ aryl-substituted ($C_{2-7}$ alkoxycarbonyl) group, a formyl group, —$R^A$, —COR$^B$, —SO$_2$R$^B$, —CON(R$^C$)R$^D$, —CSN(R$^C$)R$^D$, —SO$_2$NHR$^A$ or —C(=NR$^E$)N(R$^F$)R$^G$;

$R^5$, $R^A$, $R^C$ and $R^D$ independently represent a hydrogen atom, a $C_{1-6}$ alkyl group which may have 1 to 5 substituents selected from the following substituent group β or any of the following substitutes (xxix) to (xxxii) which may have 1 to 3 substituents selected from the following substituent group α;

(xxix) a $C_{6-10}$ aryl group, (xxx) a heteroaryl group, (xxxi) a $C_{3-7}$ cycloalkyl group or (xxxii) a heterocycloalkyl group or both of Z and $R^5$ bind together with the neighboring nitrogen atom to form an aliphatic cyclic amino group which may have 1 to 3 substituents selected from the following substituent group α;

or both of $R^C$ and $R^D$ bind together with the neighboring nitrogen atom to form an aliphatic cyclic amino group which may have 1 to 3 substituents selected from the following substituent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have 1 to 5 substituents selected from the following substituent group β or any of the following substitutes (xxxiii) to (xxxvi) which may have 1 to 3 substituents selected from the following substituent group α;

(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl-substituted ($C_{2-7}$ alkoxycarbonyl) group, a nitro group, a $C_{1-6}$ alkylsulfonyl group, a sulfamoyl group, a carbamimidoyl group or a $C_{1-6}$ alkyl group which may have 1 to 5 substituents selected from the following substituent group β;

or both of $R^E$ and $R^F$ bind together to form an ethylene group;

or both of $R^F$ and $R^G$ bind together with the neighboring nitrogen atom to form an aliphatic cyclic amino group which may have a substituent selected from the following substituent group α;

Y represents —O—, —S—, or —NH— which may be substituted by a $C_{1-6}$ alkyl group or a halo($C_{1-6}$ alkyl) group;

Q represents —$C_{1-6}$ alkylene-, —$C_{2-6}$ alkenylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene- or —$C_{1-6}$ alkylene-S—$C_{1-6}$ alkylene-;

ring A represents a $C_{6-10}$ aryl group or a heteroaryl group;

G represents a group represented by the formula:

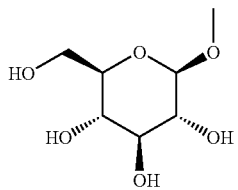

(G1)

or a formula:

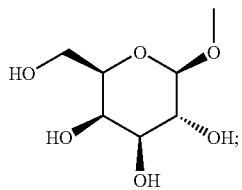

(G2)

[Substituent Group α]

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl-substituted ($C_{1-6}$ alkyl) group, a hydroxy ($C_{1-6}$ alkoxy) group, an amino($C_{1-6}$ alkyl) group, an amino ($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino-substituted ($C_{1-6}$ alkyl) group, a carboxy group, a $C_{2-7}$ alkoxycarbonyl group, a sulfamoyl group and —CON($R^H$)$R^I$

[Substituent Group β]

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$alkylthio) group, a mono or di($C_{1-6}$alkyl)amino group, a mono or di[hydroxy($C_{1-6}$ alkyl)] amino group, an ureido group, a sulfamide group, a mono or di($C_{1-6}$ alkyl) ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group, —CON($R^H$)$R^I$, and any of the following substitutes (xxxvii) to (xxxxviii) which may have 1 to 3 substituents selected from the above substituent group α on the ring;

(xxxvii) a $C_{6-10}$ aryl group, (xxxviii) $C_{6-10}$ aryl-O—, (xxxix) a $C_{6-10}$ aryl-substituted ($C_{1-6}$ alkoxy) group, (xxxx) a $C_{6-10}$ aryl-substituted ($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloalkyl-O—, (xxxxv) a heterocycloalkyl group, (xxxxvi) heterocycloalkyl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have 1 to 3 substituents selected from the following substituent group γ;

or both of $R^H$ and $R^I$ bind together with the neighboring nitrogen atom to form an aliphatic cyclic amino group which may have 1 to 3 substituents selected from the following substituent group δ;

[Substituent Group γ]

a halogen atom, a hydroxy group, an amino group, a $C_{1-6}$ alkoxy group, a halo($C_{1-6}$ alkoxy) group, a hydroxy($C_{1-6}$ alkoxy) group, an amino($C_{1-6}$ alkoxy) group, a mono or di($C_{1-6}$ alkyl)amino group, a mono or di[hydroxy($C_{1-6}$ alkyl)] amino group, an ureido group, a sulfamide group, a mono or di($C_{1-6}$ alkyl) ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group and —CON($R^J$)$R^K$

[Substituent Group δ]

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl-substituted ($C_{1-6}$ alkyl) group, a hydroxy ($C_{1-6}$ alkoxy) group, an amino($C_{1-6}$ alkyl) group, an amino ($C_{1-6}$alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino-substituted ($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di($C_{1-6}$ alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl)amino group, a $C_{1-6}$ alkyl group, a hydroxy($C_{1-6}$ alkyl) group, a $C_{2-7}$ alkoxycarbonyl group, a $C_{2-7}$ alkoxycarbonyl-substituted ($C_{1-6}$ alkyl) group and a carbamoyl group, or a pharmaceutically acceptable salt thereof, or a prodrug thereof;

[2] a fused heterocyclic derivative as described in the above [1], wherein $R^2$ represents a hydrogen atom; Y represents —O—, —S— or —NH—; Q represents an ethylene group, or a pharmaceutically acceptable salt thereof, or a prodrug thereof;

[3] a fused heterocyclic derivative as described in the above [1] or [2], wherein the ring A represents a group derived from a benzene ring, a pyridine ring, a pyrimidine ring, a pyrazine ring or a pyridazine ring, or a pharmaceutically acceptable salt thereof, or a prodrug thereof;

[4] a fused heterocyclic derivative as described in the above [3], wherein the ring A represents a phenyl group, or a pharmaceutically acceptable salt thereof, or a prodrug thereof;

[5] a fused heterocyclic derivative as described in the above [3], wherein the ring A represents a pyridyl group, or a pharmaceutically acceptable salt thereof, or a prodrug thereof;

[6] a pharmaceutical composition comprising as an active ingredient a fused heterocyclic derivative as described in any one of the above [1]-[5], or a pharmaceutically acceptable salt thereof, or a prodrug thereof;

[7] a human SGLT inhibitor comprising as an active ingredient a fused heterocyclic derivative as described in any one of the above [1]-[5], or a pharmaceutically acceptable salt thereof, or a prodrug thereof;

[8] a human SGLT1 and/or SGLT2 inhibitor comprising as an active ingredient a fused heterocyclic derivative as described in any one of the above [1]-[5], or a pharmaceutically acceptable salt thereof, or a prodrug thereof;

[9] a human SGLT inhibitor as described in the above [7] or [8], which is an agent for the inhibition of postprandial hyperglycemia;

[10] a human SGLT inhibitor as described in the above [7] or [8], which is an agent for the prevention or treatment of a disease associated with hyperglycemia;

[11] a human SGLT inhibitor as described in the above [10], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[12] a human SGLT inhibitor as described in the above [7] or [8], which is an agent for the inhibition of advancing impaired glucose tolerance into diabetes in a subject;

[13] a pharmaceutical composition as described in the above [6], wherein the dosage form is sustained release formulation;

[14] a human SGLT inhibitor as described in any one of the above [7]-[12], wherein the dosage form is sustained release formulation;

[15] a method for the inhibition of postprandial hyperglycemia, which comprises administering an effective amount of a fused heterocyclic derivative as described in any one of the above [1]-[5], or a pharmaceutically acceptable salt thereof, or a prodrug thereof;

[16] a method for the prevention or treatment of a disease associated with hyperglycemia, which comprises administering an effective amount of a fused heterocyclic derivative as described in any one of the above [1]-[5], or a pharmaceutically acceptable salt thereof, or a prodrug thereof;

[17] a method for the prevention or treatment as described in the above [16], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[18] a method for the inhibition of advancing impaired glucose tolerance into diabetes in a subject, which comprises administering an effective amount of a fused heterocyclic derivative as described in any one of the above [1]-[5], or a pharmaceutically acceptable salt thereof, or a prodrug thereof;

[19] a use of a fused heterocyclic derivative as described in any one of the above [1]-[5], or a pharmaceutically acceptable salt thereof, or a prodrug thereof for the manufacture of a pharmaceutical composition for the inhibition of postprandial hyperglycemia;

[20] a use of a fused heterocyclic derivative as described in any one of the above [1]-[5], or a pharmaceutically acceptable salt thereof, or a prodrug thereof for the manufacture of a pharmaceutical composition for the prevention or treatment of a disease associated with hyperglycemia;

[21] a use as described in the above [20], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[22] a use of a fused heterocyclic derivative as described in any one of the above [1]-51, or a pharmaceutically acceptable salt thereof, or a prodrug thereof for the manufacture of a pharmaceutical composition for the inhibition of advancing impaired glucose tolerance into diabetes in a subject;

[23] a pharmaceutical composition as described in the above [6] which comprises combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile-acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[24] a human SGLT inhibitor as described in any one of the above [7]-[12] which comprises combination with at least one member selected from the group of agents as described in the above [23];

[25] a method as described in any one of the above [15]-[18] which comprises combination with at least one member selected from the group of agents as described in the above [23];

[26] a use as described in any one of the above [19]-[22] which comprises combination with at least one member selected from the group of agents as described in the above [23]; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{1-6}$ alkylene group" or "—$C_{1-6}$ alkylene-" means a straight-chained or branched alkylene group having 1 to 6 carbon atoms such as a methylene group, an ethylene group, a trimethylene group, a tetramethylene group, a propylene group, a 1,1-dimethylethylene group or the like; and the term "$C_{1-4}$ alkylene group" means a straight-chained or branched alkylene group having 1 to 4 carbon atoms such as a methylene group, an ethylene group, a trimethylene group, a tetramethylene group, a propylene group, a 1,1-dimethylethylene group or the like. The term "hydroxy($C_{1-6}$ alkyl) group" means the above $C_{1-6}$ alkyl group substituted by a hydroxy group; the term "amino($C_{1-6}$ alkyl) group" means the above $C_{1-6}$ alkyl group substituted by an amino group such as an aminomethyl group, a 2-aminoethyl group or the like; the term "carbamoyl($C_{1-6}$ alkyl) group" means the above $C_{1-6}$ alkyl group substituted by a carbamoyl group; the term "carboxy($C_{1-6}$ alkyl) group" means the above $C_{1-6}$ alkyl group substituted by a carboxy group.

The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "hydroxy($C_{1-6}$ alkoxy) group" means the above $C_{1-6}$ alkoxy group substituted by a hydroxy group; the term "carboxy($C_{1-6}$ alkoxy) group" means the above $C_{1-6}$ alkoxy group substituted by a carboxy group; and the term "amino($C_{1-6}$ alkoxy) group" means the above $C_{1-6}$ alkoxy group substituted by an amino group. The term "$C_{1-6}$alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like; the term "hydroxy($C_{1-6}$ alkylthio) group" means the above $C_{1-6}$ alkylthio group substituted by a hydroxy group; the term "carboxy($C_{1-6}$alkylthio) group" means the above $C_{1-6}$ alkylthio group substituted by a carboxy group; the term "amino($C_{1-6}$alkylthio) group" means the above $C_{1-6}$ alkylthio group substituted by an amino group.

The term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkenylene group" or "—$C_{2-6}$ alkenylene-" means a straight-chained or branched alkenylene group having 2 to 6 carbon atoms such as a vinylene group, a propenylene group or the like; the term "$C_{2-4}$ alkenylene group" means a straight-chained or branched alkenylene group having 2 to 4 carbon atoms such as a vinylene group, a propenylene group or the like; the term "hydroxy($C_{2-6}$ alkenyl) group" means the above $C_{2-6}$ alkenyl group substituted by a hydroxy group; the term "carboxy($C_{2-6}$ alkenyl) group" means the above $C_{2-6}$ alkenyl group substituted by a carboxy group; the term "$C_{2-6}$ alkenyloxy group" means a straight-chained or branched alkenyloxy group having 2 to 6 carbon atoms such as a vinyloxy group, an allyloxy group, a 1-propenyloxy group, an isopropenyloxy group, a 1-butenyloxy group, a 2-butenyloxy group, a 2-methylallyloxy group or the like; the term "$C_{2-6}$ alkenylthio group" means a straight-chained or branched alkenylthio group having 2 to 6 carbon atoms such as a vinylthio group, an allylthio group, a 1-propenylthio group, an isopropenylthio group, a 1-butenylthio group, a 2-butenylthio group, a 2-methylallylthio group or the like; and the term "$C_{2-6}$ alkynyl group" means a straight-chained or branched alkynyl group having 2 to 6 carbon atoms such as an ethynyl group, a 2-propynyl group or the like.

The term "mono or di($C_{1-6}$ alkyl)amino group" means an amino group mono-substituted by the above $C_{1-6}$ alkyl group or di-substituted by the same or different $C_{1-6}$ alkyl groups as defined above; the term "mono or di[hydroxy($C_{1-6}$ alkyl)] amino group" means an amino groin mono-substituted by the above hydroxy($C_{1-6}$ alkyl) group or di-substituted by any of the above hydroxy($C_{1-6}$ alkyl) groups; the term "mono or di($C_{1-6}$ alkyl)ureido group" means an ureido group mono-substituted by the above $C_{1-6}$ alkyl group or di-substituted by any of the above $C_{1-6}$ alkyl groups; the term "mono or di[hydroxy($C_{1-6}$ alkyl)]ureido group" means an ureido group mono-substituted by the above hydroxy($C_{1-6}$ alkyl) group or di-substituted by any of the above hydroxy($C_{1-6}$alkyl) groups; the term "mono or di($C_{1-6}$ alkyl)sulfamide group" means a sulfamide group mono-substituted by the above $C_{1-6}$ alkyl group or di-substituted by any of the above $C_{1-6}$ alkyl groups as defined above; the term "mono or di[hydroxy($C_{1-6}$ alkyl)]sulfamide group" means a sulfamide group mono-substituted by the above hydroxy($C_{1-6}$ alkyl) group or di-substituted by any of the above hydroxy($C_{1-6}$ alkyl) groups as defined above; the term "$C_{2-7}$ acyl group" means a straight-chained or branched acyl group having 2 to 7 carbon atoms, such as an acetyl group, a propionyl group, a butyryl group, an isobutyryl group, a valeryl group, a pivaloyl group, a hexanoyl group or the like; the term "$C_{2-7}$ acylamino group" means an amino group substituted by the above $C_{2-7}$ acyl group; and the term "amino($C_{2-7}$ acylamino) group" means the above $C_{2-7}$ acylamino group substituted by an amino group, such as a 2-aminoacetylamino group, a 3-aminopropionylamino group or the like. The term "$C_{1-6}$ alkylsulfinyl group" means a straight-chained or branched alkylsulfinyl group having 1 to 6 carbon atoms, such as a methylsulfinyl group, an ethylsulfinyl group or the like; the term "$C_{1-6}$ alkylsulfonyl group" means a straight-chained or branched alkylsulfonyl group having 1 to 6 carbon atoms, such as a methanesulfonyl group, an ethanesulfonyl group or the like; the term "$C_{1-6}$ alkylsulfonylamino group" means an amino group substituted by the above $C_{1-6}$ alkylsulfonyl group; the term "carbamoyl($C_{1-6}$ alkylsulfonylamino) group" means the above $C_{1-6}$ alkylsulfonylamino group substituted by a carbamoyl group, such as a carbamoylmethanesulfonylamino group or the like; and the term "$C_{1-6}$ alkylsulfonylamino-substituted ($C_{1-6}$ alkyl) group" means the above $C_{1-6}$ alkyl group substituted by the above $C_{1-6}$ alkylsulfonylamino group.

The term "halogen atom" means a fluorine atom, a chlorine atom, a bromine atom or an iodine atom; the term "halo($C_{1-6}$ alkyl) group" means the above $C_{1-6}$ alkyl group substituted by any 1 to 3 halogen atoms as defined above; the term "halo ($C_{1-6}$ alkoxy) group" means the above $C_{1-6}$ alkoxy group substituted by any 1 to 3 halogen atoms as defined above; and the term "halo($C_{1-6}$ alkylthio) group" means the above $C_{1-6}$ alkylthio group substituted by any 1 to 3 halogen atoms as defined above. The term "$C_{2-7}$ alkoxycarbonyl group" means a straight-chained or branched alkoxycarbonyl group having 2 to 7 carbon atoms, such as a methoxycarbonyl group, an ethoxycarbonyl group, a propoxycarbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; the term "$C_{2-7}$ alkoxycarbonyl-substituted ($C_{1-6}$ alkyl) group" means the above $C_{1-6}$ alkyl group substituted by the above $C_{2-7}$ alkoxycarbonyl group; the term "$C_{2-7}$ alkoxycarbonyl-substituted ($C_{1-6}$ alkoxy) group" means the above $C_{1-6}$ alkoxy group substituted by the above $C_{2-7}$ alkoxycarbonyl group; the term "$C_{2-7}$ alkoxycarbonyl-substituted ($C_{1-6}$ alkylthio) group" means the above $C_{1-6}$ alkylthio group substituted by the above $C_{2-7}$ alkoxycarbonyl group; and the term "$C_{2-7}$ alkoxycarbonyl-substituted ($C_{2-6}$ alkenyl) group" means the above $C_{2-6}$ alkenyl group substituted by the above $C_{2-7}$ alkoxycarbonyl group.

The term "$C_{3-7}$ cycloalkyl group" or "$C_{3-7}$ cycloalkyl-" means a cyclopropyl group, a cyclobutyl group, a cyclopentyl group, a cyclohexyl group or a cycloheptyl group; the term "$C_{3-7}$ cycloalkyl-substituted ($C_{1-6}$ alkyl) group" means the above $C_{1-6}$ alkyl group substituted by the above $C_{3-7}$ cycloalkyl group; the term "$C_{3-7}$ cycloalkyl-substituted ($C_{1-6}$ alkoxy) group" means the above $C_{1-6}$ alkoxy group substituted by the above $C_{3-7}$ cycloalkyl group; and the term "$C_{3-7}$cycloalkyl-substituted ($C_{1-6}$ alkylthio) group" means the above $C_{1-6}$ alkylthio group substituted by the above $C_{3-7}$ cycloalkyl group. The term "heterocycloalkyl group" or "heterocycloalkyl-" means a 3 to 7-membered aliphatic heterocyclic group containing any 1 or 2 hetero atoms other than the binding position selected from an oxygen atom, a sulfur atom and a nitrogen atom in the ring, which is derived from morpholine, thiomorpholine, tetrahydrofuran, tetrahydropyran, aziridine, azetidine, pyrrolidine, imidazolidine, oxazoline, piperidine, piperazine, pyrazolidine, pyrroline, imidazoline or the like, or a 5 or 6-membered aliphatic heterocyclic group fused with a 6-membered aliphatic heterocycle containing any 1 or 2 hetero atoms other than the binding position selected from an oxygen atom, a sulfur atom and a nitrogen atom in the ring, which is derived from indoline, isoindoline, tetrahydroindoline, tetrahydroisoindoline, hexahydroindoline, hexahydroisoindoline or the like. The term "hetrocycloalkyl($C_{1-6}$ alkyl) group" means the above $C_{1-6}$ alkyl group substituted by the above heterocycloalkyl group; the term "hetrocycloalkyl($C_{1-6}$ alkoxy) group" means the above $C_{1-6}$ alkoxy group substituted by the above heterocycloalkyl group; and the term "hetrocycloalkyl($C_{1-6}$ alkylthio) group" means the above $C_{1-6}$ alkylthio group substituted by the above heterocycloalkyl group.

The term "$C_{6-10}$ aryl group" or "$C_{6-10}$ aryl-" means an aromatic cyclic hydrocarbon group having 6 or 10 carbon atoms such as a phenyl group, a naphthyl group or the like; the term "$C_{6-10}$ aryl-substituted ($C_{1-6}$ alkyl) group" means the above $C_{1-6}$ alkyl group substituted by the above $C_{6-10}$ aryl group; the term "$C_{6-10}$ aryl-substituted ($C_{1-6}$ alkoxy) group" means the above $C_{1-6}$ alkoxy group substituted by the above $C_{6-10}$ aryl group; and the term "$C_{6-10}$ aryl-substituted ($C_{1-6}$ alkylthio) group" means the above $C_{1-6}$ alkylthio group substituted by the above $C_{6-10}$ aryl group. The term "$C_{6-10}$ aryl-sulfonylamino group" means a sulfonylamino group having the above $C_{6-10}$ aryl group, such as a benzenesulfonylamino group or the like; the term "$C_{6-10}$ aryl-substituted ($C_{2-7}$ alkoxycarbonyl) group" means the above $C_{2-7}$ alkoxycarbonyl group substituted by the above $C_{6-10}$ aryl group; and the term "heteroaryl group" or "heteroaryl-" means a 5 or 6-membered aromatic heterocyclic group containing any 1 to 4 hetero atoms other than the binding position selected from an oxygen atom, a sulfur atom and a nitrogen atom in the ring, which is derived from thiazole, oxazole, isothiazole, isooxazole, pyridine, pyrimidine, pyrazine, pyridazine, pyrrole, thiophene, furan, imidazole, pyrazole, oxadiazole, thiodiazole, tetrazole, furazan or the like, or a 5 or 6-membered aromatic heterocyclic group fused with a 6-membered aromatic heterocyclic containing any 1 to 4 hetero atoms other than the binding position selected from an oxygen atom, a sulfur atom and a nitrogen atom in the ring, which is derived from indole, isoindole, benzofuran, isobenzofuran, benzothiophen, benzooxazole, benzothiazole, indazole, benzoimidazole, quinoline, isoquinoline, phthalazine, quinoxaline, quinazoline, cinnoline, indolizine, naphthyridine, pteridine or the like. The term "heteroaryl($C_{1-6}$ alkyl) group" means the above $C_{1-6}$ alkyl group substituted by the above heteroaryl group; and the term "heteroaryl($C_{1-6}$ alkoxy) group" means the above $C_{1-6}$ alkoxy group substituted by the above heteroaryl group; the term "heteroaryl($C_{1-6}$ alkylthio) group" means the above $C_{1-6}$ alkylthio group substituted by the above heteroaryl group.

The term "aliphatic cyclic amino group" means a 5 or 6-membered aliphatic cyclic amino group which may contain one hetero atom other than the nitrogen atom at the binding position selected from an oxygen atom, a sulfur atom and nitrogen atom in the ring, such as a morpholino group, a thiomorpholino group, a 1-aziridinyl group, a 1-azetidinyl group, a 1-pyrrolidinyl group, a piperidino group, a 1-imidazolidinyl group, a 1-piperazinyl group, a pyrazolidinyl group or the like; the term "aromatic cyclic amino group" means a 5-membered aromatic cyclic amino group which may contain 1 to 3 nitrogen atoms other than the nitrogen atom at the binding position, such as a 1-imidazolyl group, a 1-pyrrolyl group, a pyrazolyl group, a 1-tetrazolyl group or the like; the term "aromatic cyclic amino($C_{1-6}$ alkyl) group" means the above $C_{1-6}$ alkyl group substituted by the above aromatic cyclic amino group; the term "aromatic cyclic amino($C_{1-6}$ alkoxy) group" means the above $C_{1-6}$ alkoxy group substituted by the above aromatic cyclic amino group; and the term "aromatic cyclic amino($C_{1-6}$ alkylthio) group" means the above $C_{1-6}$ alkylthio group substituted by the above aromatic cyclic amino group.

The term "hydroxy-protective group" means a hydroxy-protective group used in general organic synthesis such as a methyl group, a benzyl group, a methoxymethyl group, an acetyl group, a pivaloyl group, a benzoyl group, a tert-butyldimethylsilyl group, a tert-butyldiphenylsilyl group, an allyl group or the like; the term "amino-protective group" means an amino-protective group used in general organic synthesis such as a benzyloxycarbonyl group, a tert-butoxycarbonyl group, a benzyl group, an acetyl group, a trifluoroacetyl group or the like; and the term "carboxy-protective group" means a carboxy-protective group used in general organic synthesis such as a methyl group, an ethyl group, a benzyl group, a tert-butyldimethylsilyl group, an allyl group or the like. The term "prodrug" means a compound which is converted into a fused heterocyclic derivative represented by the above general formula (I) as an active form thereof in vivo.

The compounds represented by the above general formula (I) of the present invention can be prepared according to the following procedures or analogous procedures thereof, or other procedures described in literatures or analogous procedures thereof.

In the present invention, for example, a compound wherein $R^2$ is a hydrogen atom; Y is —O—; and Q is an ethylene group can be prepared according to the procedures of the following processes 1 to 16:
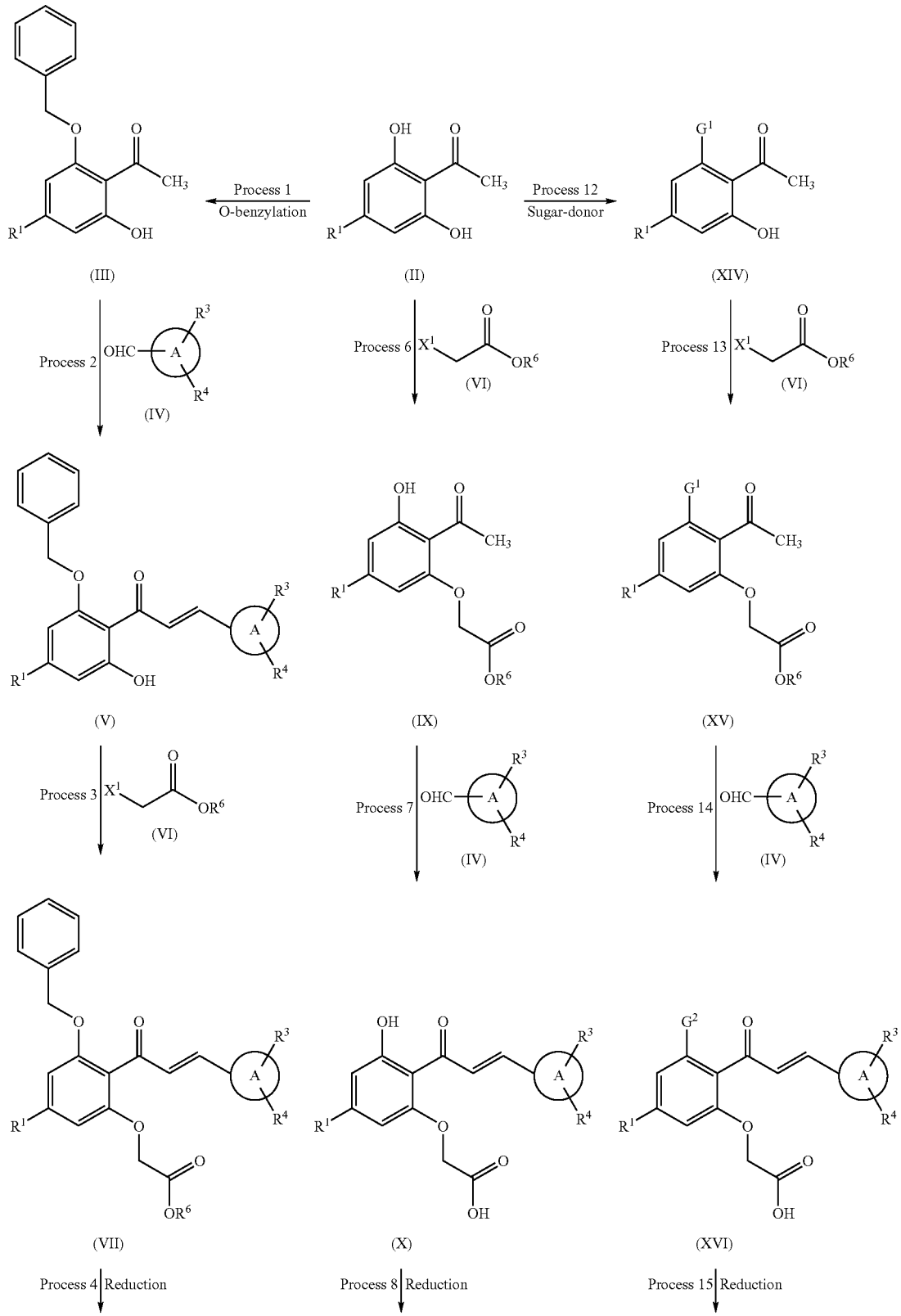

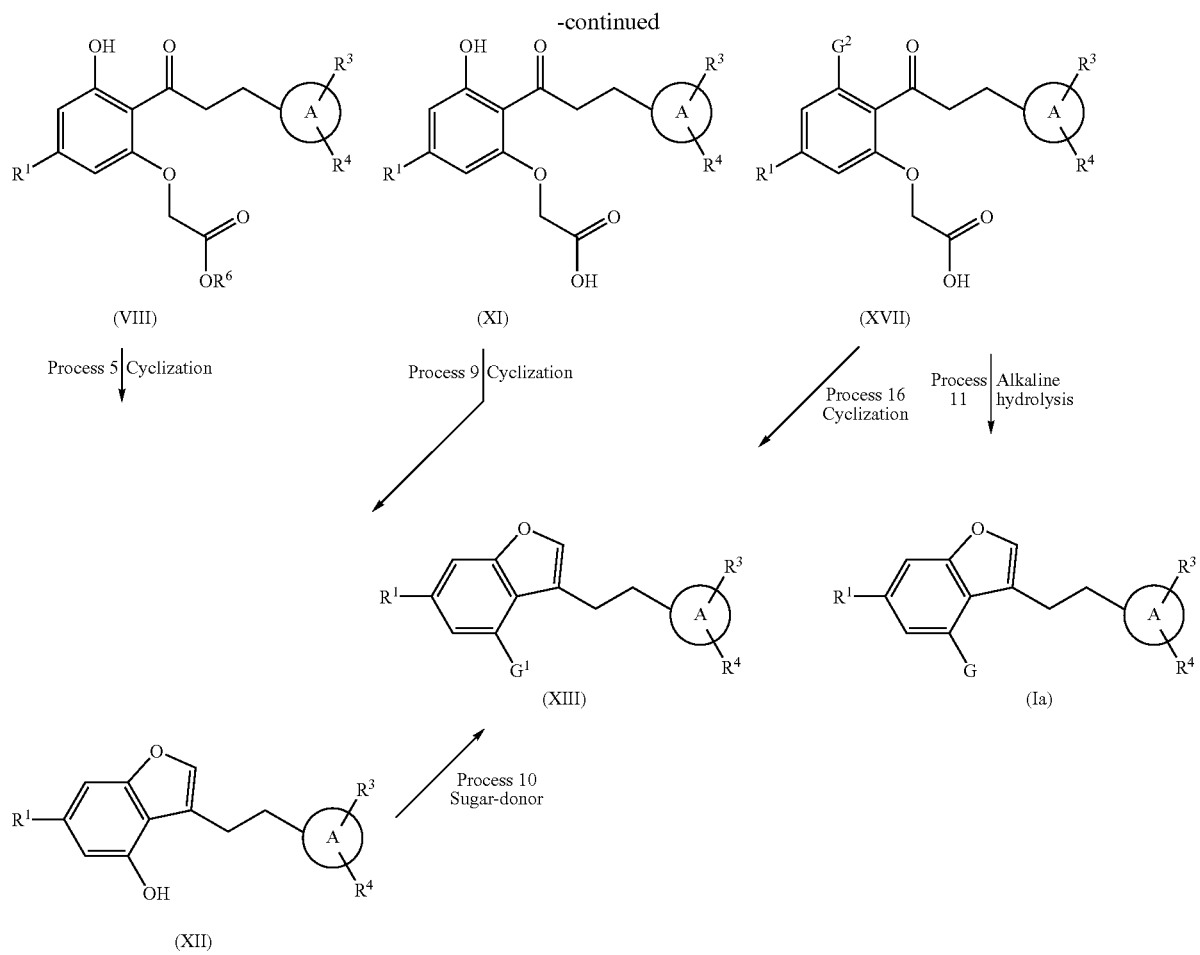

wherein $G^1$ represents the above G in which any of hydroxy groups thereof is protected; $G^2$ represents the above G in which any of hydroxy groups thereof may be protected; $R^6$ represents a methyl group or an ethyl group; $X^1$ represents a leaving group such as a halogen atom; and $R^1$, $R^3$, $R^4$, G and ring A have the same meanings as defined above, and with the proviso that a compound having a protective group can be optionally used when a hydroxy group, an amino group and/or a carboxy group exists in each compound.

Process 1

A compound represented by the above general formula (III) can be prepared by O-benzylating a phenol derivative represented by the above general formula (II) using benzyl chloride or benzyl bromide in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 2

A compound represented by the above general formula (V) can be prepared by subjecting a ketone derivative represented by the above general formula (III) to aldole reaction with an arylaldehyde derivative represented by the above general formula (IV) in the presence of a base such as potassium hydroxide, sodium hydroxide, potassium tert-butoxide, sodium tert-butoxide, sodium methoxide, sodium ethoxide or the like in an inert solvent. As the solvent used, for example, methanol, ethanol, 2-propanol, n-butanol, tetrahydrofuran, water, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 3

A compound represented by the above general formula (VII) can be prepared by O-alkylating a phenol derivative represented by the above general formula (V) using a haloacetate ester represented by the above general formula (VI) such as methyl bromoacetate, ethyl bromoacetate, methyl chloroacetate, ethyl chloroacetate or the like in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from room temperature to reflux temperature, and the reaction time is usually from 1 hour to 5 days, varying based on a used starting material, solvent and reaction temperature.

Process 4

A compound represented by the above general formula (VIII) can be prepared by subjecting a compound represented by the above general formula (VII) to catalytic hydrogenation for reduction of double bond and removal of the benzyl group using a palladium catalyst such as palladium-carbon powder in an inert solvent. As the solvent used in the catalytic hydrogenation, for example, methanol, ethanol, 2-propanol, tetrahydrofuran, ethyl acetate, acetic acid, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 5

A benzofuran derivative represented by the above general formula (XII) can be prepared by subjecting a compound represented by the above general formula (VIII) to cyclization in the presence of abase such as sodium methoxide, sodium ethoxide, potassium tert-butoxide, sodium tert-butoxide or the like in an inert solvent, optionally 1) by adding water and treating the reaction mixture with sodium hydroxide or potassium hydroxide, and 2) by treating the obtained compound in the presence of copper powder in quinoline. As the solvent used in cyclization, for example, methanol, ethanol, 2-propanol, n-butanol, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 6

A compound represented by the above general formula (IX) can be prepared by O-alkylating a phenol derivative represented by the above general formula (II) using a haloacetate ester represented by the above general formula (VI) such as methyl bromoacetate, ethyl bromoacetate, methyl chloroacetate, ethyl chloroacetate or the like in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from room temperature to reflux temperature, and the reaction time is usually from 1 hour to 5 days, varying based on a used starting material, solvent and reaction temperature.

Process 7

A compound represented by the above general formula (X) can be prepared by subjecting a ketone derivative represented by the above general formula (IX) and an arylaldehyde derivative represented by the above general formula (IV) to aldole reaction and hydrolysis at the same time in the presence of a base such as potassium hydroxide, sodium hydroxide or the like in an inert solvent. As the solvent used, for example, methanol, ethanol, 2-propanol, n-butanol, tetrahydrofuran, water, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 8

A compound represented by the above general formula (XI) can be prepared by conducting catalytic hydrogenation to reduce the double bond of a compound represented by the above general formula (X) using a palladium catalyst such as palladium-carbon powder in an inert solvent. As the solvent used, for example, methanol, ethanol, 2-propanol, tetrahydrofuran, ethyl acetate, acetic acid, water, a mixed solvent thereof and the like can be illustrated. The reaction temperature is usually from room temperature to reflux temperature, and the reaction time is usually from 1 hour to 2 days, varying based on a used starting material, solvent and reaction temperature.

In addition, a compound represented by the above general formula (XI) can be also prepared by conducting hydrogenation to reduce the double bond of a compound represented by the above general formula (X) using a reagent such as triethylsilane or the like in the presence of rhodium catalyst such as tris(triphenylphosphine) rhodium (I) chloride or the like in an inert solvent. As the solvent used, for example, benzene, toluene, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 9

A benzofuran derivative represented by the above general formula (XII) can be prepared by subjecting a compound represented by the above general formula (XI) to cyclization, and optionally to alkaline hydrolysis to deprotect its hydroxy group acetylated on the cyclization reaction in the presence of sodium acetate and acetic anhydride in an inert solvent. As the solvent used in the cyclization, for example, acetic acid and the like can be illustrated. The reaction temperature is usually from 50° C. to reflux temperature, and the reaction time is usually from 1 hour to 3 days, varying based on a used starting material, solvent and reaction temperature. As the solvent used in the alkaline hydrolysis, for example, water, methanol, ethanol, a mixed solvent thereof and the like can be illustrated. As the base, for example, sodium hydroxide, sodium methoxide, sodium ethoxide and the like can be illustrated. The reaction temperature is usually from 0°C. to reflux temperature, and the reaction time is usually from 30 minutes to 1 day, varying based on a used starting material, solvent and reaction temperature.

Process 10

A glycoside compound represented by the above general formula (XIII) can be prepared by subjecting a compound represented by the above general formula (XII) to glycosidation using a sugar donor compound such as 2,3,4,6-tetra-O-acetyl-1-O-trichloroacetoimidoyl-α-D-glucopyranose, 2,3,4,6-tetra-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 11

A compound represented by the above general formula (Ia) of the present invention can be prepared by subjecting a glycoside compound represented by the above general formula (XIII) to alkaline hydrolysis to remove the protective group. As the solvent used, for example, water, methanol, ethanol, tetrahydrofuran, a mixed solvent thereof and the like can be illustrated. As a base, for example, sodium hydroxide, sodium methoxide, sodium ethoxide or the like can be used. The temperature is usually from 0° C. to reflux temperature, and the reaction time is usually from 30 minutes to 1 day, varying based on a used starting material, solvent and reaction temperature.

Process 12

A glycoside compound represented by the above general formula (XIV) can be prepared by subjecting a compound represented by the above general formula (II) to glycosidation using a sugar donor compound such as 2,3,4,6-tetra-O-acetyl-α-D-glucopyranosyl bromide, 2,3,4,6-tetra-O-acetyl-α-D-glucopyranosyl bromide, 2,3,4,6-tetra-O-pivaloyl-α-D-galactopyranosyl bromide, 2,3,4,6-tetra-O-benzoyl-α-D-glucopyranosyl bromide, 2,3,4,6-tetra-O-benzoyl-α-D-galactopyranosyl bromide or the like in the presence of a phase-transfer catalyst such as benzyl tri(n-butyl)ammonium chloride, benzyl tri(n-butyl)ammonium bromide, tetra(n-butyl)ammonium hydrogen sulfate or the like and a base such as sodium hydroxide, potassium hydroxide, potassium carbonate or the like in a hydrous inert solvent. As the inert solvent used, for example, dichloromethane, chloroform, toluene, benzotrifluoride, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 13

A compound represented by the above general formula (XV) can be prepared by O-alkylating a phenol derivative represented by the above general formula (XIV) using a haloacetate ester represented by the above general formula (VI) such as methyl bromoacetate, ethyl bromoacetate, methyl chloroacetate, ethyl chloroacetate or the like in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from room temperature to reflux temperature, and the reaction time is usually from 1 hour to 5 days, varying based on a used starting material, solvent and reaction temperature.

Process 14

A compound represented by the above general formula (XVI) can be prepared by subjecting a ketone derivative represented by the above general formula (XV) and an arylaldehyde derivative represented by the above general formula (IV) to aldole reaction and hydrolysis at the same time in the presence of a base such as potassium hydroxide, sodium hydroxide or the like in an inert solvent. As the solvent used, for example, methanol, ethanol, 2-propanol, n-butanol, tetrahydrofuran, water, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 15

A compound represented by the above general formula (XVII) can be prepared by conducting catalytic hydrogenation to reduce the double bond of a compound represented by the above general formula (XVI) using a palladium catalyst such as palladium-carbon powder in an inert solvent. As the solvent used, for example, methanol, ethanol, 2-propanol, tetrahydrofuran, ethyl acetate, acetic acid, water, a mixed solvent thereof and the like can be illustrated. The reaction temperature is usually from room temperature to reflux temperature, and the reaction time is usually from 1 hour to 2 days, varying based on a used starting material, solvent and reaction temperature.

In addition, a compound represented by the above general formula (XVII) can be also prepared by conducting hydrogenation to reduce the double bond of a compound represented by the above general formula (XVI) using a reagent such as triethylsilane or the like in the presence of rhodium catalyst such as tris(triphenylphosphine) rhodium (I) chloride or the like in an inert solvent. As the solvent used, for example, benzene, toluene, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 16

A benzofuran derivative represented by the above general formula (XIII) can be prepared by subjecting a compound represented by the above general formula (XVII) to cyclization in the presence of sodium acetate and acetic anhydride in an inert solvent. As the solvent used in the reaction, for example, acetic acid and the like can be illustrated. The reaction temperature is usually from 50° C. to reflux temperature, and the reaction time is usually from 1 hour to 3 days, varying based on a used starting material, solvent and reaction temperature.

Of the compounds represented by the above general formula (I) of the present invention, a compound wherein $R^1$ is a hydroxy group; $R^2$ is a hydrogen atom; Y is —O—; and Q is an ethylene group can be prepared according to the procedures of the following processes 17 to 25:

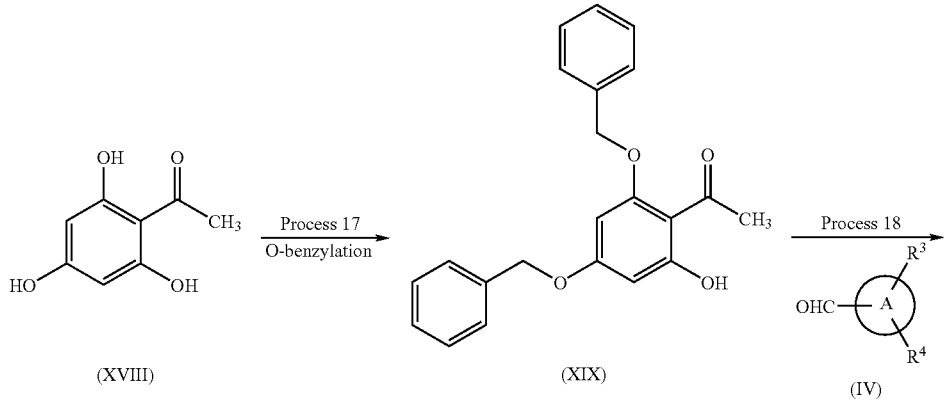

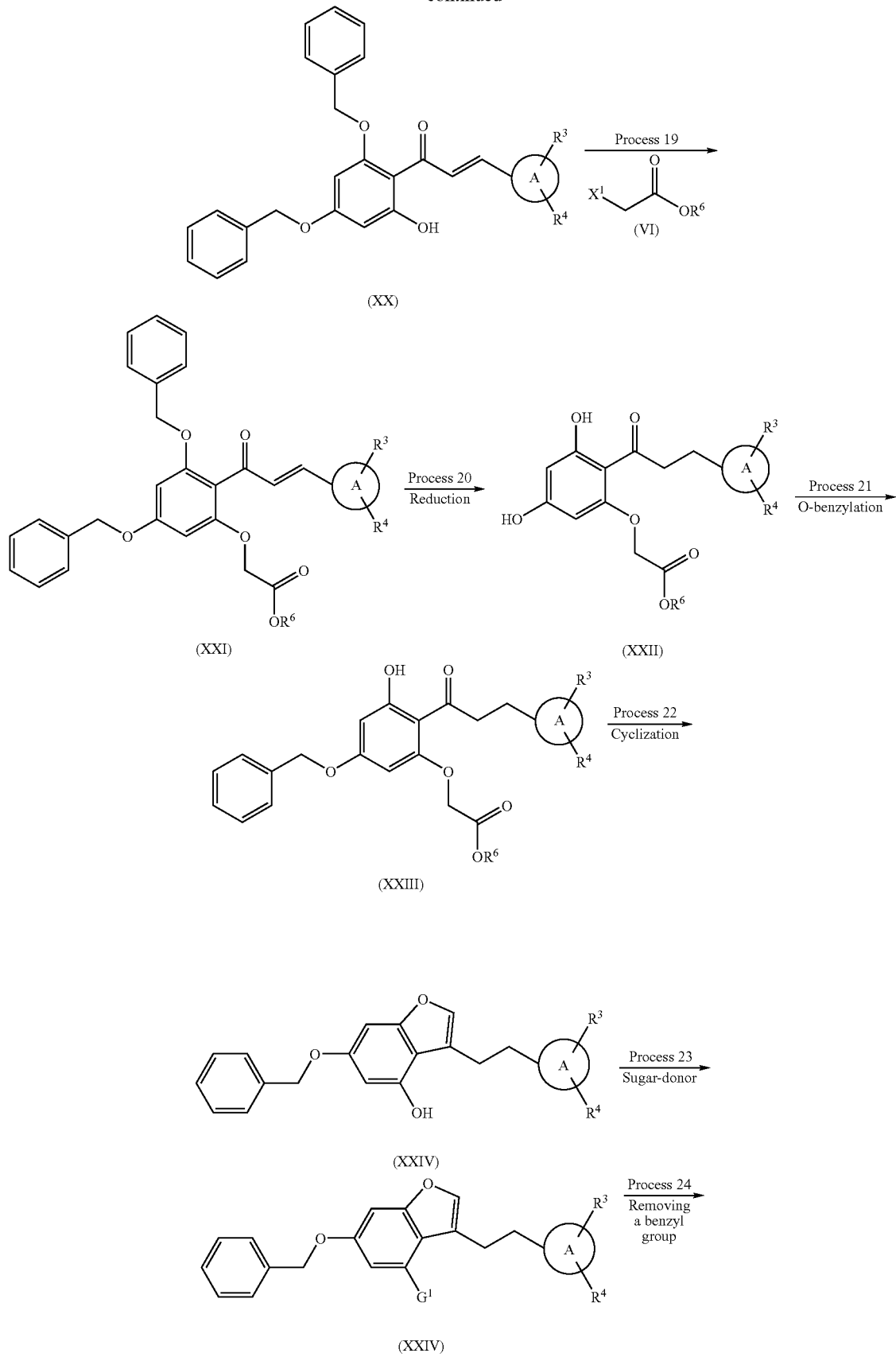

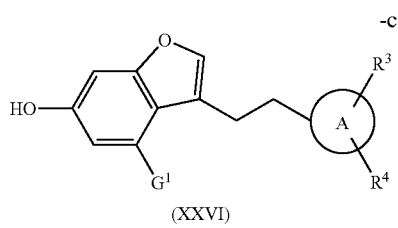

(XXVI)

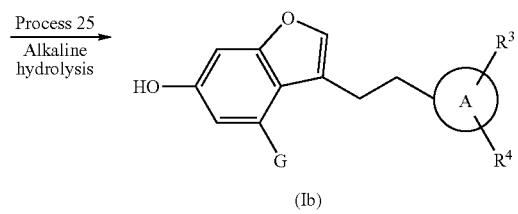

(Ib)

wherein $R^3$, $R^4$, $R^6$, G, $G^1$, $X^1$ and ring A have the same meanings as defined above, and with the proviso that a compound having a protective group can be optionally used when a hydroxy group, an amino group and/or a carboxy group exists in each compound.

Process 17

A compound represented by the above general formula (XIX) can be prepared by O-benzylating a phenol derivative represented by the above general formula (XVIII) using benzyl chloride or benzyl bromide in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 18

A compound represented by the above general formula (XX) can be prepared by subjecting a ketone derivative represented by the above general formula (XIX) to aldole reaction with an arylaldehyde derivative represented by the above general formula (IV) in the presence of a base such as potassium hydroxide, sodium hydroxide, potassium tert-butoxide, sodium tert-butoxide, sodium methoxide, sodium ethoxide or the like in an inert solvent. As the solvent used, for example, methanol, ethanol, 2-propanol, n-butanol, tetrahydrofuran, water, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 19

A compound represented by the above general formula (XXI) can be prepared by O-alkylating a phenol derivative represented by the above general formula (XX) using a haloacetate ester represented by the above general formula (VI) such as methyl bromoacetate, ethyl bromoacetate, methyl chloroacetate, ethyl chloroacetate or the like in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from room temperature to reflux temperature, and the reaction time is usually from 1 hour to 5 days, varying based on a used starting material, solvent and reaction temperature.

Process 20

A compound represented by the above general formula (XXII) can be prepared by subjecting a compound represented by the above general formula (XXI) to catalytic hydrogenation for reduction of double bond and removal of the benzyl group using a palladium catalyst such as palladium-carbon powder in an inert solvent. As the solvent used in the catalytic hydrogenation, for example, methanol, ethanol, 2-propanol, tetrahydrofuran, ethyl acetate, acetic acid, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 21

A compound represented by the above general formula (XXIII) can be prepared by O-benzylating a phenol derivative represented by the above a general formula (XXII) using benzyl chloride or benzyl bromide in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from 0° C. to reflux temperature, and the reaction time is usually from 1 hour to 3 days, varying based on a used starting material, solvent and reaction temperature.

Process 22

A benzofuran derivative represented by the above general formula (XXIV) can be prepared by subjecting a compound represented by the above general formula (XXIII) to cyclization in the presence of a base such as sodium methoxide, sodium ethoxide, potassium tert-butoxide, sodium tert-butoxide or the like in an inert solvent, optionally 1) by adding water and treating the reaction mixture with sodium hydroxide or potassium hydroxide, and 2) by treating the obtained compound in the presence of copper powder in quinoline. As the solvent used in cyclization, for example, methanol, ethanol, 2-propanol, n-butanol, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 23

A glycoside compound represented by the above general formula (XXV) can be prepared by subjecting a compound represented by the above general formula (XXIV) to glycosidation using a sugar donor compound such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 24

A compound represented by the above general formula (XXVI) can be prepared by subjecting a compound represented by the above general formula (XXV) to catalytic hydrogenation to remove the benzyl group using a palladium catalyst such as palladium-carbon powder in an inert solvent. As the solvent used in the catalytic hydrogenation, for example, methanol, ethanol, 2-propanol, tetrahydrofuran, ethyl acetate, acetic acid, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 25

A compound represented by the above general formula (Ib) of the present invention can be prepared by subjecting a glycoside compound represented by the above general formula (XXVI) to alkaline hydrolysis to remove the protective group. As the solvent used, for example, water, methanol, ethanol, tetrahydrofuran, a mixed solvent thereof and the like can be illustrated. As a base, for example, sodium hydroxide, sodium methoxide, sodium ethoxide or the like can be used. The temperature is usually from 0° C. to reflux temperature, and the reaction time is usually from 30 minutes to 1 day, varying based on a used starting material, solvent and reaction temperature.

Of the compounds represented by the above general formula (I) of the present invention, a compound wherein $R^2$ is a hydrogen atom; Y is —NH— which may be substituted by a $C_{1-6}$ alkyl group or a halo($C_{1-6}$ alkyl) group; and Q is an ethylene group can be prepared according to the procedures of the following processes 26 to 34:

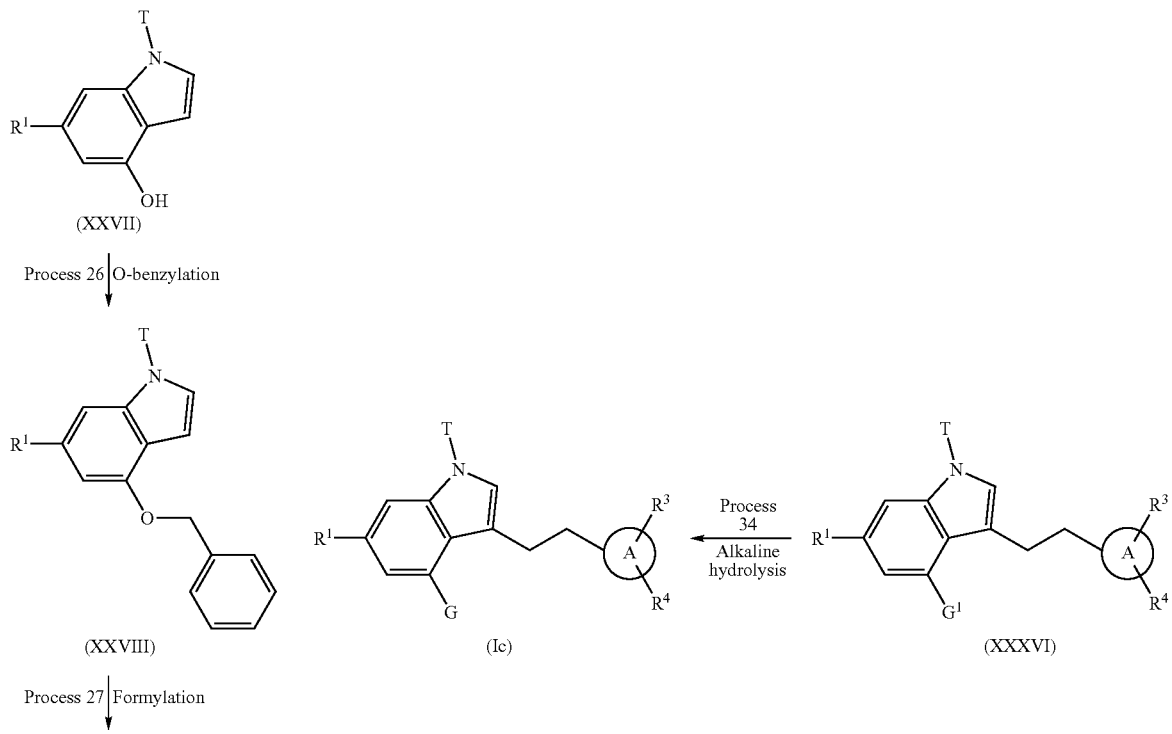

-continued

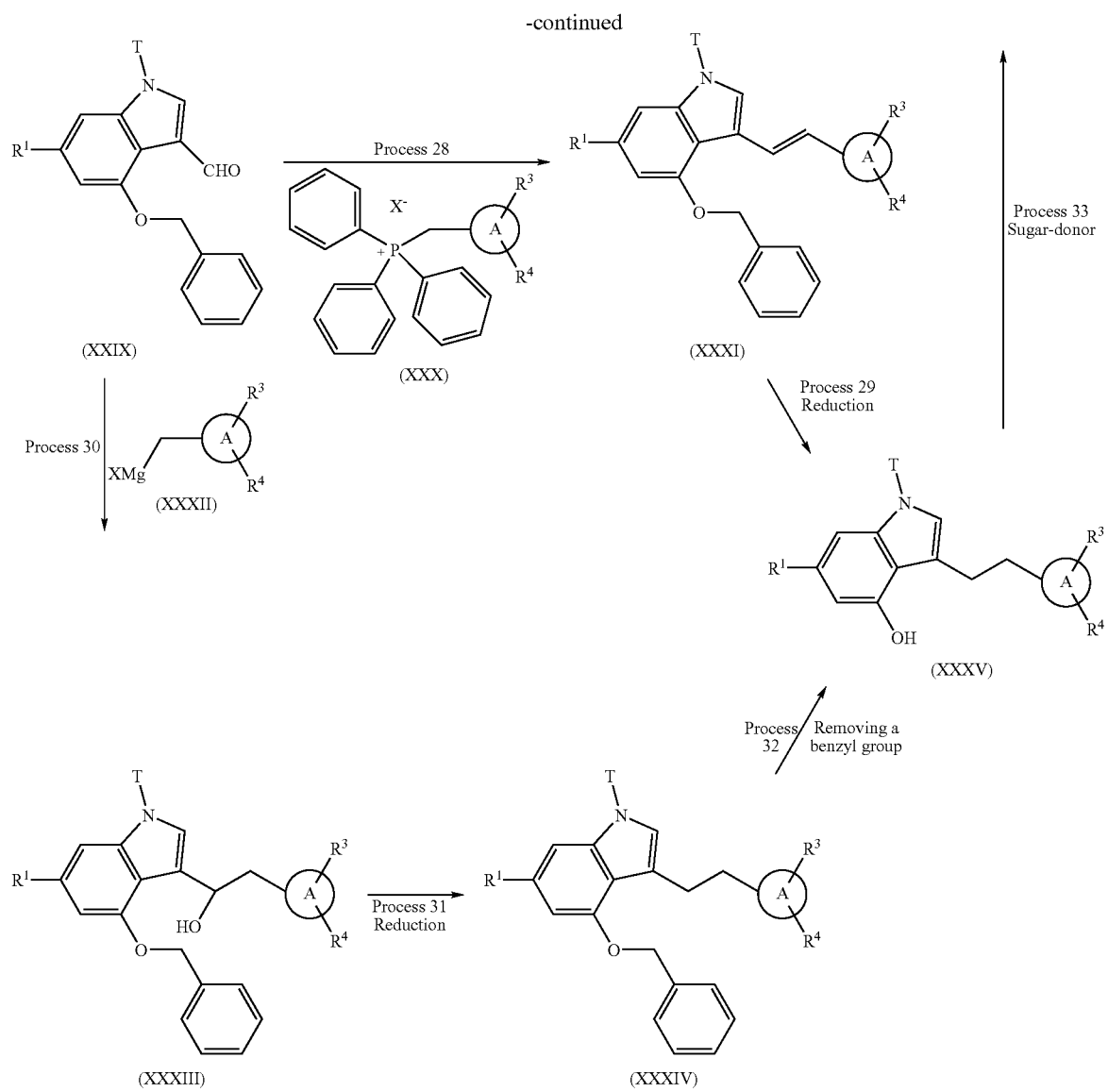

wherein T represents a hydrogen atom, a $C_{1-6}$ alkyl group or a halo($C_{1-6}$ alkyl) group; X represents a bromine atom, a chlorine atom or a iodine atom; and $R^1$, $R^3$, $R^4$, G, $G^1$ and ring A have the same meanings as defined above, and with the proviso that a compound having a protective group can be optionally used when a hydroxy group, an amino group and/or a carboxy group exists in each compound.

Process 26

A compound represented by the above general formula (XXVIII) can be prepared by O-benzylating a phenol derivative represented by the above general formula (XXVII) using benzyl chloride or benzyl bromide in the presence of a base such as potassium carbonate, cesium carbonate or the like in an inert solvent. As the solvent used, for example, N,N-dimethylformamide, acetone, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 27

A compound represented by the above general formula (XXIX) can be prepared by subjecting a compound represented by the above general formula (XXVIII) to Vilsmeier reaction to introduce a formyl group using phosphorous oxychloride and N,N-dimethylformamide in an inert solvent. As the solvent used, for example, N,N-dimethylformamide, acetonitrile, dichloromethane, 1,2-dichloroethane, a mixed solvent thereof and the like can be illustrated. The reaction temperature is usually from −20° C. to reflux temperature, and the reaction time is usually from 30 minutes to 1 day, varying based on a used starting material, solvent and reaction temperature.

Process 28

A olefin compound represented by the above general formula (XXXI) can be prepared by subjecting a compound represented by the above general formula (XXIX) and a phosphonium salt represented by the above general formula (XXX) to Wittig reaction in the presence of abase such as sodium hydride, sodium hydroxide, potassium tert-butoxide, n-butyllithium, tert-butyllithium or the like in an inert solvent. As the solvent used, for example, tetrahydrofuran, N,N-dimethylformamide, dimethylsulfoxide, a mixed solvent thereof and the like can be illustrated. The reaction temperature is usually from −20° C. to reflux temperature, and the reaction time is usually from 30 minutes to 1 day, varying based on a used starting material, solvent and reaction temperature.

Process 29

A compound represented by the above general formula (XXXV) can be prepared by subjecting a compound represented by the above general formula (XXXI) to catalytic hydrogenation for reduction of double bond and removal of the benzyl group using a palladium catalyst such as palladium-carbon powder in an inert solvent. As the solvent used in the catalytic hydrogenation, for example, methanol, ethanol, 2-propanol, tetrahydrofuran, ethyl acetate, acetic acid, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 30

A compound represented by the above general formula (XXXIII) can be prepared by subjecting a compound represented by the above general formula (XXIX) to Grignard reaction using a Grignard reagent represented by the above general formula (XXXII) in an inert solvent. As the solvent used, for example, tetrahydrofuran, diethyl ether, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 31

A compound represented by the above general formula (XXXIV) can be prepared by subjecting a compound represented by the above general formula (XXXIII) to reduction using a reduction reagent such as borane-tetrahydrofuran complex, borane-dimethylsulfide complex or the like in the presence of an additive such as 4-dimethylaminopyridine in an inert solvent. As the solvent used, for example, tetrahydrofuran, diethyl ether, a mixed solvent thereof and the like can be illustrated. The reaction temperature is usually from 0° C. to reflux temperature, and the reaction time is usually from 30 minutes to 5 days, varying based on a used starting material, solvent and reaction temperature.

In addition, a compound represented by the above general formula (XXXIV) can be also prepared by subjecting a compound represented by the above general formula (XXXIII) to reduction using a reagent such as triethylsilane or the like in the presence of an acid such as trifluoroacetatic acid, boron trifluoride-diethyl ether complex or the like in an inert solvent. As the solvent used, for example, dichloromethane, 1,2-dichloroethane, a mixed solvent thereof and the like can be illustrated. The reaction temperature is usually from −20° C. to reflux temperature, and the reaction time is usually from 30 minutes to 5 days, varying based on a used starting material, solvent and reaction temperature.

Process 32

A compound represented by the above general formula (XXXV) can be prepared by subjecting a compound represented by the above general formula (XXXIV) to catalytic hydrogenation to remove the benzyl group using a palladium catalyst such as palladium-carbon powder in an inert solvent. As the solvent used in the catalytic hydrogenation, for example, methanol, ethanol, 2-propanol, tetrahydrofuran, ethyl acetate, acetic acid, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 33

A glycoside compound represented by the above general formula (XXXVI) can be prepared by subjecting a compound represented by the above general formula (XXXV) to glycosidation using a sugar donor compound such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 34

A compound represented by the above general formula (Ic) of the present invention can be prepared by subjecting a glycoside compound represented by the above general formula (XXXVI) to alkaline hydrolysis to remove the protective group. As the solvent used, for example, water, methanol, ethanol, tetrahydrofuran, a mixed solvent thereof and the like can be illustrated. As a base, for example, sodium hydroxide, sodium methoxide, sodium ethoxide or the like can be used. The temperature is usually from 0° C. to reflux temperature, and the reaction time is usually from 30 minutes to 1 day, varying based on a used starting material, solvent and reaction temperature.

Of the compounds represented by the above general formula (I) of the present invention, a compound wherein $R^2$ is a hydrogen atom; Y is —S—; and Q is —$C_{1-6}$ alkylene-, —$C_{2-6}$ alkenylene-, —$C_{1-6}$ alkylene-O—, —$C_{1-6}$ alkylene-S—, —$C_{1-6}$ alkylene-O—$C_{1-6}$ alkylene- or —$C_{1-6}$ alkylene-S—$C_{1-6}$ alkylene- can be prepared according to the procedures of the following processes 35 to 42:

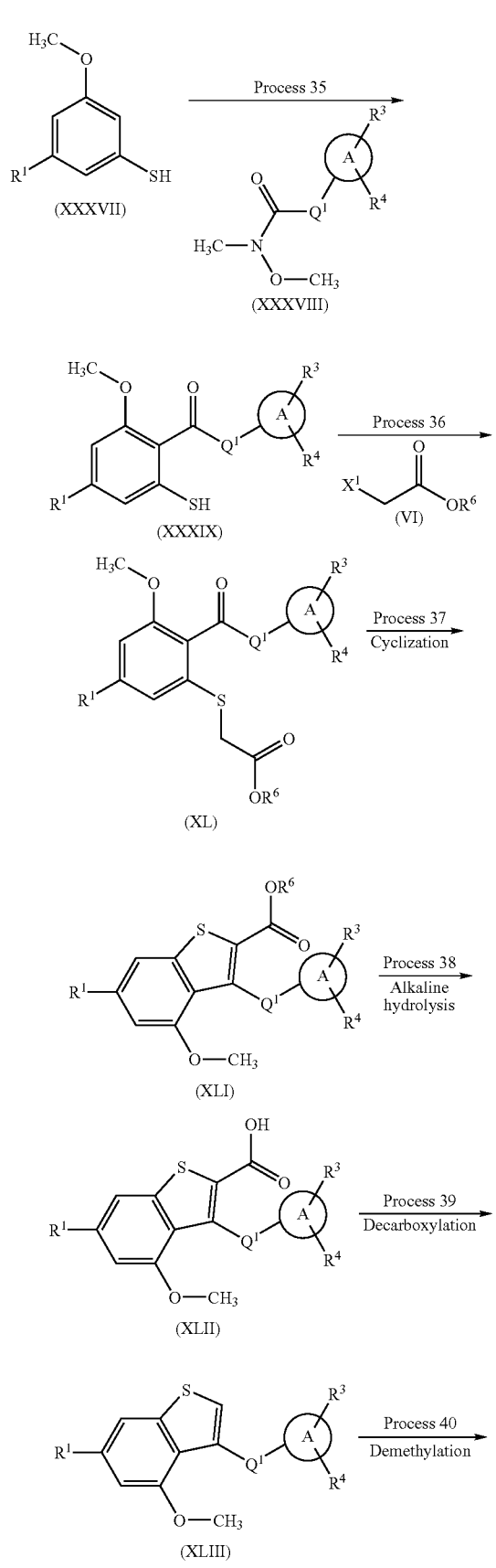

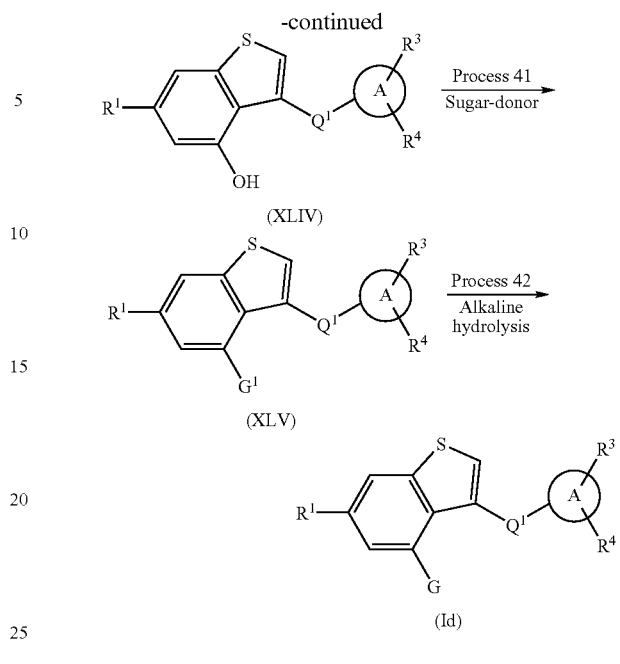

wherein $Q^1$ represents —$C_{1-6}$ alkylene-, —$C_{2-6}$ alkenylene-, —$C_{1-6}$ alkylene-O—, —$C_{1-6}$ alkylene-S—, —$C_{1-6}$ alkylene-O—$C_{1-6}$ alkylene- or —$C_{1-6}$ alkylene-S—$C_{1-6}$ alkylene-; and $R^1$, $R^3$, $R^4$, $R^6$, G, $G^1$, $X^1$ and ring A have the same meanings as defined above, and with the proviso that a compound having a protective group can be optionally used when a hydroxy group, an amino group and/or a carboxy group exists in each compound.

Process 35

A compound represented by the above general formula (XXXIX) can be prepared by treating a compound represented by the above general formula (XXXVII) using a lithiating reagent such as n-butyllithium, sec-butyllithium, tert-butyllithium or the like in the presence of an additive such as N,N,N',N'-tetramethylethylenediamine, hexamethylphosphorous triamide or the like in an inert solvent, and adding an amide derivative represented by the above general formula (XXXVIII) in an inert solvent. As the solvent used, for example, cyclohexane, n-hexane, tetrahydrofuran, diethyl ether, a mixed solvent thereof and the like can be illustrated. The temperature is usually from −20° C. to reflux temperature, and the reaction time is usually from 30 minutes to 1 day, varying based on a used starting material, solvent and reaction temperature.

Process 36

A compound represented by the above general formula (XL) can be prepared by S-alkylating a thiophenol derivative represented by the above general formula (XXXIX) using a haloacetate ester represented by the above general formula (VI) such as methyl bromoacetate, ethyl bromoacetate, methyl chloroacetate, ethyl chloroacetate or the like in the presence of a base such as triethylamine, N,N-diisopropylethylamine or the like in an inert solvent. As the solvent used, for example, dichloromethane, tetrahydrofuran, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 37

A benzothiophen derivative represented by the above general formula (XLI) can be prepared by subjecting a compound represented by the above general formula (XL) to cyclization in the presence of abase such as sodium methoxide, sodium ethoxide, potassium tert-butoxide, sodium tert-butoxide or the like in an inert solvent. As the solvent used in cyclization, for example, methanol, ethanol, 2-propanol, n-butanol, a mixed solvent thereof and the like can be illustrated. The reaction temperature is usually from room temperature to reflux temperature, and the reaction time is usually from 1 hour to 2 days, varying based on a used starting material, solvent and reaction temperature.

Process 38

A compound represented by the above general formula (XLII) can be prepared by subjecting a compound represented by the above general formula (XLI) to alkaline hydrolysis. As the solvent used, for example, methanol, ethanol, 2-propanol, tetrahydrofuran, water, a mixed solvent thereof and the like can be illustrated. As a base, for example, sodium hydroxide, potassium hydroxide or the like can be used. The temperature is usually from room temperature to reflux temperature, and the reaction time is usually from 1 hour to 1 day, varying based on a used starting material, solvent and reaction temperature.

Process 39

A compound represented by the above general formula (XLIII) can be prepared by subjecting a compound represented by the above general formula (XLII) to decarboxylation in the presence of a catalyst such as copper powder or the like in an inert solvent. As the solvent used, for example, quinoline and the like can be illustrated. The temperature is usually from 100° C. to reflux temperature, and the reaction time is usually from 30 minutes to 1 day, varying based on a used starting material, solvent and reaction temperature.

Process 40

A compound represented by the above general formula (XLIV) can be prepared by subjecting a compound represented by the above general formula (XLIII) to demethylation in the presence of a reagent such as boron tribromide, boron trichloride or the like in an inert solvent. As the solvent used, for example, dichloromethane, 1,2-dichloroethane, benzene, toluene, a mixed solvent thereof and the like can be illustrated. The temperature is usually from −78° C. to reflux temperature, and the reaction time is usually from 30 minutes to 1 day, varying based on a used starting material, solvent and reaction temperature.

Process 41

A glycoside compound represented by the above general formula (XLV) can be prepared by subjecting a compound represented by the above general formula (XLIV) to glycosidation using a sugar donor compound such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 42

A compound represented by the above general formula (Id) of the present invention can be prepared by subjecting a glycoside compound represented by the general formula (XLV) to alkaline hydrolysis to remove the protective group. As the solvent used, for example, water, methanol, ethanol, tetrahydrofuran, a mixed solvent thereof and the like can be illustrated. As a base, for example, sodium hydroxide, sodium methoxide, sodium ethoxide or the like can be used. The reaction temperature is usually from 0° C. to reflux temperature, and the reaction time is usually from 30 minutes to 1 day, varying based on a used starting material, solvent and reaction temperature.

Of the compounds represented by the above general formula (I) of the present invention, a compound wherein $R^2$ is a hydrogen atom; Q is an ethylene group; $R^3$ is —U—$V^1$—N($R^5$)—$R^4$ or —U—$V^1$—$NH_2$ in which $V^1$ is a $C_{1-6}$ alkylene group which may have a hydroxy group or $C_{2-6}$ alkenylene group; $R^5$, $R^4$ and U have the same meanings as defined above, can be prepared according to the procedures of the following processes 43 to 50:

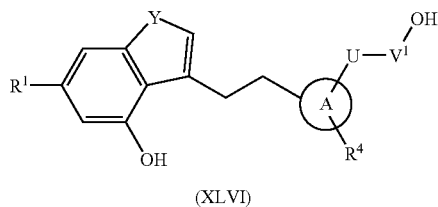

(XLVI)

Process 43 | O-Protection

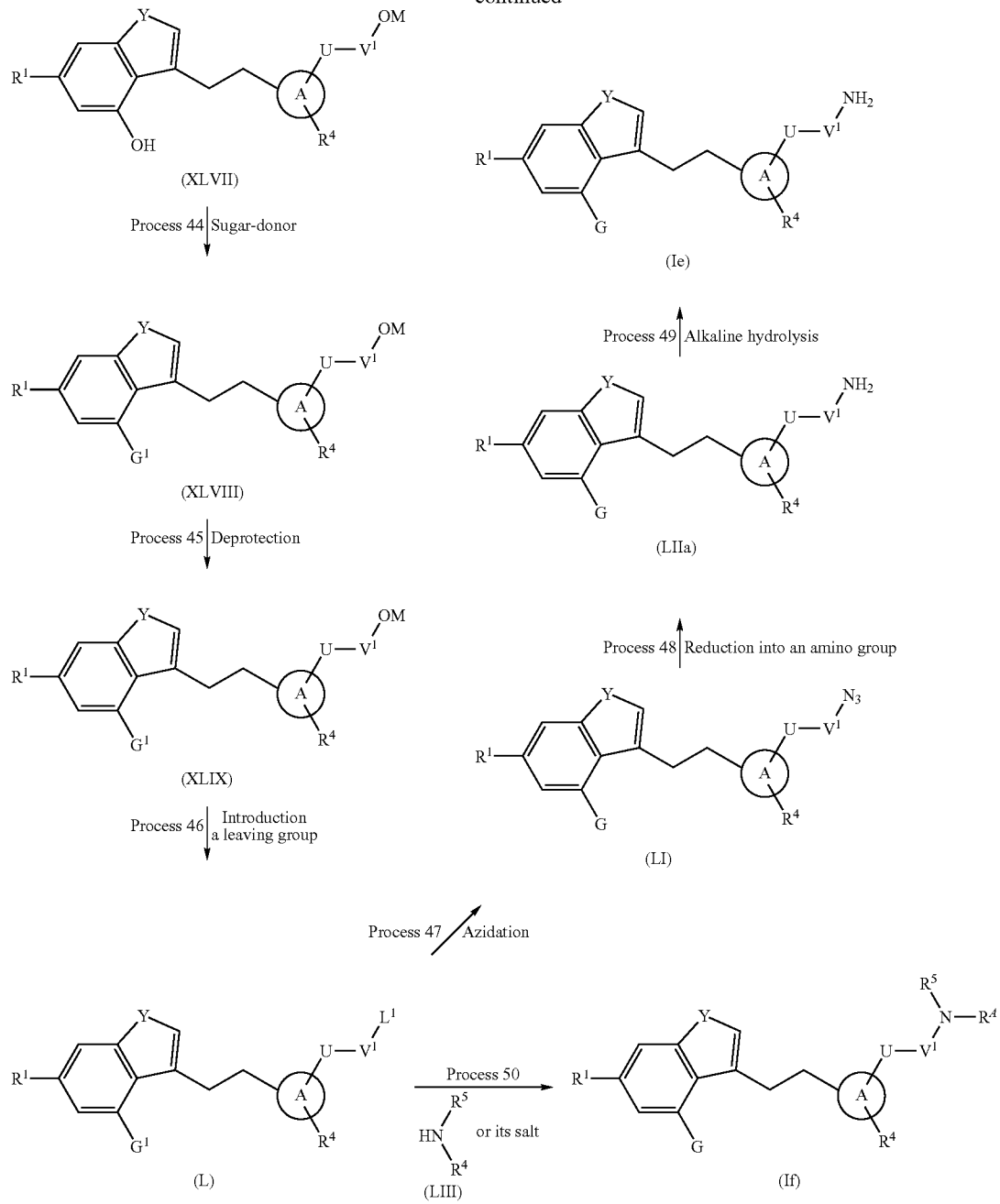

wherein L¹ represents a mesyloxy group or a tosyloxy group; M represents a hydroxy-protective silyl group; and $R^1$, $R^4$, $R^5$, $R^A$, G, $G^1$, U, $V^1$, Y and ring A have the same meanings as defined above, and with the proviso that a compound having a protective group can be optionally used when a hydroxy group, an amino group and/or a carboxy group exists in each compound.

Process 43

A compound represented by the above general formula (XLVII) can be prepared by subjecting a compound represented by the above general formula (XLVI) to O-protection using a silylating reagent such as tert-butyldiphenylsilyl chloride, tert-butyldimethylsilyl chloride, triisopropylsilyl chloride, triethylsilyl chloride or the like in the presence of a base such as imidazole, triethylamine, N,N-diisopropylethylamine or the like in an inert solvent. As the solvent used, for example, N,N-dimethylformamide, dichloromethane, a mixed solvent thereof and the like can be illustrated. The reaction temperature is usually from 0° C. to room temperature, and the reaction time is usually from 30 minutes to 1 day, varying based on a used starting material, solvent and reaction temperature.

Process 44

A glycoside compound represented by the above general formula (XLVIII) can be prepared by subjecting a compound represented by the above general formula (XLVII) to glycosidation using a sugar donor compound such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 45

A compound represented by the above general formula (XLIX) can be prepared by desilylating a compound represented by the above general formula (XLVIII) using a reagent such as tetra(n-butyl)ammonium fluoride or the like in an inert solvent. As the solvent used, for example, tetrahydrofuran and the like can be illustrated. The reaction temperature is usually from room temperature to reflux temperature, and the reaction time is usually from 1 hour to 2 days, varying based on a used starting material, solvent and reaction temperature.

Process 46

A compound represented by the above general formula (L) can be prepared by introducing a leaving group to a compound represented by the above general formula (XLIX) using an acid chloride such as mesyl chloride, tosyl chloride or the like in the presence of a base such as triethylamine, N,N-diisopropylethylamine or the like in an inert solvent. As the solvent used in the introduction reaction, for example, dichloromethane, ethyl acetate, tetrahydrofuran, pyridine, and the like can be illustrated. The reaction temperature is usually from 0° C. to room temperature, and the reaction time is usually from 30 minutes to 1 day, varying based on a used starting material, solvent and reaction temperature.

Process 47

A compound represented by the above general formula (LI) can be prepared by subjecting a compound represented by the above general formula (L) to azidation using an azidating reagent such as sodium azide or the like in an inert solvent. As the solvent used in the azidation, for example, dichloromethane, ethyl acetate, N,N-dimethylformamide, dimethyl sulfoxide, N-methylpyrrolidone, N,N-dimethylimidazolidinone, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 48

A compound represented by the above general formula (LIIa) can be prepared by subjecting a compound represented by the above general formula (LI) to catalytic hydrogenation using a palladium catalyst such as palladium-carbon powder in an inert solvent. As the solvent used in the catalytic hydrogenation, for example, tetrahydrofuran, methanol, ethanol, ethyl acetate, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 49

A compound represented by the above general formula (Ie) of the present invention can be prepared by subjecting a compound represented by the above general formula (LIIa) to alkaline hydrolysis to remove the protective group. As the solvent used in the hydrolysis reaction, for example, methanol, ethanol, tetrahydrofuran, acetonitrile, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature.

Process 50

A compound represented by the above general formula (If) of the present invention can be prepared by subjecting a compound represented by the above general formula (L) to condensation with an amine compound represented by the above general formula (LIII) or a salt thereof in the presence or absence of a base such as triethylamine, N,N-diisopropylethylamine, pyridine, 1,8-diazabicyclo[5.4.0]undec-7-ene, sodium hydride, potassium tert-butoxide, potassium carbonate or cesium carbonate, and occasionally by adding sodium iodide, in an inert solvent, and to alkaline hydrolysis in a similar way to process 49 as occasion demands. As the solvent used in the condensation, for example, acetonitrile, N,N-dimethylformamide, dimethylsulfoxide, N-methylpyrrolidone, methanol, ethanol, tetrahydrofuran, water, a mixed solvent thereof and the like can be illustrated. The reaction temperature is usually from room temperature to reflux temperature, and the reaction time is usually from 1 hour to 3 days, varying based on a used starting material, solvent and reaction temperature.

Of the compounds represented by the above general formula (I) of the present invention, a compound wherein $R^2$ is a hydrogen atom; Q is an ethylene group; $R^3$ is —U—V—NH-Z or —U—V—NHCON($R^C$)$R^D$ in which $Z^1$ is —COR$^B$, —SO$_2$R$^B$, —CONHR$^C$ or —C(=NR$^E$)NHR$^F$; $R^B$, $R^C$, $R^D$, $R^E$, $R^F$, U and V have the same meanings as defined above, can be prepared according to the procedures of the following processes 51 to 55:

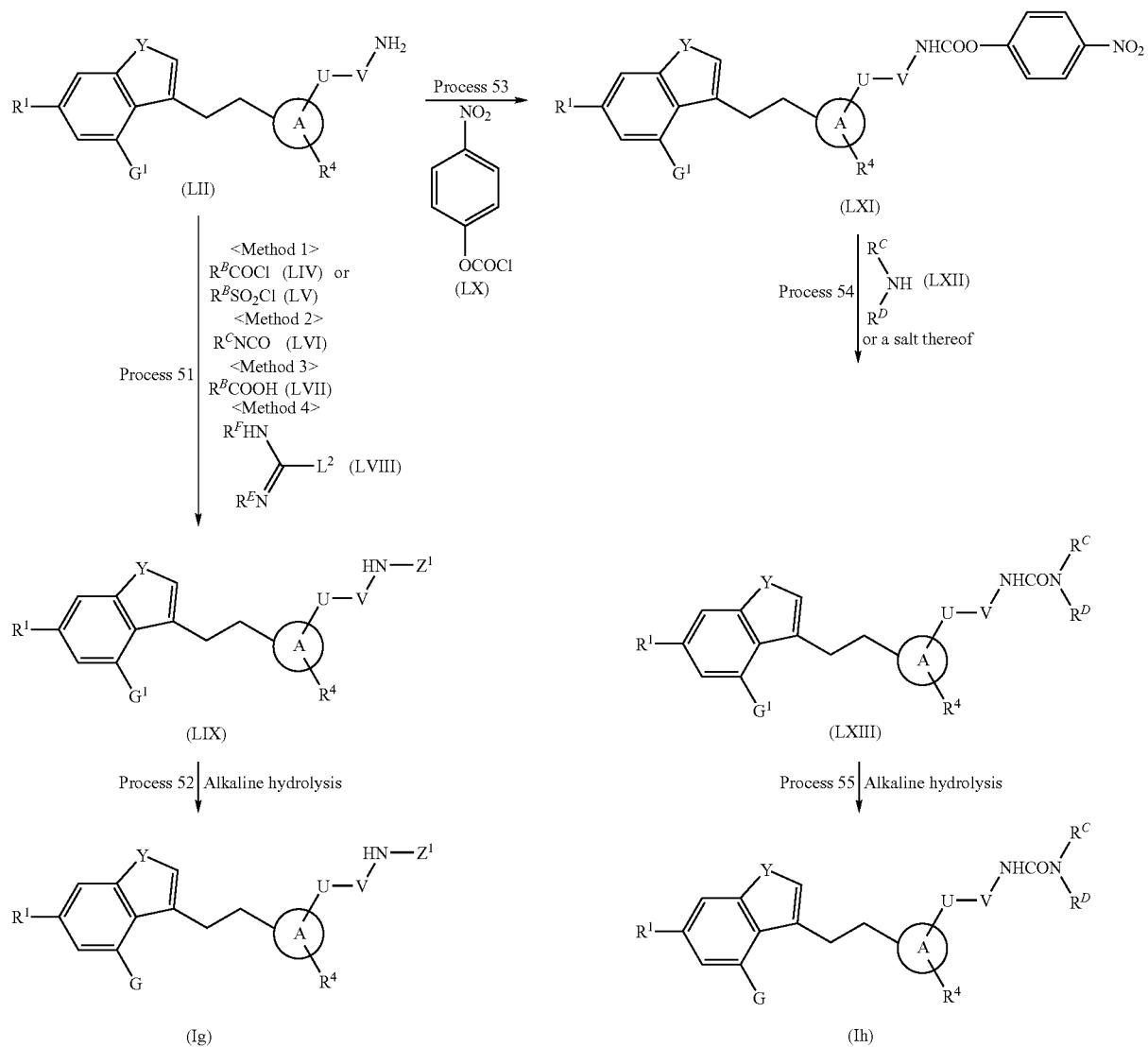

wherein L represents a leaving group such as a pyrazolyl group, a methylthio group, a benzotriazolyl group or the like; and $R^1$, $R^4$, $R^B$, $R^C$, $R^D$, $R^E$, $R^F$, G, $G^1$, U, V, Y, $Z^1$ and ring A have the same meanings as defined above, and with the proviso that a compound having a protective group can be optionally used when a hydroxy group, an amino group and/or a carboxy group exists in each compound.

Process 51

A compounds represented by the above general formula (LIX) can be prepared from a compound represented by the above general formula (LII) according to the following methods 1 to 4.

<Method 1>

A compound represented by the above general formula (LII) is allowed to react with an acid chloride represented by the above general formula (LIV) or (LV) in the presence of a base such as triethylamine, N,N-diisopropylethylamine, pyridine, 1,8-diazabicyclo[5.4.0]undec-7-ene or the like in an inert solvent such as dichloromethane, ethyl acetate, tetrahydrofuran, pyridine, acetonitrile or a mixed solvent thereof at usually 0° C. to reflux temperature for usually 30 minutes to 1 day.

<Method 2>

A compound represented by the above general formula (LII) is allowed to react with an isocyanate compound represented by the above general formula (LVI) in the presence or absence of a base such as triethylamine, N,N-diisopropylethylamine, pyridine, 1,8-diazabicyclo[5.4.0]undec-7-ene or the like in an inert solvent such as dichloromethane, ethyl acetate, tetrahydrofuran, pyridine, acetonitrile, toluene or a mixed solvent thereof at usually 0° C. to reflux temperature for usually 30 minutes to 1 day.

<Method 3>

A compound represented by the above general formula (LII) is allowed to react with a carboxylic acid compound represented by the above general formula (LVII) after suitably adding 1-hydroxybenzotriazole as occasion demands in the presence of a condensing agent such as 1-ethyl-3-(3-dimethylaminopropyl)carbodiimide hydrochloride, dicyclohexylcarbodiimide or the like and in the presence or absence of abase such as triethylamine, N,N-diisopropylethylamine or the like in an inert solvent such as N,N-dimethylformamide, dichloromethane or a mixed solvent thereof at usually 0° C. to reflux temperature for usually 1 hour to 3 days.

<Method 4>

A compound represented by the above general formula (LII) is allowed to react with a guanidylating reagent represented by the above general formula (LVIII) such as N-(benzyloxycarbonyl)-1H-pyrazol-1-carboxamidine or the like in an inert solvent such as tetrahydrofuran, methanol, ethanol, toluene or a mixed solvent thereof at usually room temperature to reflux temperature for usually 1 hour to 5 days.

Process 52

A compound represented by the above general formula (Ig) of the present invention can be prepared by subjecting a compound represented by the above general formula (LIX) to alkaline hydrolysis. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature.

Process 53

An activated ester compound represented by the above general formula (LXI) can be prepared by condensing a compound represented by the above general formula (LII) with an agent for making an activated ester represented by the above formula (LX) in the presence of a base such as triethylamine, N,N-diisopropylethylamine, pyridine or 1,8-diazabicyclo-[5.4.0]undec-7-ene in an inert solvent. As the solvent used in the condensing reaction, for example, dichloromethane, tetrahydrofuran, ethyl acetate, acetonitrile, pyridine, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 54

A compound represented by the above general formula (LXIII) can be prepared by condensing a compound represented by the above general formula (LXI) with an amine compound represented by the above general formula (LXII) or a salt thereof in the presence or absence of a base such as triethylamine, N,N-diisopropylethylamine, pyridine, 1,8-diazabicyclo-[5.4.0]undec-7-ene, sodium hydride, potassium tert-butoxide, potassium carbonate or cesium carbonate in an inert solvent. As the solvent used in the condensing reaction, for example, dichloromethane, methanol, ethanol, tetrahydrofuran, ethyl acetate, acetonitrile, pyridine, N,N-dimethylformamide, a mixed solvent thereof and the like can be illustrated. The reaction temperature is usually from room temperature to reflux temperature, and the reaction time is usually from 30 minutes to 2 days, varying based on a used starting material, solvent and reaction temperature.

Process 55

A compound represented by the above general formula (Ih) of the present invention can be prepared by subjecting a compound represented by the above general formula (LXIII) to alkaline hydrolysis. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature.

Of the compounds represented by the above general formula (I) of the present invention, a compound wherein $R^2$ represents a hydrogen atom; Q represents an ethylene group; and $R^3$ represents —U—V—C(=O)N($R^5$)—$R^A$ (in which $R^5$, $R^A$, U and V have the same meanings as defined above) can be also prepared according to the procedures of the following processes 56 to 58:

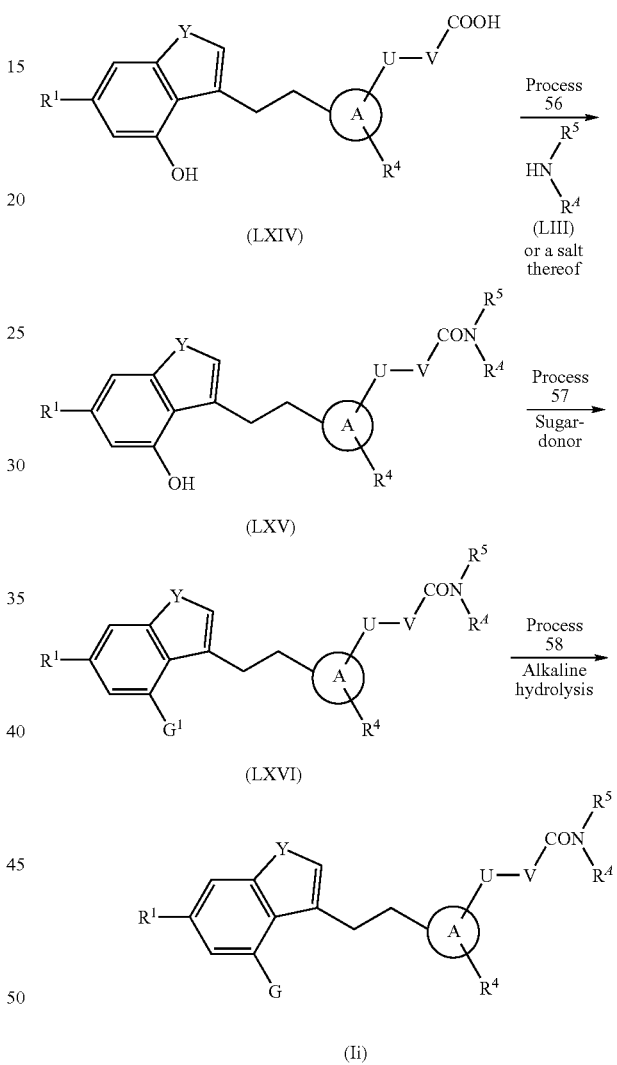

wherein $R^1$, $R^4$, $R^5$, $R^A$, G, $G^1$, U, V, Y and ring A have the same meanings as defined above, and with the proviso that a compound having a protective group can be optionally used when a hydroxy group, an amino group and/or a carboxy group exists in each compound.

Process 56

A compound represented by the above general formula (LXV) can be prepared by subjecting a compound represented by the above general formula (LXIV) to condensation with an amine derivative represented by the above general formula (LIII) by suitably adding 1-hydroxybenzotriazole as occasion demands in the presence or absence of a condensing agent such as 1-ethyl-3-(3-dimethylaminopropyl)carbodiimide hydrochloride, dicyclohexylcarbodiimide or the like and a base such as triethylamine, N,N-diisopropylethylamine or the like in an inert solvent. As the solvent used in the condensation, for example, N,N-dimethylformamide, tetrahydrofuran, dichloromethane or a mixed solvent thereof and the like can be illustrated. The reaction temperature is usually from 0° C. to reflux temperature, and the reaction time is usually from 1 hour to 3 days, varying based on a used starting material, solvent and reaction temperature.

Process 57

A glycoside compound represented by the above general formula (LXVI) can be prepared by subjecting a compound represented by the above general formula (LXV) to glycosidation using a sugar donor compound such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide, 2,3,4,6-tetra-O-acetyl-1-O-trichloroacetoimidoyl-α-D-galactopyranose, 2,3,4,6-tetra-O-acetyl-1-O-trichloroacetoimidoyl-β-D-galactopyranose, 1,2,3,4,6-penta-O-acetyl-β-D-galactopyranose, 2,3,4,6-tetra-O-pivaloyl-1-O-trichloroacetoimidoyl-α-D-glucopyranose, 2,3,4,6-tetra-O-pivaloyl-1-O-trichloroacetoimidoyl-β-D-glucopyranose, 2,3,4,6-tetra-O-pivaloyl-1-O-trichloroacetoimidoyl-α-D-galactopyranose, 2,3,4,6-tetra-O-pivaloyl-1-O-trichloroacetoimidoyl-β-D-galactopyranose, 2,3,4,6-tetra-O-benzoyl-1-O-trichloroacetoimidoyl-α-D-glucopyranose, 2,3,4,6-tetra-O-benzoyl-1-O-trichloroacetoimidoyl-β-D-glucopyranose, 2,3,4,6-tetra-O-benzoyl-1-O-trichloroacetoimidoyl-α-D-galactopyranose, 2,3,4,6-tetra-O-benzoyl-1-O-trichloroacetoimidoyl-β-D-galactopyranose or the like in the presence of an activating reagent such as boron trifluoride-diethyl ether complex, silver trifluoromethanesulfonate, tin (IV) chloride, trimethylsilyl trifluoromethanesulfonate or the like in an inert solvent. As the solvent used, for example, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 58

A compound represented by the above general formula (Ii) of the present invention can be prepared by subjecting a glycoside compound represented by the above general formula (LXVI) to alkaline hydrolysis. As the solvent used, for example, water, methanol, ethanol, tetrahydrofuran, a mixed solvent thereof and the like can be illustrated. As the base, for example, sodium hydroxide, sodium methoxide, sodium ethoxide and the like can be illustrated. The reaction temperature is usually from 0° C. to reflux temperature, and the reaction time is usually from 30 minutes to 6 hours, varying based on a used starting material, solvent and reaction temperature.

Of the compounds represented by the above general formula (I) of the present invention, a compound wherein $R^2$ represents a hydrogen atom; Q represents an ethylene group; and $R^3$ represents —CH═CH—$V^2$—$W^1$—N($R^5$)—$R^A$ or —$CH_2CH_2$—$V^2$—$W^1$—N($R^5$)—$R^A$ (in which $V^2$ represents a $C_{1-4}$ alkylene group which may have a hydroxy group, $C_{2-4}$ alkenylene group or a single bond; $W^1$ represents —CO— or —$SO_2$—; $R^5$ and $R^A$ have the same meanings as defined above) can be also prepared according to the procedures of the following processes 59 to 65:

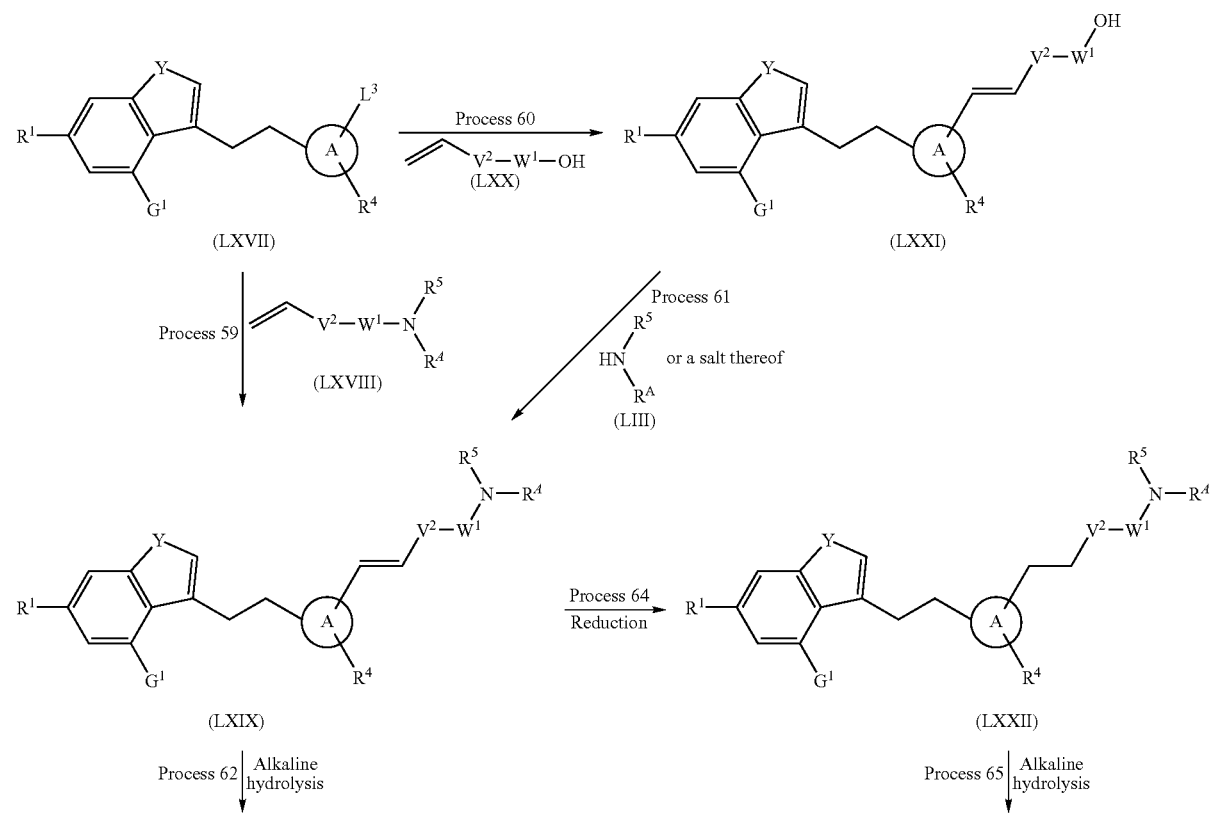

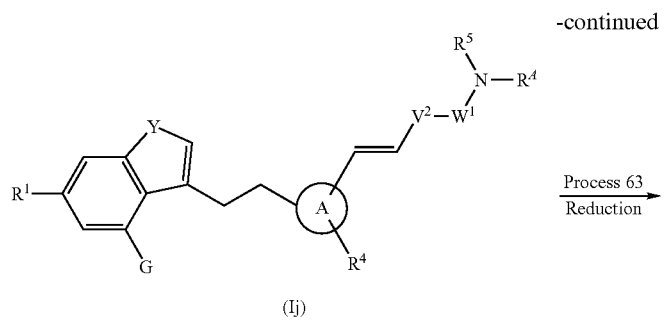

(Ij)

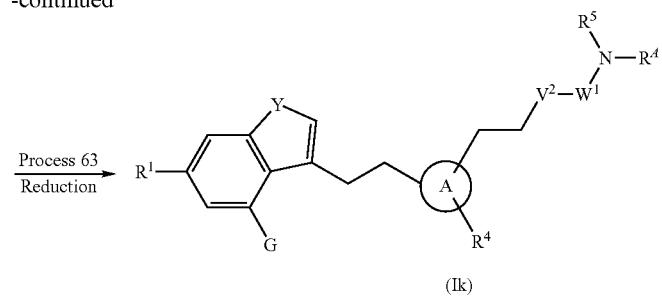

(Ik)

wherein $L^3$ represents a chloride atom, a bromine atom, a iodine atom or a trifluoromethanesulfonyloxy group; $R^1$, $R^4$, $R^5$, $R^4$, G, $G^1$, $V^2$, $W^1$, Y and ring A have the same meanings as defined above, and with the proviso that a compound having a protective group can be optionally used when a hydroxy group, an amino group and/or a carboxy group exists in each compound.

Process 59

A compound represented by the above general formula (LXIX) can be prepared by subjecting a compound represented by the above general formula (LXVII) to Heck reaction with an olefin derivative represented by the above general formula (LXVIII) by using a palladium catalyst such as palladium-carbon powder, palladium acetate, tetrakis(triphenylphosphine)palladium, dibenzylideneacetone palladium, bis(triphenylphosphine)palladium dichloride or the like in the presence or absence of a phosphine ligand such as tris(2-methylphenyl)phosphine, triphenylphosphine or the like and in the presence of a base such as triethylamine, sodium tert-butoxide, potassium tert-butoxide, cesium fluoride or the like in an inert solvent. As the solvent used, for example, acetonitrile, toluene, tetrahydrofuran, triethylamine, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 60

An olefin derivative represented by the above general formula (LXXI) can be prepared by subjecting a compound represented by the above general formula (LXVII) to Heck reaction with an olefin derivative represented by the above general formula (LXX) by using a palladium catalyst such as palladium-carbon powder, palladium acetate, tetrakis(triphenylphosphine)palladium, dibenzylideneacetone palladium, bis(triphenylphosphine)palladium dichloride or the like in the presence or absence of a phosphine ligand such as tris(2-methylphenyl)phosphine, triphenylphosphine or the like and in the presence of a base such as triethylamine, sodium tert-butoxide, potassium tert-butoxide, cesium fluoride or the like in an inert solvent. As the solvent used in the reaction, for example, acetonitrile, toluene, tetrahydrofuran, triethylamine, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 61

A compound represented by the above general formula (LXIX) can be prepared by subjecting a compound represented by the above general formula (LXXI) to condensation with an amine derivative represented by the above general formula (LIII) by suitably adding 1-hydroxybenzotriazole as occasion demands in the presence or absence of a condensing agent such as 1-ethyl-3-(3-dimethylaminopropyl)carbodiimide hydrochloride, dicyclohexylcarbodiimide or the like and a base such as triethylamine, N,N-diisopropylethylamine or the like in an inert solvent. As the solvent used in the condensation, for example, N,N-dimethylformamide, tetrahydrofuran, dichloromethane, a mixed solvent thereof and the like can be illustrated. The reaction temperature is usually from 0° C. to reflux temperature, and the reaction time is usually from 1 hour to 3 days, varying based on a used starting material, solvent and reaction temperature.

Process 62

A compound represented by the above general formula (Ij) of the present invention can be prepared by subjecting a compound represented by the above general formula (LXIX) to alkaline hydrolysis to remove a protective group. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide and the like can be illustrated. The reaction temperature is usually from 0° C. to reflux temperature, and the reaction time is usually from 30 minutes to 1 day, varying based on a used starting material, solvent and reaction temperature.

Process 63

A compound represented by the above general formula (Ik) of the present invention can be prepared by subjecting a compound represented by the above general formula (Ij) to catalytic hydrogenation using a palladium catalyst such as palladium-carbon powder in an inert solvent. As the solvent used in the catalytic hydrogenation, for example, methanol, ethanol, tetrahydrofuran, ethyl acetate, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 64

A compound represented by the above general formula (LXXII) can be prepared by subjecting a compound represented by the above general formula (LXIX) to catalytic hydrogenation using a palladium catalyst such as palladium-carbon powder in an inert solvent. As the solvent used in the catalytic hydrogenation, for example, methanol, ethanol, tetrahydrofuran, ethyl acetate, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 65

A compound represented by the above general formula (Ik) of the present invention can be prepared by subjecting a compound represented by the above general formula (LXXII) to alkaline hydrolysis to remove a protective group. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide and the like can be illustrated. The reaction temperature is usually from 0° C. to reflux temperature, and the reaction time is usually from 30 minutes to 1 day, varying based on a used starting material, solvent and reaction temperature.

In case of compounds having a hydroxy group, an amino group and/or a carboxy group in the above procedures, they can be also used in each reaction after introducing any protective group in the usual way as occasion demand. The protective group can be optionally removed in any subsequent reaction in the usual way.

The compounds represented by the above general formula (I) of the present invention obtained by the above production processes can be isolated and purified by conventional separation means such as fractional recrystallization, purification using chromatography, solvent extraction and solid phase extraction.

The fused heterocyclic derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris(hydroxymethyl)aminomethane, arginine, lysine and the like.

The compounds represented by the above general formula (I) of the present invention include their solvates with pharmaceutically acceptable solvents such as ethanol and water.

Of the fused heterocyclic derivatives represented by the above general formula (I) of the present invention and the prodrugs thereof, there are two geometrical isomers, cis(Z)-isomer and trans(E)-isomer, in each compound having an unsaturated bond. In the present invention, either of the isomers can be employed.

Of the fused heterocyclic derivatives represented by the above general formula (I) of the present invention and the prodrugs thereof, there are two optical isomers, R-isomer and S-isomer, in each compound having an asymmetric carbon atom excluding the glucopyranosyloxy moiety or the galactopyranosyloxy moiety. In the present invention, either of the isomers can be employed, and a mixture of both isomers can be also employed.

A prodrug of a compound represented by the above general formula (I) of the present invention can be prepared by introducing an appropriate group forming a prodrug into any one or more groups selected from a hydroxy group and an amino group of the compound represented by the above general formula (I) using a corresponding reagent to produce a prodrug such as a halide compound or the like in the usual way, and then by suitably isolating and purifying in the usual way as occasion demands. As a group forming a prodrug used in a hydroxy group or an amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group or the like can be illustrated. The term "$C_{1-6}$ alkoxy-substituted ($C_{2-7}$ acyl) group" means the above $C_{2-7}$ acyl group substituted by the above $C_{1-6}$ alkoxy group; the term "$C_{2-7}$ alkoxycarbonyl-substituted ($C_{2-7}$ acyl) group" means the above $C_{2-7}$ acyl group substituted by the above $C_{2-7}$ alkoxycarbonyl group; the term "$C_{1-6}$ alkoxy-substituted ($C_{2-7}$ alkoxycarbonyl) group" means the above $C_{2-7}$ alkoxycarbonyl group substituted by the above $C_{1-6}$ alkoxy group. In addition, as a group forming a prodrug, a glucopyranosyl group or a galactopyranosyl group can be illustrated. For example, these groups are preferably introduced into the hydroxy group at the 4 or 6 position of the glucopyranosyloxy group or the galactopyranosyloxy group, and are more preferably introduced into the hydroxy group at the 4 or 6 position of the glucopyranosyloxy group.

The fused heterocyclic derivatives represented by the above general formula (I) of the present invention, for example, showed a potent inhibitory activity on human SGLT1 or SGLT2 in a human SGLT1 or SGLT2 inhibitory activity confirmatory test as described below. Therefore, a fused heterocyclic derivative represented by the above general formula (I) of the present invention can exert an excellent inhibitory activity of SGLT1 at the small intestine or an excellent inhibitory activity of SGLT2 at the kidney, and significantly inhibit blood glucose level increase or significantly lower blood glucose level. Therefore, a fused heterocyclic derivative represented by the above general formula (I) of the present invention, a pharmaceutically acceptable salt and a prodrug thereof is extremely useful as an agent for the inhibition of hyperglycemia, the inhibition of advancing into diabetes in a subject with impaired glucose tolerance and the prevention or treatment of a disease associated with hyperglycemia such as diabetes, impaired glucose tolerance (IGT), diabetic complications (e.g., retinopathy, neuropathy, nephropathy, ulcer, macroangiopathy), obesity, hyperinsulinemia, hyperlipidemia, hypercholesterolemia, hypertriglyceridemia, lipid metabolism disorder, atherosclerosis, hypertension, congestive heart failure, edema, hyperuricemia, gout or the like, which relates to SGLT1 activity at the small intestine and SGLT2 activity at the kidney.

Furthermore, the compounds of the present invention can be suitably used in combination with at least one member selected from drugs. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, for example, α-glucosidase inhibitors such as a carbose, voglibose, miglitol, CKD-711, emiglitate, MDL-25,637, camiglibose and MDL-73,945, α-amylase inhibitors such as AZM-127, SGLT1 inhibitors described in pamphlets of International Publication Nos. WO02/098893, WO2004/014932, WO2004/018491, WO2004/019958 and the like are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers are used preferably for diabetes, impaired glucose tolerance or diabetic complications, and more preferably for diabetes or impaired glucose tolerance because of lowering blood glucose level by acting on pancreatic β-cells and enhancing the insulin secretion.

As SGLT2 inhibitors, T-1095 and compounds described in Japanese patent publications Nos. Hei10-237089 and 2001-288178, and International Publications Nos. WO01/16147, WO01/27128, WO01/68660, WO01/74834, WO01/74835, WO02/28872, WO02/36602, WO02/44192, WO02/53573, WO03/000712, WO03/020737 and the like are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at the kidney's proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP- 112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors are preferably used for diabetic complications because of inhibiting formation of advanced glycation endproducts which are accelerated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelerated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecamine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As antidiarrhoics or cathartics, polycarbophil calcium, albumin tannate, bismuth subnitrate or the like are illustrated. These drugs are preferably used for diarrhea, constipation or the like accompanying diabetes or the like.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856, TAK-475 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal trigyceride transfer protein inhibitors, lipoxygenase inhibitors and low-density lipoprotein receptor enhancers are preferably used for hyperlipidemia, hypercholesterolemia, hypertriglyceridemia or lipidmetabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, roliprarn, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as $\gamma$-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidaprilhydrochloride, benazeprilhydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-$\alpha$, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with drugs, for example, in the use for diabetes, the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a biguanide, an insulin secretion enhancer, a SGLT2 inhibitor and an insulin or insulin analogue is most preferable. Similarly, in the use for diabetic complications, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered. The pharmaceutical compositions of the present invention also include sustained release formulation including gastrointestinal mucoadhesive formulation (e.g., International publications Nos. WO99/10010, WO99/26606, and Japanese patent publication No. 2001-2567).

These pharmaceutical compositions can be prepared by admixing with or by diluting and dissolving with an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional methods. In case of the uses of the compound of the present invention in combination with the drug(s), they can be prepared by formulating each active ingredient together or individually.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with the drug(s), the dosage of the compound of the present invention can be decreased, depending on the dosage of the drug(s).

EXAMPLES

The present invention is further illustrated in more detail by way of the following Reference Examples, Examples and Test Examples. However, the present invention is not limited thereto.

Reference Example 1

2'-Benzyloxy-6'-hydroxyacetophenone

To a mixture of 2',6'-dihydroxyacetophenone (4 g) and potassium carbonate (3.82 g) in acetone (40 mL) was added benzyl bromide (3.13 mL), and the mixture was stirred at room temperature overnight. The reaction mixture was poured into water, and the precipitated crystals were collected by filtration. The crystals were washed with water and n-hexane, and dried under reduced pressure to give the title compound (3.67 g).

$^1$H-NMR (CDCl$_3$) δ ppm: 2.62 (3H, s), 5.13 (2H, s), 6.45-6.5 (1H, m), 6.55-6.65 (1H, m), 7.3-7.5 (6H, m), 13.22 (1H, s)

Reference Example 2

2'-Benzyloxy-6'-hydroxy-4-methylchalcone

To a suspension of 2'-benzyloxy-6'-hydroxyacetophenone (0.5 g) in ethanol (10 mL)-water (3 mL) was added potassium hydroxide (1.39 g), and the mixture was stirred at room temperature for 10 minutes. To the reaction mixture was added p-tolualdehyde (0.37 mL), and the mixture was stirred at room temperature for 45 minutes. The reaction mixture was acidified by addition of 2 mol/L hydrochloric acid (12.5 mL), and the precipitated crystals were collected by filtration. The crystals were washed with water and dried under reduced pressure to give the title compound (0.69 g).

$^1$H-NMR (CDCl$_3$) δ ppm: 2.35 (3H, s), 5.13 (2H, s), 6.5-6.6 (1H, m), 6.6-6.7 (1H, m), 7.0-7.1 (4H, m), 7.25-7.55 (6H, m), 7.75 (1H, d, J=15.7 Hz), 7.86 (1H, d, J=15.7 Hz), 13.53 (1H, s)

Reference Example 3

2'-Benzyloxy-6'-hydroxychalcone

The title compound was prepared in a similar manner to that described in Reference Example 2 using benzaldehyde instead of p-tolualdehyde.

$^1$H-NMR (CDCl$_3$) δ ppm: 5.13 (2H, s), 6.55 (1H, d, J=8.1 Hz), 6.66 (1H, d, J=8.2 Hz), 7.1-7.15 (2H, m), 7.15-7.45 (7H, m), 7.45-7.55 (2H, m), 7.75 (1H, d, J=15.8 Hz), 7.88 (1H, d, J=15.8 Hz), 13.48 (1H, s)

Reference Example 4

2'-Benzyloxy-6'-hydroxy-2-methylchalcone

The title compound was prepared in a similar manner to that described in Reference Example 2 using o-tolualdehyde instead of p-tolualdehyde.

$^1$H-NMR (CDCl$_3$) δ ppm: 2.42 (3H, s), 5.13 (2H, s), 6.55 (1H, dd, J=8.2 Hz, 0.8 Hz), 6.66 (1H, dd, J=8.4 Hz, 0.8 Hz), 6.85-7.0 (2H, m), 7.1-7.25 (2H, m), 7.3-7.45 (4H, m), 7.45-7.5 (2H, m), 7.8 (1H, d, J=15.4 Hz), 8.06 (1H, d, J=15.4 Hz), 13.4 (1H, s)

Reference Example 5

2'-Benzyloxy-6'-hydroxy-3-methylchalcone

The title compound was prepared in a similar manner to that described in Reference Example 2 using m-tolualdehyde instead of p-tolualdehyde.

$^1$H-NMR (CDCl$_3$) δ ppm: 2.27 (3H, s), 5.15 (2H, s), 6.55 (1H, d, J=8.2 Hz, 1.0 Hz), 6.65 (1H, d, J=8.4 Hz, 1.0 Hz), 6.9-7.0 (1H, m), 7.05-7.2 (3H, m), 7.3-7.45 (4H, m), 7.45-7.5 (2H, m), 7.74 (1H, d, J=15.3 Hz), 7.87 (1H, d, J=15.3 Hz), 13.4 (1H, s)

Reference Example 6

6'-Hydroxy-2'-methoxycarbonylmethoxy-4-methyldihydrochalcone

To a solution of 2'-benzyloxy-6'-hydroxy-4-methylchalcone (0.69 g) in acetone (10 mL)-N,N-dimethylformamide (10 mL) were added potassium carbonate (0.41 g) and methyl bromoacetate (0.21 mL), and the mixture was stirred at room temperature overnight. The reaction mixture was poured into water, and the resulting mixture was extracted with diethyl ether. The extract was washed with water and dried over anhydrous magnesium sulfate, and the solvent was removed under reduced pressure. The residue was dissolved in methanol (10 mL). To the solution was added 10% palladium-carbon powder (0.29 g), and the mixture was stirred at room temperature under a hydrogen atmosphere for 5 hours. Dichloromethane was added to the mixture, and the insoluble material was removed by filtration. The filtrate was concentrated under reduced pressure to give the title compound (0.58 g).

$^1$H-NMR (CDCl$_3$) δ ppm: 2.32 (3H, s), 2.95-3.05 (2H, m), 3.5-3.6 (2H, m), 3.69 (3H, s), 4.68 (2H, s), 6.22 (1H, d, J=8.4 Hz), 6.63 (1H, d, J=8.4 Hz), 7.1 (2H, d, J=8.2 Hz), 7.15 (2H, d, J=8.2 Hz), 7.31 (1H, t, J=8.4 Hz), 13.18 (1H, s)

Reference Example 7

6'-Hydroxy-2'-(methoxycarbonylmethoxy)dihydrochalcone

The title compound was prepared in a similar manner to that described in Reference Example 6 using 2'-benzyloxy-6'-hydroxychalcone instead of 2'-benzyloxy-6'-hydroxy-4-methylchalcone.

$^1$H-NMR (CDCl$_3$) δ ppm: 3.0-3.1 (2H, m), 3.5-3.6 (2H, m), 3.67 (3H, s), 4.68 (2H, s), 6.2-6.25 (1H, m), 6.64 (1H, dd, J=8.2 Hz, 1.0 Hz), 7.15-7.35 (6H, m), 13.18 (1H, s)

Reference Example 8

6'-Hydroxy-2'-methoxycarbonylmethoxy-2-methyldihydrochalcone

The title compound was prepared in a similar manner to that described in Reference Example 6 using 2'-benzyloxy-6'-hydroxy-2-methylchalcone instead of 2'-benzyloxy-6'-hydroxy-4-methylchalcone.

$^1$H-NMR (CDCl$_3$) δ ppm: 2.35 (3H, s), 3.0-3.05 (2H, m), 3.45-3.55 (2H, m), 3.63 (3H, s), 4.67 (2H, s), 6.23 (1H, d, J=8.4 Hz), 6.64 (1H, d, J=8.4 Hz), 7.05-7.25 (4H, m), 7.32 (1H, t, J=8.4 Hz), 13.21 (1H, s)

Reference Example 9.

6'-Hydroxy-2'-methoxycarbonylmethoxy-3-methyldihydrochalcone

The title compound was prepared in a similar manner to that described in Reference Example 6 using 2'-benzyloxy-6'-hydroxy-3-methylchalcone instead of 2'-benzyloxy-6'-hydroxy-4-methylchalcone.
$^1$H-NMR (CDCl$_3$) δ ppm: 2.33 (3H, s), 2.95-3.05 (2H, m), 3.5-3.6 (2H, m), 3.68 (3H, s), 4.68 (2H, s), 6.23 (1H, d, J=8.4 Hz), 6.64 (1H, d, J=8.4 Hz), 6.95-7.1 (3H, m), 7.18 (1H, t, J=7.7 Hz), 7.31 (1H, t, J=8.4 Hz), 13.19 (1H, s)

Reference Example 10

4-Hydroxy-3-[2-(4-methylphenyl)ethyl]benzofuran

To a solution of 6'-hydroxy-2'-methoxycarbonylmethoxy-4-methyldihydrochalcone (0.58 g) in methanol (10 mL) was added sodium methoxide (28% methanol solution, 0.68 mL), and the mixture was heated for reflux overnight. The reaction mixture was cooled to room temperature and poured into 1 mol/L hydrochloric acid. The resulting mixture was extracted with ethyl acetate, and the extract was washed with water and dried over anhydrous magnesium sulfate. The solvent was removed under reduced pressure, and the residue was purified by column chromatography on silica gel (eluent: n-hexane/ethyl acetate=5/1) to give the title compound (0.13 g).
$^1$H-NMR (CDCl$_3$) δ ppm: 2.32 (3H, s), 2.95-3.1 (4H, m), 4.98 (1H, s), 6.54 (1H, dd, J=7.5 Hz, 0.8 Hz), 7.0-7.15 (6H, m), 7.22 (1H, s)

Reference Example 11

4-Hydroxy-3-(2-phenylethyl)benzofuran

The title compound was prepared in a similar manner to that described in Reference Example 10 using 6'-hydroxy-2'-(methoxycarbonylmethoxy)dihydrochalcone instead of 6'-hydroxy-2'-methoxycarbonylmethoxy-4-methyldihydrochalcone.
$^1$H-NMR (CDCl$_3$) δ ppm: 3.0-3.15 (4H, m), 5.09 (1H, s), 6.54 (1H, dd, J=7.6 Hz, 1.1 Hz), 7.0-7.15 (2H, m), 7.15-7.35 (6H, m)

Reference Example 12

4-Hydroxy-3-[2-(2-methylphenyl)ethyl]benzofuran

The title compound was prepared in a similar manner to that described in Reference Example 10 using 6'-hydroxy-2'-methoxycarbonylmethoxy-2-methyldihydrochalcone instead of 6'-hydroxy-2'-methoxycarbonylmethoxy-4-methyldihydrochalcone.
$^1$H-NMR (CDCl$_3$) δ ppm: 2.34 (3H, s), 3.0-3.1 (4H, m), 5.0 (1H, s), 6.55 (1H, dd, J=7.4 Hz, 0.9 Hz), 7.0-7.25 (6H, m), 7.27 (1H, s)

Reference Example 13

4-Hydroxy-3-[2-(3-methylphenyl)ethyl]benzofuran

The title compound was prepared in a similar manner to that described in Reference Example 10 using 6'-hydroxy-2'-methoxycarbonylmethoxy-3-methyldihydrochalcone instead of 6'-hydroxy-2'-methoxycarbonylmethoxy-4-methyldihydrochalcone.
$^1$H-NMR (CDCl$_3$) δ ppm: 2.33 (3H, s), 2.95-3.05 (2H, m), 3.05-3.15 (2H, m), 5.01 (1H, s), 6.54 (1H, dd, J=7.4 Hz, 0.9 Hz), 6.95-7.15 (5H, m), 7.18 (1H, t, J=7.4 Hz), 7.24 (1H, s)

Example 1

4-(β-D-Glucopyranosyloxy)-3-[2-(4-methylphenyl)ethyl]-benzofuran

To a solution of 4-hydroxy-3-[2-(4-methylphenyl)ethyl]-benzofuran (0.13 g) and 2,3,4,6-tetra-O-acetyl-1-O-trichloroacetoimidoyl-α-D-glucopyranose (0.27 g) in dichloromethane (5 mL) was added boron trifluoride-diethyl ether complex (0.069 mL), and the mixture was stirred at room temperature for 30 minutes. The reaction mixture was purified by column chromatography on silica gel (eluent: n-hexane/ethyl acetate=3/1-3/2) to give 4-(2,3,4,6-tetra-O-acetyl-β-D-glucopyranosyloxy)-3-[2-(4-methylphenyl)ethyl] benzofuran (0.25 g). This material was dissolved in methanol (4 mL). To the solution was added sodium methoxide (28% methanol solution, 0.082 mL), and the mixture was stirred at room temperature for 1 hour. The reaction mixture was concentrated under reduced pressure, and the residue was purified by column chromatography on silica gel (eluent: dichloromethane/methanol=10/1) to give the title compound (0.14 g).
$^1$H-NMR (CD$_3$OD) δ ppm: 2.28 (3H, s), 2.85-3.1 (3H, m), 3.1-3.25 (1H, m), 3.35-3.45 (1H, m), 3.45-3.65 (3H, m), 3.71 (1H, dd, J=12.0 Hz, 5.6 Hz), 3.9 (1H, dd, J=12.0 Hz, 2.1 Hz), 5.18 (1H, d, J=7.8 Hz), 6.95 (1H, d, J=8.2 Hz), 7.0-7.15 (5H, m), 7.18 (1H, t, J=8.2 Hz), 7.25 (1H, s)

Example 2

4-(β-D-Glucopyranosyloxy)-3-(2-phenylethyl)benzofuran

The title compound was prepared in a similar manner to that described in Example 1 using 4-hydroxy-3-(2-phenylethyl)benzofuran instead of 4-hydroxy-3-[2-(4-methylphenyl)ethyl]benzofuran.
$^1$H-NMR (CD$_3$OD) δ ppm: 2.9-3.15 (3H, m), 3.15-3.25 (1H, m), 3.35-3.55 (3H, m), 3.55-3.65 (1H, m), 3.71 (1H, dd, J=12.0 Hz, 5.4 Hz), 3.9 (1H, dd, J=12.0 Hz, 2.4 Hz), 5.19 (1H, d, J=8.1 Hz), 6.96 (1H, d, J=8.1 Hz), 7.05-7.3 (8H, m)

Example 3

4-(β-D-Glucopyranosyloxy)-3-[2-(2-methylphenyl)ethyl]-benzofuran

The title compound was prepared in a similar manner to that described in Example 1 using 4-hydroxy-3-[2-(2-methylphenyl)ethyl]benzofuran instead of 4-hydroxy-3-[2-(4-methylphenyl)ethyl]benzofuran.
$^1$H-NMR (CD$_3$OD) δ ppm: 2.27 (3H, s), 2.9-3.25 (4H, m), 3.35-3.45 (1H, m), 3.45-3.6 (3H, m), 3.71 (1H, dd, J=12.2 Hz, 5.9 Hz), 3.91 (1H, dd, J=12.2 Hz, 2.2 Hz), 5.18 (1H, d, J=7.9 Hz), 6.97 (1H, d, J=8.2 Hz), 7.0-7.15 (5H, m), 7.19 (1H, t, J=8.2 Hz), 7.24 (1H, s)

Example 4

4-(β-D-Glucopyranosyloxy)-3-[2-(3-methylphenyl)ethyl]-benzofuran

The title compound was prepared in a similar manner to that described in Example 1 using 4-hydroxy-3-[2-(3-methylphenyl)ethyl]benzofuran instead of 4-hydroxy-3-[2-(4-methylphenyl)ethyl]benzofuran.

$^1$H-NMR (CD$_3$OD) δ ppm: 2.29 (3H, s), 2.85-3.1 (3H, m), 3.1-3.25 (1H, m), 3.35-3.55 (3H, m), 3.55-3.65 (1H, m), 3.71 (1H, dd, J=12.0 Hz, 5.6 Hz), 3.9 (1H, dd, J=12.0 Hz, 2.3 Hz), 5.19 (1H, d, J=7.8 Hz), 6.9-7.15 (6H, m), 7.18 (1H, t, J=8.2 Hz), 7.26 (1H, s)

Example 5

4-(β-D-Galactopyranosyloxy)-3-(2-phenylethyl)benzofuran

To a solution of 4-hydroxy-3-(2-phenylethyl)benzofuran (0.11 g) and 1,2,3,4,6-penta-O-acetyl-β-D-galactopyranose (0.37 g) in dichloromethane (5 mL) was added boron trifluoride-diethyl ether complex (0.12 mL), and the mixture was stirred at room temperature overnight. The reaction mixture was purified by column chromatography on silica gel (eluent: n-hexane/ethyl acetate=3/1-3/2) to give 4-(2,3,4,6-tetra-O-acetyl-β-D-galactopyranosyloxy)-3-(2-phenylethyl)benzofuran (0.13 g). This material was dissolved in methanol (5 mL). To the solution was added sodium methoxide (28% methanol solution, 0.043 mL), and the mixture was stirred at room temperature for 30 minutes. The reaction mixture was concentrated under reduced pressure, and the residue was purified by column chromatography on silica gel (eluent: dichloromethane/methanol=10/1) to give the title compound (24 mg).

$^1$H-NMR (CD$_3$OD) δ ppm: 2.95-3.25 (4H, m), 3.62 (1H, dd, J=9.8 Hz, 3.2 Hz), 3.7-3.85 (3H, m), 3.9-4.0 (2H, m), 5.13 (1H, d, J=7.9 Hz), 6.98 (1H, d, J=8.4 Hz), 7.05-7.3 (8H, m)

Reference Example 14

4',6'-Dihydroxy-2'-(methoxycarbonylmethoxy)dihydrochalcone

To a mixture of 2',4',6'-trihydroxyacetophenone monohydrate (5 g) and potassium carbonate (7.42 g) in N,N-dimethylformamide (100 mL) was added benzyl bromide (6.39 mL) under ice-cooling, and the mixture was stirred at room temperature overnight. The reaction mixture was poured into water, and the resulting mixture was extracted with diethyl ether. The extract was washed with water and dried over anhydrous magnesium sulfate. The solvent was removed under reduced pressure, and the residue was purified by column chromatography on silica gel (eluent: n-hexane/ethyl acetate=10/1-5/1) to give 2',4'-dibenzyloxy-6'-hydroxyacetophenone (5.71 g). This material was suspended in ethanol (45 mL)-water (15 mL). To the suspension was added potassium hydroxide (11.0 g), and the mixture was stirred at room temperature for 10 minutes. Benzaldehyde (2.51 mL) was added to the mixture, and the resulting mixture was stirred at room temperature for 15 hours. The reaction mixture was acidified by addition of concentrated hydrochloric acid, and the precipitated crystals were collected by filtration. The crystals were washed with water and dried under reduced pressure to give 2',4'-dibenzyloxy-6'-hydroxychalcone (4.85 g). This material was dissolved in N,N-dimethylformamide (40 mL)-acetone (12 mL). To the solution were added potassium carbonate (2.3 g) and methyl bromoacetate (1.1 mL), and the mixture was stirred at room temperature for 8 hours. The reaction mixture was poured into water, and the resulting mixture was extracted with diethylether. The extract was washed with water and dried over anhydrous magnesium sulfate. The solvent was removed under reduced pressure, and the residue was dissolved in methanol (30 mL). To the solution was added 10% palladium-carbon powder (0.5 g), and the mixture was stirred at room temperature under a hydrogen atmosphere overnight. The insoluble material was removed by filtration, and the filtrate was concentrated under reduced pressure. The residue was purified by column chromatography on silica gel (eluent: n-hexane/ethyl acetate=3/1-2/1) to give the title compound (2.26 g).

$^1$H-NMR (CDCl$_3$) δ ppm: 3.0-3.05 (2H, m), 3.45-3.5 (2H, m), 3.66 (3H, s), 4.63 (2H, s), 5.58 (1H, brs), 5.75 (1H, d, J=2.3 Hz), 6.03 (1H, d, J=2.3 Hz), 7.15-7.35 (5H, m), 13.89 (1H, s)

Reference Example 15

4'-Benzyloxy-6'-hydroxy-2'-(methoxycarbonylmethoxy)dihydrochalcone

To a solution of 4',6'-dihydroxy-2'-(methoxycarbonylmethoxy)dihydrochalcone (0.6 g) in N,N-dimethylformamide (10 mL) were added potassium carbonate (0.26 g) and benzyl bromide (0.22 mL), and the mixture was stirred at room temperature for 3 days. The reaction mixture was poured into water, and the precipitated crystals were collected by filtration and dried under reduced pressure to give the title compound (0.53 g).

$^1$H-NMR (CDCl$_3$) δ ppm: 3.0-3.05 (2H, m), 3.45-3.55 (2H, m), 3.65 (3H, s), 4.61 (2H, s), 5.05 (2H, s), 5.84 (1H, d, J=2.4 Hz), 6.2 (1H, d, J=2.4 Hz), 7.15-7.45 (10H, m), 13.98 (1H, s)

Example 6

4-(2,3,4,6-Tetra-O-acetyl-β-D-glucopyranosyloxy)-6-hydroxy-3-(2-phenylethyl)benzofuran To a solution of 4'-benzyloxy-6'-hydroxy-2'-(methoxycarbonylmethoxy)dihydrochalcone (0.53 g) in methanol (10 mL) was added sodium methoxide (28% methanol solution, 0.72 mL), and the mixture was heated for reflux overnight. The reaction mixture was cooled to room temperature and acidified by addition of 1 mol/L hydrochloric acid. The resulting mixture was extracted with ethyl acetate. The extract was washed with water and dried over anhydrous magnesium sulfate. The solvent was removed under reduced pressure, and the residue was purified by column chromatography on silica gel (eluent: n-hexane/ethyl acetate=5/1-3/1) to give 6-benzyloxy-4-hydroxy-3-(2-phenylethyl)benzofuran (98 mg). This material was dissolved in dichloromethane (5 mL). To the solution were added 2,3,4,6-tetra-O-acetyl-1-O-trichloroacetoimidoyl-α-D-glucopyranose (0.42 g) and boron trifluoride-diethyl ether complex (0.11 mL) successively, and the mixture was stirred at room temperature for 30 minutes. The reaction mixture was purified by column chromatography on silica gel (eluent: n-hexane/ethyl acetate=2/1-3/2) to give 4-(2,3,4,6-tetra-O-acetyl-β-D-glucopyranosyloxy)-6-benzyloxy-3-(2-phenylethyl)benzofuran (0.19 g). This material was dissolved in tetrahydrofuran (5 mL). To the solution was added 10% palladium-carbon powder (21 mg), and the mixture was stirred at room temperature under a hydrogen atmosphere for 1.5 hours. The insoluble material was removed by

Example 7

4-(β-D-Glucopyranosyloxy)-6-hydroxy-3-(2-phenyl-ethyl)benzofuran

To a solution of 4-(2,3,4,6-tetra-O-acetyl-β-D-glucopyranosyloxy)-6-hydroxy-3-(2-phenylethyl)benzofuran (45 mg) in methanol (3 mL) was added sodium methoxide (28% methanol solution, 0.015 mL), and the mixture was stirred at room temperature for 1 hour. The reaction mixture was concentrated under deduced pressure, and the residue was purified by column chromatography on silica gel (eluent: dichloromethane/methanol=10/1-5/1) to give the title compound (28 mg).

$^1$H-NMR (CD$_3$OD) δ ppm: 2.9-3.2 (4H, m), 3.35-3.6 (4H, m), 3.73 (1H, dd, J=12.1 Hz, 5.7 Hz), 3.92 (1H, dd, J=12.1 Hz, 2.2 Hz), 5.11 (1H, d, J=7.3 Hz), 6.5 (1H, d, J=1.7 Hz), 6.52 (1H, d, J=1.7 Hz), 7.05-7.15 (2H, m), 7.15-7.3 (4H, m)

Example 8

4-(β-D-Glucopyranosyloxy)-6-methoxy-3-(2-phenylethyl)benzofuran

To a mixture of 4-(2,3,4,6-tetra-O-acetyl-β-D-glucopyranosyloxy)-6-hydroxy-3-(2-phenylethyl)benzofuran (25 mg) and potassium carbonate (18 mg) in N,N-dimethylformamide (1 mL) was added iodomethane (0.007 mL), and the mixture was stirred at room temperature for 4 days. The reaction mixture was poured into water, and the resulting mixture was extracted with ethyl acetate. The extract was washed with water and dried over anhydrous magnesium sulfate. The solvent was removed under reduced pressure, and the residue was dissolved in methanol (2 mL). To the solution was added sodium methoxide (28% methanol solution, 0.008 mL), and the mixture was stirred at room temperature for 1 hour. The reaction mixture was concentrated under reduced pressure, and the residue was purified by column chromatography on silica gel (eluent: dichloromethane/methanol=10/1) to give the title compound (8 mg).

$^1$H-NMR (CD$_3$OD) δ ppm: 2.85-3.2 (4H, m), 3.35-3.65 (4H, m), 3.71 (1H, dd, J=12.1 Hz, 5.8 Hz), 3.81 (3H, s), 3.91 (1H, dd, J=12.1 Hz, 2.0 Hz), 5.14 (1H, d, J=7.6 Hz), 6.63 (1H, d, J=1.6 Hz), 6.68 (1H, d, J=1.6 Hz), 7.05-7.35 (6H, m)

Reference Example 16

N-Methoxy-N-methyl-3-phenylpropionamide

To a mixture of N,O-dimethylhydroxylamine hydrochloride (1.1 g) and pyridine (1.82 mL) in dichloromethane (50 mL) was added 3-phenylpropionyl chloride (1.52 mL) under ice-cooling, and the mixture was stirred at room temperature for 5 hours. The reaction mixture was concentrated under reduced pressure. To the residue was added 1 mol/L hydrochloric acid, and the mixture was extracted with ethyl acetate. The extract was washed with water and dried over anhydrous magnesium sulfate. The solvent was removed under reduced pressure to give the title compound (1.89 g).

$^1$H-NMR (CDCl$_3$) δ ppm: 2.7-2.8 (2H, m), 2.9-3.0 (2H, m), 3.18 (3H, s), 3.61 (3H, s), 7.15-7.35 (5H, m)

Reference Example 17

2'-Mercapto-6'-methoxydihydrochalcone

To a solution of N,N,N',N'-tetramethylethylenediamine (4.31 mL) in cyclohexane (50 ml) were added n-butyl lithium (2.46 mol/L n-hexane solution 12.2 mL) and 3-methoxythiophenol (2 g) successively under ice-cooling. The reaction mixture was stirred at room temperature overnight. To the reaction mixture was added N-methoxy-N-methyl-3-phenylpropionamide (2.76 g) under ice-cooling, and the mixture was stirred at room temperature overnight. The reaction mixture was poured into 1 mol/L hydrochloric acid, and the resulting mixture was extracted with diethyl ether. The extract was washed with water and dried over anhydrous magnesium sulfate. The solvent was removed under reduced pressure, and the residue was purified by column chromatography on silica gel (eluent: n-hexane/ethyl acetate=10/1-5/1) to give the title compound (1.2 g).

$^1$H-NMR (CDCl$_3$) δ ppm: 3.0-3.1 (2H, m), 3.1-3.2 (2H, m), 3.78 (3H, s), 6.71 (1H, d, J=8.5 Hz), 6.92 (1H, d, J=8.0 Hz), 7.15-7.35 (6H, m)

Reference Example 18

4-Methoxy-2-methoxycarbonyl-3-(2-phenylethyl)benzo[b]-thiophene

To a solution of 2'-mercapto-6'-methoxydihydrochalcone (1.2 g) and triethylamine (0.92 mL) in dichloromethane (10 mL) was added methyl bromoacetate (0.46 mL), and the mixture was stirred at room temperature for 3 hours. The reaction mixture was poured into water, and the resulting mixture was extracted with diethyl ether. The extract was washed with water and brine, and dried over anhydrous magnesium sulfate. The solvent was removed under reduced pressure, and the residue was dissolved in methanol (15 mL). To the solution was added sodium methoxide (28% methanol solution, 1.7 mL), and the mixture was stirred at room temperature overnight. The crystals precipitated from the reaction mixture were collected by filtration and dried under reduced pressure to give the title compound (1.09 g).

$^1$H-NMR (CDCl$_3$) δ ppm: 2.9-3.0 (2H, m), 3.75-3.85 (2H, m), 3.91 (3H, s), 4.0 (3H, s), 6.79 (1H, dd, J=7.4 Hz, 1.7 Hz), 7.15-7.25 (1H, m), 7.25-7.35 (4H, m), 7.35-7.45 (2H, m)

Reference Example 19

2-Carboxy-4-methoxy-3-(2-phenylethyl)benzo[b]thiophene

To a solution of 4-methoxy-2-methoxycarbonyl-3-(2-phenylethyl)benzo[b]thiophene (1.09 g) in tetrahydrofuran (6 mL)-methanol (21 mL) was added 1 mol/L aqueous sodium hydroxide solution (21 mL), and the mixture was heated for reflux for 3.5 hours. The reaction mixture was cooled to room temperature. To the mixture was added 2 mol/L hydrochloric acid (11 mL), and the precipitated crystals were collected by filtration. The crystals were dried under reduced pressure to give the title compound (1 g).

(continued from previous page)
filtration, and the filtrate was concentrated under reduced pressure. The residue was purified by column chromatography on silica gel (eluent: n-hexane/ethylacetate=2/1-3/2-1/1) to give the title compound (70 mg).

$^1$H-NMR (CDCl$_3$) δ ppm: 1.93 (3H, s), 2.02 (3H, s), 2.061 (3H, s), 2.062 (3H, s), 2.8-3.05 (4H, m), 3.9-4.0 (1H, m), 4.2 (1H, dd, J=12.2 Hz, 2.4 Hz), 4.29 (1H, dd, J=12.2 Hz, 5.5 Hz), 5.02 (1H, s), 5.15-5.25 (1H, m), 5.25-5.4 (3H, m), 6.44 (1H, d, J=1.9 Hz), 6.63 (1H, d, J=1.9 Hz), 7.0 (1H, s), 7.1-7.3 (5H, m)

¹H-NMR (DMSO-d₆) δ ppm: 2.8-2.9 (2H, m), 3.65-3.75 (2H, m), 3.99 (3H, s), 6.98 (1H, d, J=7.9 Hz), 7.15-7.35 (5H, m), 7.45 (1H, t, J=7.9 Hz), 7.53 (1H, d, J=7.9 Hz)

Reference Example 20

4-Methoxy-3-(2-phenylethyl)benzo[b]thiophene

A suspension of 2-carboxy-4-methoxy-3-(2-phenylethyl)benzo[b]thiophene (1 g) and a catalytic amount of copper powder in quinoline (15 mL) was stirred at 200° C. for 2 hours. The reaction mixture was cooled to room temperature and poured into 1 mol/L hydrochloric acid, and the resulting mixture was extracted with ethyl acetate. The extract was washed with 1 mol/L hydrochloric acid and water, and dried over anhydrous magnesium sulfate. The solvent was removed under reduced pressure, and the residue was purified by column chromatography on silica gel (eluent: n-hexane/ethyl acetate=5/1) to give the title compound (0.77 g).
¹H-NMR (CDCl₃) δ ppm: 2.95-3.05 (2H, m), 3.25-3.35 (2H, m), 3.97 (3H, s), 6.77 (1H, d, J=7.8 Hz), 6.88 (1H, s), 7.15-7.35 (6H, m), 7.43 (1H, d, J=7.9 Hz)

Reference Example 21

4-Hydroxy-3-(2-phenylethyl)benzo[b]thiophene

To a solution of 4-methoxy-3-(2-phenylethyl)benzo-[b]thiophene (0.77 g) in dichloromethane (25 mL) was added boron tribromide (0.54 mL) at −78° C., and the mixture was stirred at room temperature overnight. To the reaction mixture was added a saturated aqueous sodium hydrogen carbonate solution, and the resulting mixture was extracted with diethylether. The extract was washed with water and dried over anhydrous magnesium sulfate. The solvent was removed under reduced pressure, and the residue was purified by column chromatography on silica gel (eluent: n-hexane/ethyl acetate=6/1) to give the title compound (0.66 g).
¹H-NMR (CDCl₃) δ ppm: 3.0-3.1 (2H, m), 3.3-3.4 (2H, m), 5.16 (1H, s), 6.65 (1H, d, J=7.7 Hz), 6.89 (1H, s), 7.1-7.35 (6H, m), 7.42 (1H, d, J=8.4 Hz)

Example 9

4-(2,3,4,6-Tetra-O-acetyl-β-D-glucopyranosyloxy)-3-(2-phenylethyl)benzo[b]thiophene To a solution of 4-hydroxy-3-(2-phenylethyl)benzo-[b]thiophene (80 mg), 2,3,4,6-tetra-O-acetyl-1-O-trichloroacetoimidoyl-α-D-glucopyranose (0.17 g) in dichloromethane (3 mL) was added boron trifluoride-diethyl ether complex (0.044 mL), and the mixture was stirred at room temperature for 30 minutes. The reaction mixture was purified by column chromatography on silica gel (eluent: n-hexane/ethyl acetate=2/1-3/2) to give the title compound (75 mg).
¹H-NMR (CDCl₃) δ ppm: 1.97 (3H, s), 2.01 (3H, s), 2.03 (3H, s), 2.06 (3H, s), 2.95-3.1 (2H, m), 3.1-3.25 (1H, m), 3.3-3.4 (1H, m), 3.85-3.95 (1H, m), 4.16 (1H, dd, J=12.3 Hz, 2.3 Hz), 4.28 (1H, dd, J=12.3 Hz, 5.4 Hz), 5.15-5.25 (1H, m), 5.3-5.4 (2H, m), 5.4-5.45 (1H, m), 6.76 (1H, s), 6.91 (1H, d, J=7.9 Hz), 7.1-7.3 (6H, m), 7.54 (1H, d, J=8.1 Hz)

Example 10

4-(β-D-Glucopyranosyloxy)-3-(2-phenylethyl)benzo[b]-thiophene

To a suspension of 4-(2,3,4,6-tetra-O-acetyl-β-D-glucopyranosyloxy)-3-(2-phenylethyl)benzo[b]thiophene (75 mg) in methanol (3 mL) was added sodium methoxide (28% methanol solution, 0.025 mL), and the mixture was stirred at room temperature for 30 minutes. The reaction mixture was concentrated under reduced pressure, and the residue was purified by column chromatography on silica gel (eluent: dichloromethane/methanol=10/1) to give the title compound (42 mg).
¹H-NMR (CD₃OD) δ ppm: 2.9-3.05 (1H, m), 3.05-3.15 (1H, m), 3.2-3.35 (1H, m), 3.35-3.45 (1H, m), 3.45-3.65 (4H, m), 3.71 (1H, dd, J=12.0 Hz, 5.8 Hz), 3.91 (1H, dd, J=12.0 Hz, 2.2 Hz), 5.22 (1H, d, J=7.8 Hz), 6.9 (1H, s), 7.05-7.3 (7H, m), 7.47 (1H, d, J=7.8 Hz)

Reference Example 22

4-Benzyloxy-3-[(E)-2-phenylvinyl]indole

To a suspension of sodium hydride (60%, 48 mg) in dimethyl sulfoxide (3 mL) was added benzyltriphenylphosphonium chloride (0.47 g), and the mixture was stirred at 65° C. for 1 hour. The reaction mixture was cooled in ice. To the mixture was added 4-benzyloxy-3-formylindole (0.25 g), and the mixture was stirred at 85° C. for 3 hours. The reaction mixture was cooled to room temperature. To the mixture was added water, and the mixture was extracted with ethyl acetate (three times). The extract was washed with water twice, a saturated aqueous sodium hydrogen carbonate solution and brine successively, and dried over anhydrous magnesium sulfate. The solvent was removed under reduced pressure, and the residue was purified by column chromatography on aminopropylated silica gel (eluent: n-hexane/ethyl acetate=3/1) to give the title compound (0.32 g).
¹H-NMR (CDCl₃) δ ppm: 5.23 (2H, s), 6.65-6.75 (1H, m), 6.88 (1H, d, J=16.6 Hz), 6.95-7.65 (13H, m), 7.88 (1H, d, J=16.6 Hz), 8.29 (1H, brs)

Reference Example 23

4-Hydroxy-3-(2-phenylethyl)indole

To a solution of 4-benzyloxy-3-[(E)-2-phenylvinyl]indole (0.1 g) in ethanol (5 mL) was added 10% palladium-carbon powder (25 mg), and the mixture was stirred at room temperature under a hydrogen atmosphere overnight. The insoluble material was removed by filtration. The filtrate was concentrated under reduced pressure, and the residue was purified by column chromatography on aminopropylated silica gel (eluent: n-hexane/ethyl acetate=3/1) to give the title compound (70 mg).
¹H-NMR (CDCl₃) δ ppm: 2.95-3.1 (2H, m), 3.15-3.25 (2H, m), 5.24 (1H, brs), 6.35-6.45 (1H, m), 6.75-6.85 (1H, m), 6.9-7.05 (2H, m), 7.1-7.35 (5H, m), 8.02 (1H, brs)

Example 11

4-(β-D-Glucopyranosyloxy)-3-(2-phenylethyl)indole

To a solution of 4-hydroxy-3-(2-phenylethyl)indole (70 mg) and 2,3,4,6-tetra-O-acetyl-1-O-trichloroacetoimidoyl-α-D-glucopyranose (0.22 g) in dichloromethane (3 mL) was added boron trifluoride-diethyl ether complex (0.081 mL), and the mixture was stirred at room temperature for 1 hour. The reaction mixture was purified by preparative thin layer chromatography (eluent: n-hexane/ethyl acetate=1/1) to give 4-(2,3,4,6-tetra-O-acetyl-β-D-glucopyranosyloxy)-3-(2-phenylethyl)indole. This material was dissolved in tetrahydrofuran (1 mL)-methanol (0.5 mL). To the solution was added sodium methoxide (28% methanol solution, 0.024 mL), and the mixture was stirred at room temperature for 2 hours. The reaction mixture was purified by preparative thin layer chromatography (eluent: dichloromethane/methanol=5/1) to give the title compound (22 mg).

$^1$H-NMR (CD$_3$OD) δ ppm: 2.9-3.2 (3H, m), 3.25-3.8 (6H, m), 3.85-3.95 (1H, m), 5.15-5.25 (1H, m), 6.65-6.8 (2H, m), 6.9-7.3 (7H, m)

Reference Example 24

2'-(2,3,4,6-Tetra-O-acetyl-β-D-glucopyranosyloxy)-6'-hydroxyacetophenone

To a mixture of 2',6'-dihydroxyacetophenone (1 g), potassium carbonate (4.54 g) and benzyltri(n-butyl)ammonium chloride (0.41 g) in chloroform (13 mL) were added water (0.5 mL) and acetobromo-α-D-glucose (2.7 g), and the mixture was stirred at room temperature for 24 hours. The reaction mixture was poured into water, and the mixture was acidified by addition of 2 mol/L hydrochloric acid. The resulting mixture was extracted with ethyl acetate, and the extract was washed with water and brine. The extract was dried over anhydrous magnesium sulfate, and the solvent was removed under reduced pressure. The residue was treated with methanol, and the precipitated crystals were collected by filtration and dried under reduced pressure to give the title compound (1.38 g).

$^1$H-NMR (CDCl$_3$) δ ppm: 2.0-2.1 (12H, m), 2.63 (3H, s), 3.85-3.95 (1H, m), 4.15 (1H, dd, J=12.3 Hz, 2.4 Hz), 4.29 (1H, dd, J=12.3 Hz, 5.2 Hz), 5.15-5.25 (1H, m), 5.25-5.4 (3H, m), 6.48 (1H, d, J=8.3 Hz), 6.7 (1H, d, J=8.3 Hz), 7.34 (1H, t, J=8.3 Hz), 12.96 (1H, s)

Reference Example 25

2'-(2,3,4,6-Tetra-O-acetyl-β-D-glucopyranosyloxy)-6'-(methoxycarbonylmethoxy)acetophenone To a solution of 2'-(2,3,4,6-tetra-O-acetyl-β-D-glucopyranosyloxy)-6'-hydroxyacetophenone (0.6 g) in N,N-dimethylformamide (5 mL) were added potassium carbonate (0.26 g) and methyl bromoacetate (0.13 mL), and the mixture was stirred at room temperature for 3 days. The reaction mixture was poured into water, and the precipitated crystals were collected by filtration. The crystals were washed with water and dried under reduced pressure to give the title compound (0.62 g).

$^1$H-NMR (CDCl$_3$) δ ppm: 2.02 (3H, s), 2.04 (3H, s), 2.09 (3H, s), 2.12 (3H, s), 2.49 (3H, s), 3.77 (3H, s), 3.8-3.9 (1H, m), 4.2 (1H, dd, J=12.4 Hz, 2.4 Hz), 4.28 (1H, dd, J=12.4 Hz, 5.4 Hz), 4.64 (2H, s), 5.0 (1H, d, J=7.6 Hz), 5.1-5.2 (1H, m), 5.2-5.3 (2H, m), 6.54 (1H, d, J=8.3 Hz), 6.79 (1H, d, J=8.3 Hz), 7.22 (1H, t, J=8.3 Hz)

Example 12

4-(β-D-Glucopyranosyloxy)-3-[2-(3-hydroxyphenyl)ethyl]-benzofuran

To a mixture of 2'-(2,3,4,6-tetra-O-acetyl-β-D-glucopyranosyloxy)-6'-(methoxycarbonylmethoxy)acetophenone (0.2 g) and 3-benzyloxybenzaldehyde (84 mg) in ethanol (4 mL) were added water (1 mL) and potassium hydroxide (0.24 g), and the mixture was stirred at room temperature overnight. To the reaction mixture was added 10% palladium-carbon powder (0.1 g), and the mixture was stirred at room temperature under a hydrogen atmosphere for 10 hours. The insoluble material was removed by filtration, and the filtrate was concentrated under reduced pressure. To the residue was added 1 mol/L hydrochloric acid (6 mL), and the mixture was extracted with ethyl acetate. The extract was washed with water and dried over anhydrous magnesium sulfate. The solvent was removed under reduced pressure, and the residue was dissolved in acetic acid (2.2 mL). To the solution were added sodium acetate (0.39 g) and acetic anhydride (0.39 mL), and the mixture was stirred at 115° C. overnight. The reaction mixture was poured into water, and the resulting mixture was extracted with ethyl acetate. The extract was washed with a saturated aqueous sodium hydrogen carbonate solution twice and water, and dried over anhydrous magnesium sulfate. The solvent was removed under reduced pressure, and the residue was purified by column chromatography on silica gel (eluent: n-hexane/ethyl acetate=2/1-3/2) to give 3-[2-(3-acetoxyphenyl)ethyl]-4-(2,3,4,6-tetra-O-acetyl-β-D-glucopyranosyloxy)benzofuran (48 mg). This material was dissolved in methanol (3 mL). To the solution was added sodium methoxide (28% methanol solution, 0.015 mL), and the mixture was stirred at room temperature for 1 hour. To the reaction mixture was added acetic acid (0.09 mL), and the resulting mixture was concentrated under reduced pressure. The residue was purified by solid phase extraction on ODS (washing solvent: distilled water, eluent: methanol) to give the title compound (27 mg).

$^1$H-NMR (CD$_3$OD) δ ppm: 2.85-3.1 (3H, m), 3.1-3.25 (1H, m), 3.4-3.55 (3H, m), 3.55-3.65 (1H, m), 3.72 (1H, dd, J=12.0 Hz, 5.8 Hz), 3.91 (1H, dd, J=12.0 Hz, 2.2 Hz), 5.18 (1H, d, J=7.6 Hz), 6.55-6.65 (1H, m), 6.65-6.75 (2H, m), 6.96 (1H, d, J=8.1 Hz), 7.0-7.1 (2H, m), 7.18 (1H, t, J=8.1 Hz), 7.28 (1H, s)

Example 13

4-(β-D-Glucopyranosyloxy)-3-[2-(2-hydroxyphenyl)ethyl]-benzofuran

The title compound was prepared in a similar manner to that described in Example 12 using 2-benzyloxybenzaldehyde instead of 3-benzyloxybenzaldehyde.

$^1$H-NMR (CD$_3$OD) δ ppm: 2.95-3.2 (4H, m), 3.4-3.55 (3H, m), 3.6-3.7 (1H, m), 3.72 (1H, dd, J=12.2 Hz, 5.4 Hz), 3.91 (1H, dd, J=12.2 Hz, 1.9 Hz), 5.17 (1H, d, J=8.1 Hz), 6.65-6.8 (2H, m), 6.9-7.05 (2H, m), 7.05-7.1 (2H, m), 7.18 (1H, t, J=8.1 Hz), 7.3 (1H, s)

Example 14

4-(β-D-Glucopyranosyloxy)-3-[2-(4-hydroxyphenyl)ethyl]-benzofuran

The title compound was prepared in a similar manner to that described in Example 12 using 4-benzyloxybenzaldehyde instead of 3-benzyloxybenzaldehyde.

$^1$H-NMR (CD$_3$OD) δ ppm: 2.8-3.1 (3H, m), 3.1-3.2 (1H, m), 3.35-3.55 (3H, m), 3.55-3.65 (1H, m), 3.71 (1H, dd, J=12.0 Hz, 5.7 Hz), 3.9 (1H, dd, J=12.0 Hz, 2.1 Hz), 5.18 (1H, d, J=7.4 Hz), 6.65-6.7 (2H, m), 6.95 (1H, d, J=8.3 Hz), 7.0-7.1 (3H, m), 7.18 (1H, t, J=8.3 Hz), 7.25 (1H, s)

Reference Example 26

6'-Hydroxy-2'-(methoxycarbonylmethoxy)acetophenone

To a mixture of 2',6'-dihydroxyacetophenone (6 g) and potassium carbonate (5.72 g) in acetone (20 mL) was added methyl bromoacetate (3.73 mL), and the mixture was stirred at room temperature for 5 days. To the reaction mixture was added water, and the precipitated crystals were collected by filtration. The crystals were washed with water and dried under reduced pressure to give the title compound (7.89 g).

$^1$H-NMR (CDCl$_3$) δ ppm: 2.8 (3H, s), 3.83 (3H, s), 4.72 (2H, s), 6.24 (1H, dd, J=8.4 Hz, 1.0 Hz), 6.63 (1H, dd, J=8.4 Hz, 1.0 Hz), 7.32 (1H, t, J=8.4 Hz), 13.22 (1H, s)

Reference Example 27

2'-Carboxymethoxy-6'-hydroxy-4-(3-hydroxypropoxy)dihydrochalcone

A mixture of 4-hydroxybenzaldehyde (1 g), benzyl 3-bromopropylether (1.52 mL), cesium carbonate (3.2 g) and a catalytic amount of sodium iodide in N,N-dimethylformamide (10 mL) was stirred at room temperature overnight. The reaction mixture was poured into water, and the resulting mixture was extracted with diethyl ether. The extract was washed with water and dried over anhydrous magnesium sulfate. The solvent was removed under reduced pressure, and the residue was dissolved in ethanol (16 mL). To the solution was added 6'-hydroxy-2'-(methoxycarbonylmethoxy)acetophenone (1.71 g), water (4 mL) and potassium hydroxide (5.13 g), and the mixture was stirred at room temperature overnight. To the reaction mixture was added 10% palladium-carbon powder (0.2 g), and the mixture was stirred at room temperature under a hydrogen atmosphere overnight. The insoluble material was removed by filtration, and the solvent of the filtrate was removed under reduced pressure. The residue was dissolved in water, and the solution was washed with diethyl ether. The aqueous layer was acidified by addition of concentrated hydrochloric acid, and the resulting mixture was extracted with ethyl acetate twice. The extract was washed with brine and dried over anhydrous magnesium sulfate. The solvent was removed under reduced pressure, and the residue was dissolved in methanol (12 mL)-ethyl acetate (6 mL). To the solution was added 10% palladium-carbon powder (0.5 g), and the mixture was stirred at room temperature under a hydrogen atmosphere overnight. The insoluble material was removed by filtration. The solvent of the filtrate was removed under reduced pressure to give the title compound (2.8 g).

$^1$H-NMR (DMSO-d$_6$) δ ppm: 1.75-1.9 (2H, m), 2.84 (2H, t, J=7.6 Hz), 3.22 (2H, t, J=7.6 Hz), 3.54 (2H, t, J=6.2 Hz), 3.98 (2H, t, J=6.3 Hz), 4.5 (1H, brs), 4.72 (2H, s), 6.45 (1H, d, J=8.3 Hz), 6.51 (1H, d, J=8.3 Hz), 6.75-6.85 (2H, m), 7.1-7.15 (2H, m), 7.23 (1H, t, J=8.3 Hz), 11.1 (1H, s), 12.85-13.3 (1H, br)

Reference Example 28

2'-Carboxymethoxy-6'-hydroxy-3-(2-hydroxyethoxy)dihydrochalcone

To a suspension of 6'-hydroxy-2'-(methoxycarbonylmethoxy)acetophenone (1 g) and 3-(2-hydroxyethoxy)benzaldehyde (0.74 g) in ethanol (12 mL) were added water (3 mL) and potassium hydroxide (3 g), and the mixture was stirred at room temperature overnight. To the reaction mixture was added 10% palladium-carbon powder (0.2 g), and the mixture was stirred at room temperature under a hydrogen atmosphere for 8 hours. The insoluble material was removed by filtration, and the solvent of the filtrate was removed under reduced pressure. The residue was dissolved in water, and the solution was washed with diethyl ether. The aqueous layer was acidified by addition of concentrated hydrochloric acid, and the resulting mixture was extracted with ethyl acetate twice. The extract was washed with brine and dried over anhydrous magnesium sulfate. The solvent was removed under reduced pressure. The residue was treated with diethyl ether, and the precipitated crystals were collected by filtration. The crystals were dried under reduced pressure to give the title compound (1.6 g).

$^1$H-NMR (DMSO-d$_6$) δ ppm: 2.88 (2H, t, J=7.8 Hz), 3.25 (2H, t, J=7.8 Hz), 3.69 (2H, t, J=4.9 Hz), 3.95 (2H, t, J=4.9 Hz), 4.73 (2H, s), 4.81 (1H, brs), 6.46 (1H, d, J=8.3 Hz), 6.52 (1H, d, J=8.3 Hz), 6.7-6.85 (3H, m), 7.15 (1H, t, J=8.2 Hz), 7.23 (1H, t, J=8.3 Hz), 11.06 (1H, s), 13.06 (1H, brs)

Reference Example 29

2'-Carboxymethoxy-6'-hydroxy-4-(2-hydroxyethoxy)dihydrochalcone

The title compound was prepared in a similar manner to that described in Reference Example 28 using 4-(2-hydroxyethoxy)benzaldehyde instead of 3-(2-hydroxyethoxy)benzaldehyde.

$^1$H-NMR (DMSO-d$_6$) δ ppm: 2.8-2.9 (2H, m), 3.15-3.25 (2H, m), 3.65-3.75 (2H, m), 3.9-3.95 (2H, m), 4.72 (2H, s), 4.8 (1H, brs), 6.4-6.55 (2H, m), 6.75-6.85 (2H, m), 7.1-7.15 (2H, m), 7.2-7.3 (1H, m), 11.1 (1H, s), 13.05 (1H, brs)

Reference Example 30

4-Hydroxy-3-{2-[4-(3-hydroxypropoxy)phenyl]ethyl}benzofuran

To a solution of 2'-carboxymethoxy-6'-hydroxy-4-(3-hydroxypropoxy)dihydrochalcone (2.8 g) in acetic acid (39.4 mL) were added sodium acetate (17.8 g) and acetic anhydride (17.9 mL), and the mixture was stirred at 115° C. overnight. The reaction mixture was poured into water, and the resulting mixture was extracted with diethylether. The extract was washed with water twice, a saturated aqueous sodium hydrogen carbonate solution, water and brine successively, and dried over anhydrous magnesium sulfate. The solvent was removed under reduced pressure, and the residue was dissolved in methanol (10 mL). To the solution was added 2 mol/L aqueous sodium hydroxide solution (26 mL), and the mixture was stirred at room temperature for 3 hours. The reaction mixture was acidified by addition of 2 mol/L hydrochloric acid, and the resulting mixture was extracted with diethyl ether. The extract was washed with brine and dried over anhydrous magnesium sulfate, and the solvent was removed under reduced pressure. The residue was purified by column chromatography on silica gel (eluent: n-hexane/ethyl acetate=2/1-1/1) to give the title compound (0.45 g).

$^1$H-NMR (DMSO-d$_6$) δ ppm: 1.8-1.9 (2H, m), 2.85-3.0 (4H, m), 3.5-3.6 (2H, m), 3.99 (2H, t, J=6.6 Hz), 4.5 (1H, t, J=5.0 Hz), 6.6 (1H, d, J=7.9 Hz), 6.8-6.85 (2H, m), 6.93 (1H, d, J=7.9 Hz), 7.05 (1H, t, J=7.9 Hz), 7.1-7.15 (2H, m), 7.48 (1H, s), 9.89 (1H, s)

Reference Example 31

4-Hydroxy-3-{2-[3-(2-hydroxyethoxy)phenyl]ethyl}benzofuran

The title compound was prepared in a similar manner to that described in Reference Example 30 using 2'-carboxymethoxy-6'-hydroxy-3-(2-hydroxyethoxy)dihydrochalcone instead of 2'-carboxymethoxy-6'-hydroxy-4-(3-hydroxypropoxy)dihydrochalcone.

¹H-NMR (CDCl₃) δ ppm: 2.95-3.05 (2H, m), 3.05-3.15 (2H, m), 3.9-4.0 (2H, m), 4.0-4.1 (2H, m), 5.15 (1H, s), 6.54 (1H, dd, J=7.8 Hz, 1.2 Hz), 6.7-6.9 (3H, m), 7.0-7.15 (2H, m), 7.21 (1H, t, J=7.8 Hz), 7.23 (1H, s)

Reference Example 32

4-Hydroxy-3-{2-[4-(2-hydroxyethoxy)phenyl]ethyl}benzofuran

The title compound was prepared in a similar manner to that described in Reference Example 30 using 2'-carboxymethoxy-6'-hydroxy-4-(2-hydroxyethoxy)dihydrochalcone instead of 2'-carboxymethoxy-6'-hydroxy-4-(3-hydroxypropoxy)dihydrochalcone.

¹H-NMR (DMSO-d₆) δ ppm: 2.85-3.0 (4H, m), 3.65-3.75 (2H, m), 3.94 (2H, t, J=5.0 Hz), 4.81 (1H, t, J=5.6 Hz), 6.6 (1H, d, J=8.1 Hz), 6.8-6.9 (2H, m), 6.93 (1H, d, J=8.1 Hz), 7.05 (1H, t, J=8.1 Hz), 7.1-7.15 (2H, m), 7.48 (1H, s), 9.89 (1H, s)

Example 15

4-(2,3,4,6-Tetra-O-acetyl-β-D-glucopyranosyloxy)-3-{2-[4-(3-hydroxypropoxy)phenyl]ethyl}benzofuran To a solution of 4-hydroxy-3-{2-[4-(3-hydroxypropoxy)phenyl]ethyl}benzofuran (0.45 g) and imidazole (0.11 g) in N,N-dimethylformamide (10 mL) was added tert-butyldiphenylsilyl chloride (0.4 mL), and the mixture was stirred at room temperature overnight. The reaction mixture was poured into water, and the resulting mixture was extracted with diethyl ether. The extract was washed with water twice and brine successively, and dried over anhydrous magnesium sulfate. The solvent was removed under reduced pressure, and the residue was dissolved in dichloromethane (8 mL). To the solution were added 2,3,4,6-tetra-o-acetyl-1-O-trichloroacetoimidoyl-α-D-glucopyranose (0.42 g) and boron trifluoride-diethyl ether complex (0.11 mL), and the mixture was stirred at room temperature for 30 minutes. The reaction mixture was purified by column chromatography on silica gel (eluent: n-hexane/ethyl acetate=3/1-3/2) to give 4-(2,3,4,6-tetra-O-acetyl-β-D-glucopyranosyloxy)-3-(2-{4-[3-(tert-butyldiphenylsilyloxy)propoxy]phenyl}ethyl)benzofuran (0.6 g). This material was dissolved in tetrahydrofuran (8 mL). To the solution was added tetra(n-butyl)ammonium fluoride (1 mol/L tetrahydrofuran solution, 1.9 mL), and the mixture was stirred at room temperature for 1 hour. The reaction mixture was poured into water, and the resulting mixture was extracted with ethyl acetate. The extract was washed with brine and dried over anhydrous magnesium sulfate. The solvent was removed under reduced pressure, and the residue was purified by column chromatography on silica gel (eluent: n-hexane/ethyl acetate=3/2-1/2) to give the title compound (0.26 g).

¹H-NMR (CDCl₃) δ ppm: 1.81 (1H, t, J=5.5 Hz), 1.97 (3H, s), 2.0-2.1 (11H, m), 2.85-3.05 (4H, m), 3.8-3.95 (3H, m), 4.11 (2H, t, J=5.9 Hz), 4.17 (1H, dd, J=12.3 Hz, 2.3 Hz), 4.29 (1H, dd, J=12.3 Hz, 5.5 Hz), 5.15-5.25 (1H, m), 5.3-5.4 (3H, m), 6.75-6.85 (3H, m), 7.0-7.15 (3H, m), 7.15-7.2 (2H, m)

Example 16

4-(2,3,4,6-Tetra-O-acetyl-β-D-glucopyranosyloxy)-3-{2-[3-(2-hydroxyethoxy)phenyl]ethyl}benzofuran The title compound was prepared in a similar manner to that described in Example 15 using 4-hydroxy-3-{2-[3-(2-hydroxyethoxy)phenyl]ethyl}benzofuran instead of 4-hydroxy-3-(2-[4-(3-hydroxypropoxy)phenyl]ethyl)benzofuran.

¹H-NMR (CDCl₃) δ ppm: 1.95-2.1 (12H, m), 2.35-2.5 (1H, m), 2.85-3.15 (4H, m), 3.85-4.0 (3H, m), 4.0-4.25 (3H, m), 4.25-4.35 (1H, m), 5.2-5.3 (1H, m), 5.3-5.45 (3H, m), 6.7-6.85 (4H, m), 7.15-7.3 (4H, m)

Example 17

4-(2,3,4,6-Tetra-O-acetyl-β-D-glucopyranosyloxy)-3-(2-[4-(2-hydroxyethoxy)phenyl]ethyl)benzofuran The title compound was prepared in a similar manner to that described in Example 15 using 4-hydroxy-3-(2-[4-{2-hydroxyethoxy)phenyl]ethyl}benzofuran instead of 4-hydroxy-3-{2-[4-(3-hydroxypropoxy)phenyl]ethyl}benzofuran.

¹H-NMR (CDCl₃) δ ppm: 1.97 (3H, s), 2.025 (3H, s), 2.032 (3H, s), 2.06 (3H, s), 2.85-3.1 (4H, m), 3.85-4.0 (3H, m), 4.05-4.1 (2H, m), 4.17 (1H, dd, J=12.3 Hz, 2.3 Hz), 4.29 (1H, dd, J=12.3 Hz, 5.5 Hz), 5.15-5.25 (1H, m), 5.3-5.4 (3H, m), 6.75-6.8 (1H, m), 6.8-6.9 (2H, m), 7.0-7.15 (3H, m), 7.15-7.25 (2H, m)

Example 18

4-(β-D-Glucopyranosyloxy)-3-{2-[4-(3-hydroxypropoxy)phenyl]ethyl}benzofuran

To a solution of 4-(2,3,4,6-tetra-O-acetyl-β-D-glucopyranosyloxy)-3-{2-[4-(3-hydroxypropoxy)phenyl]ethyl}-benzofuran (20 mg) in methanol (2 mL) was added sodium methoxide (28% methanol solution, 0.006 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (14 mg).

¹H-NMR (CD₃OD) δ ppm: 1.9-2.0 (2H, m), 2.85-3.1 (3H, m), 3.1-3.25 (1H, m), 3.35-3.55 (3H, m), 3.55-3.65 (1H, m), 3.65-3.75 (3H, m), 3.9 (1H, dd, J=11.9 Hz, 2.3 Hz), 4.04 (2H, t, J=6.2 Hz), 5.18 (1H, d, J=8.1 Hz), 6.75-6.85 (2H, m), 6.95 (1H, d, J=8.0 Hz), 7.05-7.15 (3H, m), 7.18 (1H, t, J=8.0 Hz), 7.25 (1H, s)

Example 19

4-(β-D-Glucopyranosyloxy)-3-{2-[4-(2-hydroxyethoxy)phenyl]ethyl}benzofuran

The title compound was prepared in a similar manner to that described in Example 18 using 4-(2,3,4,6-tetra-O-acetyl-β-D-glucopyranosyloxy)-3-{2-[4-(2-hydroxyethoxy)phenyl]ethyl}benzofuran instead of 4-(2,3,4,6-tetra-O-acetyl-β-D-glucopyranosyloxy)-3-{2-[4-(3-hydroxypropoxy)phenyl]ethyl}benzofuran.

¹H-NMR (CD₃OD) δ ppm: 2.85-3.1 (3H, m), 3.1-3.25 (1H, m), 3.35-3.45 (1H, m), 3.45-3.55 (2H, m), 3.55-3.65 (1H, m), 3.71 (1H, dd, J=12.1 Hz, 5.7 Hz), 3.85 (2H, t, J=4.6 Hz), 3.9 (1H, dd, J=12.1 Hz, 2.2 Hz), 3.95-4.05 (2H, m), 5.18 (1H, d, J=7.4 Hz), 6.8-6.9 (2H, m), 6.95 (1H, d, J=8.1 Hz), 7.08 (1H, d, J=8.1 Hz), 7.1-7.15 (2H, m), 7.18 (1H, t, J=8.1 Hz), 7.25 (1H, s)

Example 20

4-(β-D-Glucopyranosyloxy)-3-{2-[3-(2-hydroxy-ethoxy)phenyl]ethyl}benzofuran

The title compound was prepared in a similar manner to that described in Example 18 using 4-(2,3,4,6-tetra-O-acetyl-β-D-glucopyranosyloxy)-3-{2-[3-(2-hydroxyethoxy)phenyl]ethyl}benzofuran instead of 4-(2,3,4,6-tetra-O-acetyl-β-D-glucopyranosyloxy)-3-(2-[4-(3-hydroxypropoxy)phenyl]ethyl)benzofuran.
MS(ESI, m/z): 478 [M+NH$_4$]$^+$

Example 21

4-(β-D-Glucopyranosyloxy)-3-(2-(4-[3-(2-hydroxy-ethylamino)propoxy]phenyl)ethyl)benzofuran To a solution of 4-(2,3,4,6-tetra-O-acetyl-β-D-glucopyranosyloxy)-3-(2-[4-(3-hydroxypropoxy)phenyl]ethyl)benzofuran (0.23 g) and triethylamine (0.1 mL) in dichloromethane (6 mL) was added methanesulfonyl chloride (0.042 mL) under ice-cooling, and the mixture was stirred at room temperature for 2 hours. The reaction mixture was poured into 0.5 mol/L hydrochloric acid, and the resulting mixture was extracted with ethyl acetate. The extract was washed with water and brine, and dried over anhydrous magnesium sulfate. The solvent was removed under reduced pressure to give 4-(2,3,4,6-tetra-O-acetyl-β-D-glucopyranosyloxy)-3-(2-{(4-[3-(methanesulfonyloxy)propoxy]phenyl}ethyl)benzofuran (0.25 g). The obtained 4-(2,3,4,6-tetra-O-acetyl-β-D-glucopyranosyloxy)-3-(2-{4-[3-(methanesulfonyloxy)propoxy]phenyl}ethyl)benzofuran (30 mg) was dissolved in acetonitrile (0.5 mL)-ethanol (0.5 mL). To the solution were added 2-aminoethanol (0.025 mL) and a catalytic amount of sodium iodide, and the mixture was stirred at 60° C. for 3 days. The reaction mixture was concentrated under reduced pressure, and the residue was dissolved in methanol (3 mL). To the solution was added sodium methoxide (28% methanol solution, 0.04 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (15 mg).
$^1$H-NMR (CD$_3$OD) δ ppm: 1.9-2.0 (2H, m), 2.73 (2H, t, J=5.6 Hz), 2.8 (2H, t, J=7.2 Hz), 2.85-3.1 (3H, m), 3.1-3.25 (1H, m), 3.35-3.65 (4H, m), 3.66 (2H, t, J=5.6 Hz), 3.71 (1H, dd, J=12.0 Hz, 5.8 Hz), 3.9 (1H, dd, J=12.0 Hz, 2.2 Hz), 4.02 (2H, t, J=6.2 Hz), 5.18 (1H, d, J=7.4 Hz), 6.75-6.85 (2H, m), 6.95 (1H, d, J=8.0 Hz), 7.05-7.15 (3H, m), 7.18 (1H, t, J=8.0 Hz), 7.25 (1H, s)

Example 22

4-(β-D-Glucopyranosyloxy)-3-[2-(4-(3-[4-(2-hydroxyethyl)piperazin-1yl]propoxy)phenyl)ethyl]benzofuran The title compound was prepared in a similar manner to that described in Example 21 using 1-(2-hydroxyethyl)piperazine instead of 2-aminoethanol.
$^1$H-NMR (CD$_3$OD) δ ppm: 1.9-2.0 (2H, m), 2.3-2.8 (12H, m), 2.85-3.1 (3H, m), 3.1-3.25 (1H, m), 3.35-3.55 (3H, m), 3.55-3.65 (1H, m), 3.68 (2H, t, J=6.0 Hz), 3.71 (1H, dd, J=12.3 Hz, 5.8 Hz), 3.9 (1H, dd, J=12.3 Hz, 2.2 Hz), 3.99 (2H, t, J=6.2 Hz), 5.18 (1H, d, J=8.0 Hz), 6.75-6.85 (2H, m), 6.95 (1H, d, J=8.1 Hz), 7.05-7.15 (3H, m), 7.18 (1H, t, J=8.1 Hz), 7.25 (1H, s)

Example 23

4-(β-D-Glucopyranosyloxy)-3-[2-(4-{3-[2-hydroxy-1,1-di(methyl)ethylamino]propoxy}phenyl)ethyl]benzofuran The title compound was prepared in a similar manner to that described in Example 21 using 2-amino-2-methyl-1-propanol instead of 2-aminoethanol.
$^1$H-NMR (CD$_3$OD) δ ppm: 1.05 (6H, s), 1.85-2.0 (2H, m), 2.71 (2H, t, J=7.1 Hz), 2.85-3.1 (3H, m), 3.1-3.25 (1H, m), 3.35-3.45 (3H, m), 3.45-3.55 (2H, m), 3.55-3.65 (1H, m), 3.71 (1H, dd, J=12.1 Hz, 5.6 Hz), 3.9 (1H, dd, J=12.1 Hz, 2.2 Hz), 4.02 (2H, t, J=6.1 Hz), 5.18 (1H, d, J=7.7 Hz), 6.75-6.85 (2H, m), 6.95 (1H, d, J=8.1 Hz), 7.08 (1H, d, J=8.1 Hz), 7.1-7.15 (2H, m), 7.18 (1H, t, J=8.1 Hz), 7.25 (1H, s)

Example 24

4-(β-D-Glucopyranosyloxy)-3-[2-(4-{3-[2-hydroxy-1,1-bis(hydroxymethyl)ethylamino]propoxy}phenyl)ethyl]benzofuran The title compound was prepared in a similar manner to that described in Example 21 using tris(hydroxymethyl)aminomethane instead of 2-aminoethanol.
$^1$H-NMR (CD$_3$OD) δ ppm: 1.85-2.0 (2H, m), 2.81 (2H, t, J=7.2 Hz), 2.85-3.1 (3H, m), 3.1-3.25 (1H, m), 3.35-3.65 (10H, m), 3.71 (1H, dd, J=12.3 Hz, 5.7 Hz), 3.9 (1H, dd, J=12.3 Hz, 2.2 Hz), 4.04 (2H, t, J=6.2 Hz), 5.18 (1H, d, J=7.9 Hz), 6.8-6.85 (2H, m), 6.95 (1H, d, J=8.0 Hz), 7.08 (1H, d, J=8.0 Hz), 7.1-7.15 (2H, m), 7.18 (1H, t, J=8.0 Hz), 7.25 (1H, s)

Example 25

4-(β-D-Glucopyranosyloxy)-3-(2-{4-[2-(2-hydroxy-ethylamino)ethoxy]phenyl}ethyl)benzofuran The title compound was prepared in a similar manner to that described in Example 21 using 4-(2,3,4,6-tetra-O-acetyl-β-D-glucopyranosyloxy)-3-(2-[4-(2-hydroxyethoxy)phenyl]ethyl)benzofuran instead of 4-(2,3,4,6-tetra-O-acetyl-β-D-glucopyranosyloxy)-3-{2-[4-(3-hydroxypropoxy)phenyl]ethyl}-benzofuran.
$^1$H-NMR (CD$_3$OD) δ ppm: 2.78 (2H, t, J=5.4 Hz), 2.85-3.1 (5H, m), 3.1-3.25 (1H, m), 3.35-3.45 (1H, m), 3.45-3.55 (2H, m), 3.55-3.65 (1H, m), 3.65-3.75 (3H, m), 3.9 (1H, dd, J=11.8 Hz, 2.3 Hz), 4.06 (2H, t, J=5.4 Hz), 5.18 (1H, d, J=7.9 Hz), 6.8-6.9 (2H, m), 6.95 (1H, d, J=8.1 Hz), 7.08 (1H, d, J=8.1 Hz), 7.1-7.15 (2H, m), 7.18 (1H, t, J=8.1 Hz), 7.24 (1H, s)

Example 26

4-(β-D-Glucopyranosyloxy)-3-(2-{4-[2-(3-hydroxypropylamino)ethoxy]phenyl}ethyl)benzofuran The title compound was prepared in a similar manner to that described in Example 21 using 4-(2,3,4,6-tetra-O-acetyl-β-D-glucopyranosyloxy)-3-(2-[4-(2-hydroxyethoxy)phenyl]ethyl)benzofuran and 3-amino-1-propanol instead of 4-(2,3,4,6-tetra-O-acetyl-β-D-glucopyranosyloxy)-3-(2-[4-(3-hydroxypropoxy)phenyl]ethyl)benzofuran and 2-aminoethanol, respectively.

$^1$H-NMR (CD$_3$OD) δ ppm: 1.7-1.8 (2H, m), 2.77 (2H, t, J=7.1 Hz), 2.85-3.1 (5H, m), 3.1-3.25 (1H, m), 3.35-3.55 (3H, m), 3.55-3.7 (3H, m), 3.71 (1H, dd, J=12.1 Hz, 5.8 Hz), 3.9 (1H, dd, J=12.1 Hz, 2.2 Hz), 4.06 (2H, t, J=5.5 Hz), 5.18 (1H, d, J=8.0 Hz), 6.8-6.9 (2H, m), 6.95 (1H, d, J=8.2 Hz), 7.08 (1H, d, J=8.2 Hz), 7.1-7.15 (2H, m), 7.18 (1H, t, J=8.2 Hz), 7.24 (1H, s)

Example 27

4-(β-D-Glucopyranosyloxy)-3-[2-(4-{2-[2-hydroxy-1-(hydroxymethyl)ethylamino]ethoxy}phenyl)ethyl]benzofuran The title compound was prepared in a similar manner to that described in Example 21 using 4-(2,3,4,6-tetra-O-acetyl-β-D-glucopyranosyloxy)-3-{2-[4-(2-hydroxyethoxy)phenyl]ethyl}benzofuran and 2-amino-1,3-propanediol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 2.7-2.8 (1H, m), 2.85-3.1 (5H, m), 3.1-3.25 (1H, m), 3.35-3.7 (8H, m), 3.71 (1H, dd, J=11.9 Hz, 5.7 Hz), 3.9 (1H, dd, J=11.9 Hz, 2.1 Hz), 4.07 (2H, t, J=5.3 Hz), 5.18 (1H, d, J=8.1 Hz), 6.8-6.9 (2H, m), 6.95 (1H, d, J=8.1 Hz), 7.08 (1H, d, J=8.1 Hz), 7.1-7.15 (2H, m), 7.18 (1H, t, J=8.1 Hz), 7.24 (1H, s)

Example 28

4-(β-D-Glucopyranosyloxy)-3-[2-(4-{2-[2-hydroxy-1-(hydroxymethyl)-1-(methyl)ethylamino]ethoxy}phenyl)ethyl]benzofuran The title compound was prepared in a similar manner to that described in Example 21 using 4-(2,3,4,6-tetra-O-acetyl-β-D-glucopyranosyloxy)-3-(2-[4-(2-hydroxyethoxy)phenyl]ethyl)benzofuran and 2-amino-2-methyl-1,3-propanediol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 1.02 (3H, s), 2.85-3.1 (5H, m), 3.1-3.25 (1H, m), 3.35-3.65 (8H, m), 3.71 (1H, dd, J=12.0 Hz, 5.8 Hz), 3.9 (1H, dd, J=12.0 Hz, 2.2 Hz), 4.04 (2H, t, J=5.1 Hz), 5.18 (1H, d, J=7.5 Hz), 6.8-6.9 (2H, m), 6.95 (1H, d, J=8.0 Hz), 7.08 (1H, d, J=8.0 Hz), 7.1-7.15 (2H, m), 7.18 (1H, t, J=8.0 Hz), 7.24 (1H, s)

Example 29

4-(β-D-Glucopyranosyloxy)-3-[2-(4-{2-[2-hydroxy-1,1-di(methyl)ethylamino]ethoxy}phenyl)ethyl]benzofuran The title compound was prepared in a similar manner to that described in Example 21 using 4-(2,3,4,6-tetra-O-acetyl-β-D-glucopyranosyloxy)-3-{2-[4-(2-hydroxyethoxy)phenyl]ethyl}benzofuran and 2-amino-2-methyl-1-propanol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 1.08 (6H, s), 2.85-3.1 (5H, m), 3.1-3.25 (1H, m), 3.3-3.55 (5H, m), 3.55-3.65 (1H, m), 3.71 (1H, dd, J=12.1 Hz, 5.8 Hz), 3.9 (1H, dd, J=12.1 Hz, 2.2 Hz), 4.05 (2H, t, J=5.3 Hz), 5.18 (1H, d, J=7.9 Hz), 6.8-6.9 (2H, m), 6.95 (1H, d, J=8.1 Hz), 7.08 (1H, d, J=8.1 Hz), 7.1-7.15 (2H, m), 7.18 (1H, t, J=8.1 Hz), 7.24 (1H, s)

Example 30

4-(β-D-Glucopyranosyloxy)-3-[2-(3-(2-[2-hydroxy-1-(hydroxymethyl)ethylamino]ethoxy)phenyl)ethyl]benzofuran The title compound was prepared in a similar manner to that described in Example 21 using 4-(2,3,4,6-tetra-O-acetyl-β-D-glucopyranosyloxy)-3-{2-[3-(2-hydroxyethoxy)phenyl]ethyl}benzofuran and 2-amino-1,3-propanediol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 2.7-2.8 (1H, m), 2.85-3.1 (5H, m), 3.1-3.25 (1H, m), 3.4-3.7 (8H, m), 3.72 (1H, dd, J=12.0 Hz, 5.7 Hz), 3.9 (1H, dd, J=12.0 Hz, 2.2 Hz), 4.0-4.15 (2H, m), 5.2 (1H, d, J=7.5 Hz), 6.7-6.9 (3H, m), 6.96 (1H, d, J=8.2 Hz), 7.09 (1H, d, J=8.2 Hz), 7.1-7.25 (2H, m), 7.3 (1H, s)

Example 31

4-(β-D-Glucopyranosyloxy)-3-[2-(3-{2-[2-hydroxy-1-(hydroxymethyl)-1-(methyl)ethylamino]ethoxy}phenyl)ethyl]benzofuran The title compound was prepared in a similar manner to that described in Example 21 using 4-(2,3,4,6-tetra-O-acetyl-β-D-glucopyranosyloxy)-3-{2-[3-(2-hydroxyethoxy)phenyl]ethyl}benzofuran and 2-amino-2-methyl-1,3-propanediol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 1.03 (3H, s), 2.85-3.1 (5H, m), 3.1-3.25 (1H, m), 3.35-3.55 (7H, m), 3.55-3.65 (1H, m), 3.65-3.75 (1H, m), 3.85-3.95 (1H, m), 3.95-4.1 (2H, m), 5.19 (1H, d, J=7.6 Hz), 6.65-6.9 (3H, m), 6.96 (1H, d, J=8.3 Hz), 7.09 (1H, d, J=8.4 Hz), 7.1-7.25 (2H, m), 7.3 (1H, s)

Example 32

4-(β-D-Glucopyranosyloxy)-3-[2-(3-{2-[2-hydroxy-1,1-di(methyl)ethylamino]ethoxy}phenyl)ethyl]benzofuran The title compound was prepared in a similar manner to that described in Example 21 using 4-(2,3,4,6-tetra-O-acetyl-β-D-glucopyranosyloxy)-3-{2-[3-(2-hydroxyethoxy)phenyl]ethyl}benzofuran and 2-amino-2-methyl-1-propanol instead of 4-(2,3,4,6-tetra-O-acetyl-β-D-glucopyranosyloxy)-3-{2-[4-(3-hydroxypropoxy)phenyl]ethyl}benzofuran and 2-aminoethanol, respectively.

$^1$H-NMR (CD$_3$OD) δ ppm: 1.08 (6H, s), 2.85-3.25 (6H, m), 3.35-3.55 (5H, m), 3.55-3.65 (1H, m), 3.72 (1H, dd, J=11.9 Hz, 5.7 Hz), 3.9 (1H, dd, J=11.9 Hz, 2.2 Hz), 3.95-4.1 (2H, m), 5.19 (1H, d, J=7.7 Hz), 6.65-6.9 (3H, m), 6.96 (1H, d, J=7.6 Hz), 7.08 (1H, d, J=8.2 Hz), 7.1-7.25 (2H, m), 7.29 (1H, s)

Reference Example 33

3-(2-[4-(2-Carboxyethyl)phenyl]ethyl)-4-hydroxybenzofuran

To a suspension of 6'-hydroxy-2'-(methoxycarbonylmethoxy)acetophenone (1 g) and 4-formylcinnamic acid (0.79 g) in ethanol (10 mL) were added water (2 mL) and potassium hydroxide (3 g), and the mixture was stirred at room temperature overnight. To the reaction mixture was added 10% palladium-carbon powder (0.2 g), and the mixture was stirred at room temperature under a hydrogen atmosphere overnight. The insoluble material was removed by filtration. The solvent of the filtrate was removed under reduced pressure. To the residue was added 2 mol/L hydrochloric acid, and the precipitated crystals were collected by filtration. The crystals were washed with water and dried under reduced pressure to give 4-(2-carboxyethyl)-2'-(carboxymethoxy)-6'-hydroxydihydrochalcone (1.55 g). This material was dissolved in acetic acid (12 mL). To the solution were added sodium acetate (8.6 g) and acetic anhydride (8.6 mL), and the mixture was stirred at 115° C. overnight. The reaction mixture was poured into water, and the resulting mixture was extracted with diethyl ether. The extract was washed with water twice. To the extract was added 1 mol/L aqueous sodium hydroxide solution, and the aqueous layer was separated. The aqueous layer was acidified by addition of 2 mol/L hydrochloric acid, and the resulting mixture was extracted with diethylether. The extract was washed with brine and dried over anhydrous magnesium sulfate. The solvent was removed under reduced pressure, and the residue was purified by column chromatography on silica gel (eluent: n-hexane/ethyl acetate=1/1) to give the title compound (0.29 g).

$^1$H-NMR (DMSO-$d_6$) δ ppm: 2.45-2.55 (2H, m), 2.75-2.85 (2H, m), 2.85-3.0 (4H, m), 6.6 (1H, dd, J=8.0 Hz, 0.7 Hz), 6.93 (1H, dd, J=8.0 Hz, 0.7 Hz), 7.05 (1H, t, J=8.0 Hz), 7.1-7.2 (4H, m), 7.5 (1H, s), 9.9 (1H, s), 12.08 (1H, s)

Example 33

3-[2-(4-{2-[1-Carbamoyl-1-(methyl)ethylcarbamoyl] ethyl}-phenyl)ethyl]-4-(β-D-glucopyranosyloxy) benzofuran To a solution of 3-{2-[4-(2-carboxyethyl)phenyl]ethyl}-4-hydroxybenzofuran (50 mg) in N,N-diemthylformamide (1 mL) were added 2-amino-2-methylpropionamide (33 mg), 1-hydroxybenzotriazole (33 mg), triethylamine (0.047 mL) and 1-ethyl-3-(3-dimethylaminopropyl)carbodiimide hydrochloride (93 mg), and the mixture was stirred at room temperature overnight. The reaction mixture was poured into water, and the resulting mixture was extracted with ethyl acetate. The organic layer was washed with water, a saturated aqueous sodium hydrogen carbonate solution, water and brine successively, and dried over anhydrous magnesium sulfate. The solvent was removed under reduced pressure, and the residue was dissolved in dichloromethane (5 mL). To the solution was added 2,3,4,6-tetra-O-acetyl-1-O-trichloroacetoimidoyl-α-D-glucopyranose (0.12 g). Then boron trifluoride-diethyl ether complex (0.032 mL) was added to the mixture under ice-cooling, and the mixture was stirred at room temperature for 30 minutes. The reaction mixture was purified by column chromatography on silica gel (eluent: n-hexane/ethyl acetate=1/1-dichloromethane/methanol=20/1) to give 4-(2,3,4,6-tetra-O-acetyl-β-D-glucopyranosyloxy)-3-[2-(4-{2-[1-carbamoyl-1-(methyl)ethylcarboamoyl] ethyl}phenyl)ethyl]benzofuran (57 mg). This material was dissolved in methanol (2 mL). To the solution was added sodium methoxide (28% methanol solution, 0.015 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (36 mg).

$^1$H-NMR (CD$_3$OD) δ ppm: 1.36 (3H, s), 1.37 (3H, s), 2.47 (2H, t, J=7.6 Hz), 2.86 (2H, t, J=7.6 Hz), 2.9-3.1 (3H, m), 3.1-3.25 (1H, m), 3.35-3.45 (1H, m), 3.45-3.55 (2H, m), 3.55-3.65 (1H, m), 3.71 (1H, dd, J=12.0 Hz, 5.8 Hz), 3.91 (1H, dd, J=12.0 Hz, 2.2 Hz), 5.18 (1H; d, J=7.8 Hz), 6.96 (1H, d, J=8.1 Hz), 7.05-7.25 (6H, m), 7.26 (1H, s)

Reference Example 34

3-[2-(4-Acetylaminophenyl)ethyl]-4-hydroxybenzofuran

To a mixture of 6'-hydroxy-2'-(methoxycarbonylmethoxy) acetophenone (2.24 g) and 4-acetylaminobenzaldehyde (2.45 g) in ethanol (30 mL) were added water (10 mL) and potassium hydroxide (6.73 g), and the mixture was stirred at room temperature overnight. To the reaction mixture was added 2 mol/L hydrochloric acid (70 mL), and the precipitated crystals were collected by filtration. The crystals were washed with water and dried under reduced pressure to give 4-acetylamino-2'-(carboxymethoxy)-6'-hydroxychalcone (3.35 g). A mixture of the obtained 4-acetylamino-2'-(carboxymethoxy)-6'-hydroxychalcone (3.3 g) and 10% palladium-carbon powder (1 g) in methanol (50 mL) was stirred at room temperature under a hydrogen atmosphere overnight. The insoluble material was removed by filtration. The solvent of the filtrate was removed under reduced pressure, and the residue was dissolved in acetic acid (13.2 mL). To the solution were added sodium acetate (4.77 g) and acetic anhydride (4.8 mL), and the mixture was stirred at 115° C. for 20 hours. The reaction mixture was poured in to water, and the resulting mixture was extracted with ethyl acetate. The extract was washed with water and brine, and dried over anhydrous sodium sulfate. The solvent was removed under reduced pressure, and the residue was dissolved in methanol (10 mL). To the solution was added sodium methoxide (28% methanol solution, 5 mL), and the mixture was stirred at room temperature for 1 hour. The reaction mixture was concentrated under reduced pressure. To the residue were added 1 mol/L hydrochloric acid (30 mL) and ethyl acetate, and the mixture was stirred for 1 hour. The reaction mixture was poured into a saturated aqueous sodium hydrogen carbonate solution, and the resulting mixture was extracted with ethyl acetate. The extract was washed with brine and dried over anhydrous sodium sulfate. The solvent was removed under reduced pressure, and the residue was treated with dichloromethane-methanol. The precipitated crystals were collected by filtration. The crystals were washed with dichloromethane and dried under reduced pressure to give the title compound (0.86 g).

$^1$H-NMR (CD$_3$OD) δ ppm: 2.1 (3H, s), 2.95-3.05 (4H, m), 6.56 (1H, dd, J=7.8 Hz, 0.6 Hz), 6.88 (1H, dd, J=8.4 Hz, 0.6 Hz), 7.0-7.05 (1H, m), 7.1-7.2 (2H, m), 7.21 (1H, s), 7.35-7.45 (2H, m)

Example 34

3-[2-(4-Acetylaminophenyl)ethyl]-4-(β-D-glucopyranosyloxy)benzofuran

To a mixture of 3-[2-(4-acetylaminophenyl)ethyl]-4-hydroxybenzofuran (30 mg) and 2,3,4,6-tetra-O-acetyl-1-O-trichloroacetoimidoyl-α-D-glucopyranose (64 mg) in dichloromethane (3 mL) was added boron trifluoride-diethyl ether complex (0.013 mL), and the mixture was stirred at room temperature for three days. The reaction mixture was poured into a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: n-hexane/ethyl acetate=2/3-1/2) to give 3-[2-(4-acetylaminophenyl)ethyl]-4-(2,3,4,6-tetra-O-acetyl-β-D-glucopyranosyloxy)benzofuran (38 mg). This material was dissolved in methanol (3 mL). To the solution was added sodium methoxide (28% methanol solution, 0.02 mL), and the mixture was stirred at room temperature for 2 hours. The reaction mixture was concentrated under reduced pressure, and the residue was purified by column chromatography on silica gel (eluent: dichloromethane/methanol=6/1) to give the title compound (12 mg).

$^1$H-NMR (CD$_3$OD) δ ppm: 2.1 (3H, s), 2.9-3.6 (8H, m), 3.71 (1H, dd, J=12.1 Hz, 5.5 Hz), 3.9 (1H, dd, J=12.1 Hz, 2.3 Hz), 5.18 (1H, d, J=7.4 Hz), 6.96 (1H, d, J=8.0 Hz), 7.08 (1H, d, J=8.0 Hz), 7.15-7.2 (3H, m), 7.27 (1H, s), 7.35-7.45 (2H, m)

Reference Example 35

3-[2-(4-Aminophenyl)ethyl]-4-hydroxybenzofuran

A mixture of 3-[2-(4-acetylaminophenyl)ethyl]-4-hydroxybenzofuran (1.2 g) and n-propanol (4 mL)-5 mol/L aqueous sodium hydroxide solution (8 mL) was heated for reflux overnight. The reaction mixture was cooled to room temperature. To the reaction mixture was added 2 mol/L hydrochloric acid (21 mL). The mixture was poured into a saturated aqueous sodium hydrogen carbonate solution, and the resulting mixture was extracted with ethylacetate. The extract was washed with brine, and dried over anhydrous sodium sulfate. The solvent was removed under reduced pressure, and the residue was treated with ethyl acetate. The precipitated crystals were collected by filtration and dried under reduced pressure to give the title compound (0.51 g).

$^1$H-NMR (CD$_3$OD) δ ppm: 2.85-3.0 (4H, m), 6.55 (1H, dd, J=8.0 Hz, 0.7 Hz), 6.65-6.7 (2H, m), 6.87 (1H, dd, J=8.2 Hz, 0.7 Hz), 6.95-7.0 (2H, m), 7.0-7.05 (1H, m), 7.19 (1H, s)

Example 35

4-(β-D-Glucopyranosyloxy)-3-[2-(4-methanesulfonylaminophenyl)ethyl]benzofuran

To a mixture of 3-[2-(4-aminophenyl)ethyl]-4-hydroxybenzofuran (0.3 g) and 2,3,4,6-tetra-o-acetyl-1-O-trichloroacetoimidoyl-α-D-glucopyranose (0.65 g) in dichloromethane (5 mL) was added borontrifluoride-diethyl ether complex (0.23 mL), and the mixture was stirred at room temperature overnight. The reaction mixture was poured into a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: n-hexane/ethyl acetate=1/1-1/2-1/5) to give 3-[2-(4-aminophenyl)ethyl]-4-(2,3,4,6-tetra-O-acetyl-β-D-glucopyranosyloxy)benzofuran (0.36 g). To a solution of the obtained 3-[2-(4-aminophenyl)ethyl]-4-(2,3,4,6-tetra-O-acetyl-β-D-glucopyranosyloxy)benzofuran (50 mg) in dichloromethane (3 mL) were added pyridine (0.017 mL) and methanesulfonyl chloride (0.013 mL), and the mixture was stirred at room temperature for 1 hour. The reaction mixture was poured into 0.5 mol/L hydrochloric acid, and the resulting mixture was extracted with ethyl acetate. The extract was washed with a saturated aqueous sodium hydrogen carbonate solution and brine, and dried over anhydrous sodium sulfate. The solvent was removed under reduced pressure, and the residue was purified by VARIAN BOND ELUT-SCX (eluent: methanol) to give 4-(2,3,4,6-tetra-O-acetyl-β-D-glucopyranosyloxy)-3-[2-(4-methanesulfonylaminophenyl)ethyl]benzofuran (40 mg). This material was dissolved in methanol (3 mL). To the solution was added sodium methoxide (28% methanol solution, 0.02 mL), and the mixture was stirred at room temperature for 2 hours. The reaction mixture was concentrated under reduced pressure. To the residue was added a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: dichloromethane/methanol=8/1) to give the title compound (19 mg).

$^1$H-NMR (CD$_3$OD) δ ppm: 2.91 (3H, s), 2.95-3.25 (4H, m), 3.4-3.6 (4H, m), 3.71 (1H, dd, J=12.3 Hz, 5.7 Hz), 3.9 (1H, dd, J=12.3 Hz, 2.3 Hz), 5.18 (1H, d, J=7.9 Hz), 6.96 (1H, d, J=8.1 Hz), 7.08 (1H, d, J=8.2 Hz), 7.1-7.25 (5H, m), 7.28 (1H, s)

Example 36

3-[2-(4-Formylaminophenyl)ethyl]-4-(β-D-Glucopyranosyloxy)benzofuran

The title compound was prepared in a similar manner to that described in Example 35 using acetic acid-formic acid anhydride instead of methanesulfonyl chloride.

$^1$H-NMR (CD$_3$OD) δ ppm: 2.9-3.25 (4H, m), 3.4-3.65 (4H, m), 3.71 (1H, dd, J=12.0 Hz, 5.6 Hz), 3.85-3.95 (1H, m), 5.19 (1H, d, J=7.9 Hz), 6.96 (1H, d, J=8.1 Hz), 7.0-7.5 (7H, m), 8.22 (0.75H, s), 8.63 (0.25H, s)

Example 37

4-(β-D-Glucopyranosyloxy)-3-[2-(4-ureidophenyl) ethyl]-benzofuran

To a mixture of 3-[2-(4-aminophenyl)ethyl-4-hydroxybenzofuran (0.3 g) and 2,3,4,6-tetra-O-acetyl-1-O-trichloroacetoimidoyl-α-D-glucopyranose (0.65 g) in dichloromethane (5 mL) was added borontrifluoride-diethyl ether complex (0.23 mL), and the mixture was stirred at room temperature overnight. The reaction mixture was poured into a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: n-hexane/ethyl acetate=1/1-1/2-1/5) to give 3-[2-(4-aminophenyl)-ethyl]-4-(2,3,4,6-tetra-O-acetyl-β-D-glucopyranosyloxy)benzofuran (0.36 g). To a solution of the obtained 3-[2-(4-aminophenyl)ethyl]-4-(2,3,4,6-tetra-O-acetyl-β-D-glucopyranosyloxy)benzofuran (50 mg) in tetrahydrofuran (2 mL) was added trimethylsilyl isocyanate (0.014 mL), and the mixture was stirred at room temperature overnight. To the reaction mixture was added water (0.3 mL), and the mixture was stirred at 50° C. for 2 hours. The reaction mixture was poured into 0.5 mol/L hydrochloric acid, and the resulting mixture was extracted with ethyl acetate. The extract was washed with a saturated aqueous sodium hydrogen carbonate solution and brine, and dried over anhydrous sodium sulfate. The solvent was removed under reduced pressure, and the residue was purified by VARIAN BOND ELUT-SCX (eluent: methanol) to give 4-(2,3,4,6-tetra-O-acetyl-β-D-glucopyranosyloxy)-3-[2-(4-ureidophenyl)ethyl]-benzofuran (20 mg). This material was dissolved in methanol (3 mL). To the solution was added sodium methoxide (28% methanol solution, 0.02 mL), and the mixture was stirred at room temperature for 2 hours. The reaction mixture was concentrated under reduced pressure. To the residue was added a saturated aqueous sodium hydrogen carbonate solution, and the mixture was extracted with ethyl acetate. The extract was washed with brine and dried over anhydrous sodium sulfate. The solvent was removed under reduced pressure, and the residue was purified by column chromatography on silica gel (eluent: dichlorometane/methanol=5/1) to give the title compound (4 mg).

$^1$H-NMR (CD$_3$OD) δ ppm: 2.9-3.25 (4H, m), 3.4-3.65 (4H, m), 3.71 (1H, dd, J=12.1 Hz, 5.7 Hz), 3.9 (1H, dd, J=12.1 Hz, 2.2 Hz), 5.18 (1H, d, J=7.7 Hz), 6.96 (1H, d, J=8.2 Hz), 7.05-7.3 (7H, m)

Reference Example 36

3-[2-(4-Bromophenyl)ethyl]-4-hydroxybenzofuran

To a mixture of 6'-hydroxy-2'-(methoxycarbonylmethoxy)acetophenone (2.24 g) and 4-bromobenzaldehyde (2.78 g) in ethanol (30 mL) were added water (10 mL) and potassium hydroxide (6.73 g), and the mixture was stirred at room temperature overnight. To the reaction mixture was added 2 mol/L hydrochloric acid (70 mL), and the precipitated crystals were collected by filtration. The crystals were washed with water and dried under reduced pressure to give 4-bromo-2'-(carboxymethoxy)-6'-hydroxychalcone (3.77 g). To a suspension of the obtained 4-bromo-2'-(carboxymethoxy)-6'-hydroxychalcone (3.7 g) in benzene (150 mL) were added tris(triphenylphosphine)rhodium(I) chloride (1.82 g) and triethylsilane (6.2 mL), and the mixture was stirred at 70° C. overnight. To the reaction mixture were added 2 mol/L aqueous sodium hydroxide solution and diethyl ether, and the aqueous layer was separated. The aqueous layer was washed with diethyl ether and acidified by addition of concentrated hydrochloric acid, and the mixture was extracted with ethyl acetate. The extract was washed with water and brine, and dried over anhydrous sodium sulfate. The solvent was removed under reduced pressure, and the residue was treated with n-hexane-ethyl acetate. The precipitated crystals were collected by filtration. The crystals were washed with n-hexane and dried under reduced pressure to give 4-bromo-2'-(carboxymethoxy)-6'-hydroxydihydrochalcone (1.1 g). This material was dissolved in acetic acid (4.15 mL). To the solution were added sodium acetate (1.5 g) and acetic anhydride (1.5 mL), and the mixture was stirred at 115° C. overnight. The reaction mixture was poured into water, and the resulting mixture was extracted with ethyl acetate. The extract was washed with water and brine, and dried over anhydrous sodium sulfate. The solvent was removed under reduced pressure, and the residue was dissolved in methanol (10 mL). To the solution was added sodium methoxide (28% methanol solution, 1.5 mL), and the mixture was stirred at room temperature for 1 hour. The reaction mixture was concentrated under reduced pressure. To the residue was added 1 mol/L hydrochloric acid, and the mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=5/1) to give the title compound (0.85 g).

$^1$H-NMR (CDCl$_3$) δ ppm: 2.95-3.1 (4H, m), 5.03 (1H, s), 6.54 (1H, dd, J=7.6 Hz, 1.1 Hz), 7.05-7.15 (4H, m), 7.19 (1H, s), 7.35-7.45 (2H, m)

Reference Example 37

3-(2-{4-[1-Amino-1-(benzyloxycarbonylimino)methyl]phenyl}ethyl)-4-hydroxybenzofuran A suspension of 3-[2-(4-bromophenyl)ethyl]-4-hydroxybenzofuran (0.5 g), sodium cyanide (0.23 g), tetrakis(triphenylphosphine)palladium (0) (91 mg) and copper (I) iodide (30 mg) in acetonitrile (5 mL) was heated for reflux for three days. To the reaction mixture was added water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=5/1) to give 3-[2-(4-cyanophenyl)ethyl]-4-hydroxybenzofuran (0.14 g). To a solution of hexamethyldisilazane (0.35 mL) in diethyl ether (2 mL) was added n-butyl lithium (2.46 mol/L n-hexane solution 0.7 mL) under ice-cooling, and the mixture was stirred at the same temperature for 10 minutes. To the reaction mixture was added a solution of the 3-[2-(4-cyanophenyl)ethyl]-4-hydroxybenzofuran (0.13 g) in diethyl ether (3 ml), and the mixture was stirred at room temperature for 2 hours. To the reaction mixture was added 2 mol/L hydrochloric acid, and the resulting mixture was washed with diethyl ether twice. The aqueous layer was basified by addition of 2 mol/L aqueous sodium hydroxide solution, and the mixture was poured into a saturated aqueous sodium hydrogen carbonate solution. The resulting mixture was extracted with a mixed solvent of dichlorometane and methanol (5/1) (three times), and the extract was dried over anhydrous magnesium sulfate. The solvent was removed under reduced pressure to give 3-[2-(4-carbamimidoylphenyl)ethyl]-4-hydroxybenzofuran (0.11 g). This material was dissolved in 1,4-dioxane (5 mL)-1 mol/L aqueous sodium hydroxide solution (5 mL). To the solution was added benzyl chloroformate (0.1 mL), and the mixture was stirred at room temperature overnight. To the reaction mixture was added 1 mol/L hydrochloric acid (5 mL), and the mixture was poured into a saturated aqueous sodium hydrogen carbonate solution. The resulting mixture was extracted with ethyl acetate. The extract was washed with brine and dried over anhydrous sodium sulfate. The solvent was removed under reduced pressure, and the residue was purified by column chromatography on silica gel (eluent: n-hexane/ethyl acetate=2/1) to give the title compound (35 mg).

$^1$H-NMR (CDCl$_3$) δ ppm: 3.0-3.05 (4H, m), 4.71 (1H, d, J=5.8 Hz), 5.23 (2H, s), 5.85 (1H, brs), 6.58 (1H, dd, J=7.5 Hz, 0.8 Hz), 7.0-7.1 (2H, m), 7.16 (1H, s), 7.2-7.5 (8H, m), 7.75-7.8 (2H, m)

Example 38

3-[2-(4-Carbamimidoylphenyl)ethyl]-4-(β-D-glucopyranosyloxy)benzofuran

To a mixture of 3-(2-{4-[1-amino-1-(benzyloxycarbonylimino)methyl]phenyl}ethyl)-4-hydroxybenzofuran (30 mg) and 2,3,4,6-tetra-O-acetyl-1-O-trichloroacetoimidoyl-α-D-glucopyranose (43 mg) in dichloromethane (3 mL) was added boron trifluoride-diethyl ether complex (0.009 mL), and the mixture was stirred at room temperature for 3 days. The reaction mixture was poured into a saturated aqueous sodium hydrogen carbonate solution, and the resulting mixture was extracted with ethyl acetate. The extract was washed with brine and dried over anhydrous sodium sulfate. The solvent was removed under reduced pressure, and the residue was purified by column chromatography on silica gel (eluent: n-hexane/ethyl acetate=1/1-2/3) to give 4-(2,3,4,6-tetra-O-acetyl-β-D-glucopyranosyloxy)-3-(2-{4-[1-amino-1-(benzyloxycarbonylimino)methyl]phenyl}ethyl)benzofuran (42 mg). This material was dissolved in methanol (3 mL). To the solution was added sodium methoxide (28% methanol solution, 0.02 mL), and the mixture was stirred at room temperature for 1 hour. To the reaction mixture was added a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: dichloromethane/methanol=10/1) to give 3-(2-{4-[1-amino-1-(benzyloxycarbonylimino)methyl]phenyl}ethyl)-4-(β-D-glucopyranosyloxy)benzofuran (20 mg). This material was dissolved in methanol (3 mL). To the solution was added 10% palladium-carbon powder (10 mg), and the mixture was stirred at room temperature under a hydrogen atmosphere for 2 hours. The insoluble material was removed by filtration. The solvent of the filtrate was removed under reduced pressure to give the title compound (13 mg).

$^1$H-NMR (CD$_3$OD) δ ppm: 3.05-3.6 (8H, m), 3.72 (1H, dd, J=12.1 Hz, 5.5 Hz), 3.91 (1H, dd, J=12.1 Hz, 1.9 Hz), 5.2 (1H, d, J=7.1 Hz), 6.98 (1H, d, J=8.2 Hz), 7.08 (1H, d, J=8.2 Hz), 7.2 (1H, t, J=8.2 Hz), 7.27 (1H, s), 7.41 (2H, d, J=8.2 Hz), 7.67 (2H, d, J=8.2 Hz)

Reference Example 38

3-[2-(4-Carboxyphenyl)ethyl]-4-hydroxybenzofuran

To a mixture of 2'-benzyloxy-6'-hydroxyacetophenone (2.42 g) and methyl 4-formylbenzoate (2.46 g) in ethanol (50 mL) were added water (15 mL) and potassium hydroxide (6.73 g), and the mixture was stirred at 50° C. overnight. To the reaction mixture was added 2 mol/L hydrochloric acid (70 mL), and the precipitated crystals were collected by filtration. The crystals were washed with water and dried under reduced pressure to give 2'-benzyloxy-4-carboxy-6'-hydroxychalcone (3.55 g). This material was dissolved in N,N-dimethylformamide (35 mL). To the solution were added potassium carbonate (3.88 g) and methyl bromoacetate (1.95 mL), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was dissolved in methanol (20 mL)-ethyl acetate (10 mL). To the solution was added 10% palladium-carbon powder (1 g), and the mixture was stirred at room temperature under a hydrogen atmosphere for 7 hours. The insoluble material was removed by filtration. The solvent of the filtrate was removed under reduced pressure, and the residue was treated with n-hexane. The precipitated crystals were collected by filtration and dried under reduced pressure to give 6'-hydroxy-2'-(methoxycarbonylmethoxy)-4-(methoxycarbonylme thoxycarbonyl)dihydrochalcone (2.56 g). This material was suspended in methanol (17 mL). To the suspension was added sodium methoxide (28% methanol solution, 3.35 mL), and the mixture was heated for ref lux overnight. The reaction mixture was cooled to room temperature. To the mixture was added 1 mol/L hydrochloric acid (30 mL), and the resulting mixture was extracted with ethyl acetate. The extract was washed with water and brine, and dried over anhydrous sodium sulfate. The solvent was removed under reduced pressure. To the residue were added methanol (25 mL) and 2 mol/L aqueous sodium hydroxide solution (50 mL), and the mixture was stirred at 60° C. overnight. The reaction mixture was cooled to room temperature. To the mixture were added 2 mol/L hydrochloric acid (55 mL) and water (50 mL), and the mixture was stirred at room temperature for 1 hour. The precipitated crystals were collected by filtration, washed with water and dried under reduced pressure to give 2-carboxy-3-[2-(4-carboxyphenyl) ethyl]-4-hydroxybenzofuran (1.45 g). This material was suspended in quinoline (12 mL). To the suspension was added a catalytic amount of copper powder, and the mixture was stirred at 200° C. for 1 hour. The reaction mixture was cooled to room temperature. To the mixture were added 1 mol/L hydrochloric acid and ethyl acetate, and the insoluble material was removed by filtration. The organic layer was separated from the filtrate. The organic layer was washed with water and brine, and dried over anhydrous sodium sulfate. The solvent was removed under reduced pressure, and the residue was purified by column chromatography on silica gel (eluent dichloromethane/methanol=20/1) to give the title compound (80 mg).

$^1$H-NMR (CD$_3$OD) δ ppm: 3.0-3.15 (4H, m), 6.55-6.6 (1H, m), 6.85-6.9 (1H, m), 7.0-7.1 (1H, m), 7.23 (1H, s), 7.3-7.35 (2H, m), 7.9-7.95 (2H, m)

Reference Example 39

3-[2-(4-Carbamoylphenyl)ethyl]-4-hydroxybenzofuran

To a mixture of 3-[2-(4-carboxyphenyl)ethyl]-4-hydroxybenzofuran (80 mg), ammonium hydrogen carbonate (90 mg) and pyridine (0.091 mL) in N,N-dimethylformamide (3 mL) was added ditert-butyl dicarbonate (0.25 g), and the mixture was stirred at room temperature overnight. To the reaction mixture was added 0.5 mol/L hydrochloric acid, and the resulting mixture was extracted with ethyl acetate. The extract was washed with water, a saturated aqueous sodium hydrogen carbonate solution and brine successively, and dried over anhydrous sodium sulfate. The solvent was removed under reduced pressure, and the residue was dissolved in methanol (5 mL). To the solution was added sodium methoxide (28% methanol solution, 0.1 mL), and the mixture was stirred at 50° C. for 3 hours. The reaction mixture was cooled to room temperature. To the mixture was added 1 mol/L hydrochloric acid (0.52 mL), and the resulting mixture was concentrated under reduced pressure, and the residue was purified by column chromatography on silica gel (eluent: dichloromethane/methanol=30/1) and VARIAN BOND ELUT-SAX (eluent: methanol) successively to give the title compound (50 mg).

$^1$H-NMR (CD$_3$OD) δ ppm: 3.0-3.15 (4H, m), 6.57 (1H, dd, J=7.9 Hz, 0.6 Hz), 6.88 (1H, dd, J=8.2 Hz, 0.6 Hz), 7.0-7.1 (1H, m), 7.21 (1H, s), 7.25-7.35 (2H, m), 7.75-7.8 (2H, m)

Example 39

3-[2-(4-Carbamoylphenyl)ethyl]-4-(β-D-glucopyranosyloxy)benzofuran

To a mixture of 3-[2-(4-carbamoylphenyl)ethyl]-4-hydroxybenzofuran (50 mg) and 2,3,4,6-tetra-O-acetyl-1-O-trichloroacetoimidoyl-α-D-glucopyranose (96 mg) in dichloromethane (3 mL) was added borontrifluoride-diethyl ether complex (0.022 mL), and the mixture was stirred at room temperature overnight. The reaction mixture was poured into a saturated aqueous sodium hydrogen carbonate solution, and the resulting mixture was extracted with ethylacetate. The extract was washed with brine and dried over anhydrous sodium sulfate. The solvent was removed under reduced pressure, and the residue was purified by column chromatography on silica gel (eluent: dichloromethane/methanol=20/1) to give 4-(2,3,4,6-tetra-O-acetyl-β-D-glucopyranosyloxy)-3-[2-(4-carbamoylphenyl)ethyl]benzofuran (80 mg). This material was dissolved in methanol (3 mL). To the solution was added sodium methoxide (28% methanol solution, 0.02 mL), and the mixture was stirred at room temperature for 2 hours. The solvent was removed under reduced pressure. To the residue was added a saturated aqueous sodium hydrogen carbonate solution, and the resulting mixture was extracted with ethyl acetate. The extract was washed with brine and dried over anhydrous sodium sulfate. The solvent was removed under reduced pressure, and the residue was treated with dichloromethane. The precipitated crystals were collected by filtration and dried under reduced pressure to give the title compound (13 mg).

$^1$H-NMR (CD$_3$OD) δ ppm: 3.0-3.6 (8H, m), 3.71 (1H, dd, J=12.0 Hz, 5.8 Hz), 3.91 (1H, dd, J=12.0 Hz, 2.2 Hz), 5.19 (1H, d, J=7.9 Hz), 6.97 (1H, d, J=7.7 Hz), 7.09 (1H, d, J=8.2 Hz), 7.15-7.25 (1H, m), 7.27 (1H, s), 7.3-7.35 (2H, m), 7.75-7.8 (2H, m)

Reference Example 40

6'-Hydroxy-2'-(tetrahydropyran-2-yloxy)acetophenone

2',6'-Dihydroxyacetophenone (5.0 g) was dissolved in dioxane (20 mL) and 3,4-dihydro-2H-pyran (16 mL). To the solution was added p-toluenesulfonic acid monohydrate (0.21 g), and the mixture was stirred at room temperature for 1.5 hours. The reaction mixture was diluted with diethyl ether, and the mixture was washed with 5% aqueous potassium carbonate solution. The organic layer was extracted with 2 mol/L aqueous sodium hydroxide solution, and the aqueous layer was neutralized until pH was about 8. The resulting mixture was extracted with diethyl ether. The organic layer was washed with water and brine, and dried over anhydrous magnesium sulfate to give the title compound (5.64 g).

$^1$H-NMR (CDCl$_3$) δ ppm: 1.6-2.0 (6H, m), 2.75 (3H, s), 3.7-3.75 (1H, m), 3.85-3.95 (1H, m), 5.53 (1H, d, J=2.9 Hz), 6.59 (1H, dd, J=8.4, 1.0 Hz), 6.70 (1H, dd, J=8.4, 1.0 Hz), 7.32 (1H, t, J=8.4 Hz), 13.08 (1H, s)

Example 40

3-[2-(Furan-2-yl)ethyl]-4-(β-D-glucopyranosyloxy)benzofuran

Process 1)

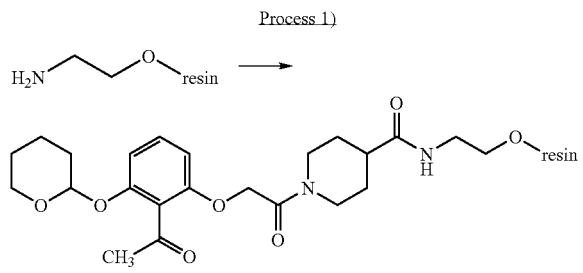

Argogel (registered trademark)-NH$_2$ resin (Argonote: 0.43 mmol/g:5.0 g) was suspended in N,N-dimethylformamide, and the suspension was allowed to stand at room temperature for 30 minutes. The excess solvent was removed. N-9-(Fluorenylmethoxycarbonyl)piperidin-4-carboxylic acid (3.78 g) and 1-hydroxybenzotriazole (1.45 g) were dissolved in N,N-dimethylformamide (50 mL). To the solution was added N,N-diisopropylcarbodiimide (1.68 mL) under ice-cooling, and the mixture was stirred for 10 minutes. The reaction mixture was added to the above resin, and the mixture was stirred at room temperature for 20 hours. The excess solvent was removed, and the resin was washed with dichloromethane (three times), N,N-dimethylformamide (three times) and dichloromethane (three times). The same washing procedure was repeated twice. The obtained resin was treated with a solution of 2% 1,8-diazabicyclo[5.4.0]undec-7-ene in N,N-dimethylformamide at room temperature for 1 hour, and the solvent was removed. The resin was further treated with a solution of 2% 1,8-diazabicyclo[5.4.0]undec-7-ene in N,N-dimethylformamide for 30 minutes, and the solvent was removed. The resin was washed with dichloromethane (three times), N,N-dimethylformamide (three times), dichloromethane (six times), N,N-dimethylformamide (three times) and dichloromethane (three times). The obtained resin was suspended in dichloromethane, and the mixture was allowed to stand at room temperature for 30 minutes. The excess solvent was removed. To a solution of bromoacetic acid (2.99 g) in dichloromethane (25 mL) was added N,N-diisopropylcarbodiimide (1.68 mL), and the mixture was stirred at room temperature for 2 hours. The generated precipitates were removed by filtration, and the filtrate was added to the above resin. To the mixture were added a solution of 4-dimethylaminopyridine (0.026 g) in dichloromethane (1 mL) and N,N-diisopropylethylamine (2.24 mL), and the mixture was stirred at room temperature for 20 hours. The solvent was removed, and the resin was washed with dichloromethane (three times). The same condensing procedure was repeated, and the solvent was removed. The resin was washed with dichloromethane (six times), N,N-dimethylformamide (three times), dichloromethane (six times), N,N-dimethylformamide (three times) and dichloromethane (three times). The obtained resin was suspended in N,N-dimethylformamide, and the mixture was stirred at room temperature for 30 minutes. The excess solvent was removed. A solution of 6'-hydroxy-2'-(tetrahydropyran-2-yloxy)acetophenone (2.03 g) in N,N-dimethylformamide (35 mL) was added to the above resin. To the mixture was added potassium carbonate (2.08 g), and the mixture was stirred at room temperature for 20 hours. The solvent was removed, and the resin was washed with 50% aqueous tetrahydrofuran solution (five times), methanol (three times), N,N-dimethylformamide (three times) and dichloromethane (three times). The resin was dried under reduced pressure.

Process 2)

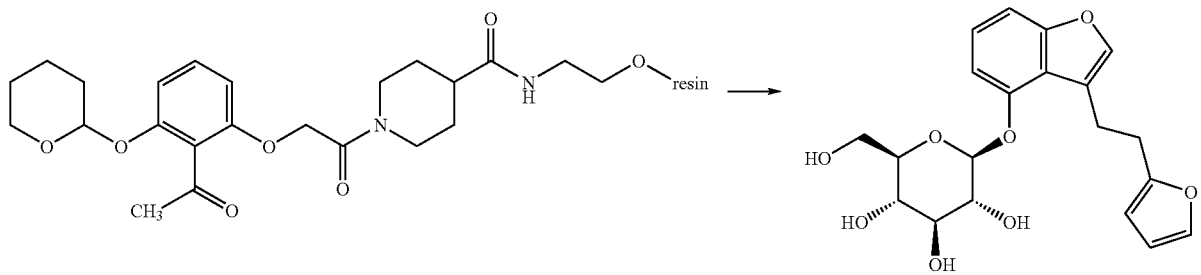

The obtained resin in process 1 (0.70 g) was suspended in ethanol, and the mixture was allowed to stand at room temperature for 30 minutes. The excess solvent was removed. A solution of 2-furaldehyde (0.15 g) in ethanol (5 mL), ethanol (2 mL) and 5 mol/L aqueous potassium hydroxide solution (0.3 mL) were added to the above resin, and the mixture was stirred at room temperature for 15 hours. The solvent was removed, and the resin was washed with methanol (three times), N,N-dimethylformamide (three times) and dichloromethane (six times). The obtained resin was suspended in benzene, and the mixture was allowed to stand at room temperature for 30 minutes. The excess solvent was removed. A suspension of tris(triphenylphosphine)rhodium (I) chloride (0.084 g) in benzene (5 mL), benzene (2 mL) and triethylsilane (0.48 mL) were added to the above resin, and the mixture was stirred at 70° C. for 3 hours. The solvent was removed, and the resin was washed with dichloromethane (five times), N,N-dimethylformamide (five times), methanol (five times) and N,N-dimethylformamide (three times). N,N-Dimethylformamide was added to the obtained resin, and the mixture was stirred for 5 minutes. The excess solvent was removed. A suspension of sodium tert-butoxide (0.087 g) in N,N-dimethylformamide (5 mL) and N,N-dimethylformamide (2 mL) were added to the above resin, and the mixture was stirred at room temperature for 3 hours. To the reaction mixture was added a small amount of water, and the solvent was removed. The resin was washed with N,N-dimethylformamide (three times), dichloromethane (three times), N,N-dimethylformamide (three times) and dichloromethane (three times). The obtained resin was suspended in ethanol, and the mixture was stirred for 30 minutes. The excess solvent was removed. To the resin were added a solution of p-toluenesulfonic acid monohydrate (0.12 g) in ethanol (5 mL) and ethanol (2 mL), and the mixture was stirred at 70° C. for 3 hours. The solvent was removed, and the resin was washed with ethanol (three times), dichloromethane (three times), methanol (three times), N,N-dimethylformamide (three times) and dichloromethane (three times). To the obtained resin were added a solution of 2,3,4,6-tetra-O-acetyl-1-O-trichloroacetoimidoyl-α-D-glucopyranose (0.45 g) in dichloromethane (5 mL), dichloromethane (2 mL) and boron trifluoride-diethyl ether complex (0.11 mL), and the mixture was stirred at room temperature for 8 hours. The solvent was removed, and the resin was washed with dichloromethane (five times), N,N-dimethylformamide (five times) and methanol (five times). The obtained resin was suspended in ethanol, and the mixture was allowed to stand at room temperature for 30 minutes. The excess solvent was removed. To the resin were added ethanol (3.5 mL) and 5 mol/L aqueous potassium hydroxide solution (3.5 mL), and the mixture was stirred at 70° C. for 5 hours. The mixture was further stirred at room temperature for 20 hours. The resin was removed by filtration, and the resin was washed with ethanol. The washing solvents were combined and concentrated, and the residue was suspended in water (10 mL). The mixture was neutralized by addition of citric acid and purified by solid phase extraction on ODS (washing solvent: distilled water, eluent: methanol). The filtrate was concentrated under reduced pressure, and a suspension of the obtained residue and a catalytic amount of copper powder in quinoline (1 mL) was heated at 200° C. for 1 hour. The insoluble material was removed by filtration and washed with methanol. The washing solvents were combined and concentrated under high vacuum pressure using centrifugal evaporator. The residue was purified by preparative reverse phase column chromatography (Shiseido CAPCELL PAK UG5 ODS, 5 μm, 120 Å, 20×50 mm, linear gradient, water/acetonitrile=90/10-10/90), and the fractions were concentrated under reduced pressure to give the title compound (0.006 g).

MS(ESI, m/z): 408 $[M+NH_4]^+$

Example 41

4-(β-D-Glucopyranosyloxy)-3-[2-(2-pyridyl)ethyl]benzofuran

The title compound was prepared in a similar manner to that described in Example 40 using 2-formylpyridine instead of 2-furaldehyde.

MS(ESI, m/z): 402 $[M+H]^+$

Example 42

4-(β-D-Glucopyranosyloxy)-3-[2-(3-pyridyl)ethyl]benzofuran

The title compound was prepared in a similar manner to that described in Example 40 using 3-formylpyridine instead of 2-furaldehyde.

MS(ESI, m/z): 402 $[M+H]^+$

Example 43

4-(β-D-Glucopyranosyloxy)-3-[2-(4-pyridyl)ethyl]benzofuran

The title compound was prepared in a similar manner to that described in Example 40 using 4-formylpyridine instead of 2-furaldehyde.

MS(ESI, m/z): 402 $[M+H]^+$

Example 44

4-(β-D-Glucopyranosyloxy)-3-[2-(4-methoxyphenyl)ethyl]-benzofuran

The title compound was prepared in a similar manner to that described in Example 40 using 4-methoxybenzaldehyde instead of 2-furaldehyde.

MS(ESI, m/z): 448 $[M+NH_4]^+$ $^1$H-NMR (CD$_3$OD) δ ppm: 2.85-3.1 (3H, m), 3.1-3.25 (1H, m), 3.35-3.45 (1H, m), 3.45-3.55 (2H, m), 3.55-3.65 (1H, m), 3.71 (1H, dd, J=12.1 Hz, 5.8 Hz), 3.75 (3H, s), 3.9 (1H, dd, J=12.1 Hz, 2.1 Hz), 5.18 (1H, d, J=7.6 Hz), 6.75-6.85 (2H, m), 6.95 (1H, d, J=8.0 Hz), 7.08 (1H, d, J=8.0 Hz), 7.1-7.15 (2H, m), 7.18 (1H, t, J=8.0 Hz), 7.25 (1H, s)

Example 45

3-[2-(Benzofuran-2-yl)ethyl]-4-(β-D-glucopyranosyloxy)benzofuran

The title compound was prepared in a similar manner to that described in Example 40 using 2-formylbenzofuran instead of 2-furaldehyde.

MS(ESI, m/z): 458 $[M+NH_4]^+$

Example 46

3-[2-(4-Dimethylaminophenyl)ethyl]-4-(β-D-glucopyranosyloxy)benzofuran

The title compound was prepared in a similar manner to that described in Example 40 using 4-dimethylaminobenzaldehyde instead of 2-furaldehyde.
MS(ESI, m/z): 444 [M+H]$^+$

Example 47

3-[2-(4-Carboxyphenyl)ethyl]-4-(β-D-glucopyranosyloxy)benzofuran

The title compound was prepared in a similar manner to that described in Example 40 using methyl 4-formylbenzoate instead of 2-furaldehyde.
MS(ESI, m/z): 462 [M+NH$_4$]$^+$

Example 48

4-(β-D-Glucopyranosyloxy)-3-(2-[3-(phenyl)phenyl]ethyl)benzofuran

The title compound was prepared in a similar manner to that described in Example 40 using 3-phenylbenzaldehyde instead of 2-furaldehyde.
MS(ESI, m/z): 494 [M+NH$_4$]$^+$

Example 49

4-(β-D-Glucopyranosyloxy)-3-[2-(4-methanesulfonylphenyl)ethyl]benzofuran

The title compound was prepared in a similar manner to that described in Example 40 using 4-methanesulfonylbenzaldehyde instead of 2-furaldehyde.
MS(ESI, m/z): 496 [M+NH$_4$]$^+$

Example 50

3-[2-(4-Aminophenyl)ethyl]-4-(β-D-glucopyranosyloxy)benzofuran

The title compound was prepared in a similar manner to that described in Example 40 using 4-acetylaminobenzaldehyde instead of 2-furaldehyde.
MS(ESI, m/z): 416 [M+H]$^+$

Example 51

3-[2-(2-Fluorophenyl)ethyl]-4-(β-D-glucopyranosyloxy)benzofuran

The title compound was prepared in a similar manner to that described in Example 40 using 2-fluorobenzaldehyde instead of 2-furaldehyde.
MS(ESI, m/z): 436 [M+NH$_4$]$^+$

Example 52

3-[2-(3-Fluorophenyl)ethyl]-4-(β-D-glucopyranosyloxy)benzofuran

The title compound was prepared in a similar manner to that described in Example 40 using 3-fluorobenzaldehyde instead of 2-furaldehyde.
MS(ESI, m/z): 436 [M+NH$_4$]$^+$

Example 53

3-[2-(4-Fluorophenyl)ethyl]-4-(β-D-glucopyranosyloxy)benzofuran

The title compound was prepared in a similar manner to that described in Example 40 using 4-fluorobenzaldehyde instead of 2-furaldehyde.
MS(ESI, m/z): 436 [M+NH$_4$]$^+$

Example 54

4-(β-D-Glucopyranosyloxy)-3-[2-(2,4-dimethylphenyl)ethyl]-benzofuran

The title compound was prepared in a similar manner to that described in Example 40 using 2,4-dimethylbenzaldehyde instead of 2-furaldehyde.
MS(ESI, m/z): 446 [M+NH$_4$]$^+$

Example 55

3-[2-(4-Ethylphenyl)ethyl]-4-(β-D-glucopyranosyloxy)benzofuran

The title compound was prepared in a similar manner to that described in Example 40 using 4-ethylbenzaldehyde instead of 2-furaldehyde.
MS(ESI, m/z): 446 [M+NH$_4$]$^+$

Example 56

4-(β-D-Glucopyranosyloxy)-3-[2-(3,4-dimethylphenyl)ethyl]-benzofuran

The title compound was prepared in a similar manner to that described in Example 40 using 3,4-dimethylbenzaldehyde instead of 2-furaldehyde.
MS(ESI, m/z): 446 [M+NH$_4$]$^+$

Example 57

4-(β-D-Glucopyranosyloxy)-3-[2-(4-isopropylphenyl)ethyl]-benzofuran

The title compound was prepared in a similar manner to that described in Example 40 using 4-isopropylbenzaldehyde instead of 2-furaldehyde.
MS(ESI, m/z): 460 [M+NH$_4$]$^+$

Example 58

3-[2-(2-Chlorophenyl)ethyl]-4-(β-D-glucopyranosyloxy)benzofuran

The title compound was prepared in a similar manner to that described in Example 40 using 2-chlorobenzaldehyde instead of 2-furaldehyde.
MS(ESI, m/z): 452 [M+NH$_4$]$^+$

Example 59

3-[2-(3-Chlorophenyl)ethyl]-4-(β-D-glucopyranosyloxy)benzofuran

The title compound was prepared in a similar manner to that described in Example 40 using 3-chlorobenzaldehyde instead of 2-furaldehyde.
MS(ESI, m/z): 452 [M+NH$_4$]$^+$

Example 60

3-[2-(4-Chlorophenyl)ethyl]-4-(β-D-glucopyranosyloxy)benzofuran

The title compound was prepared in a similar manner to that described in Example 40 using 4-chlorobenzaldehyde instead of 2-furaldehyde.
MS(ESI, m/z): 452 [M+NH$_4$]$^+$

Example 61

3-[2-(4-Ethoxyphenyl)ethyl]-4-(β-D-glucopyranosyloxy)benzofuran

The title compound was prepared in a similar manner to that described in Example 40 using 4-ethoxybenzaldehyde instead of 2-furaldehyde.
MS(ESI, m/z): 462 [M+NH$_4$]$^+$

Example 62

4-(β-D-Glucopyranosyloxy)-3-[2-(4-methylthiophenyl)ethyl]-benzofuran

The title compound was prepared in a similar manner to that described in Example 40 using 4-methylthiobenzaldehyde instead of 2-furaldehyde.
MS(ESI, m/z): 464 [M+NH$_4$]$^+$

Example 63

4-(β-D-Glucopyranosyloxy)-3-[2-(naphtalen-2-yl)ethyl]-benzofuran

The title compound was prepared in a similar manner to that described in Example 40 using 2-naphtoaldehyde instead of 2-furaldehyde.
MS(ESI, m/z): 468 [M+NH$_4$]$^+$

Example 64

3-[2-(4-Butylphenyl)ethyl]-4-(β-D-glucopyranosyloxy)benzofuran

The title compound was prepared in a similar manner to that described in Example 40 using 4-butylbenzaldehyde instead of 2-furaldehyde.
MS(ESI, m/z): 474 [M+NH$_4$]$^+$

Example 65

4-(β-D-Glucopyranosyloxy)-3-[2-(4-isobutylphenyl)ethyl]-benzofuran

The title compound was prepared in a similar manner to that described in Example 40 using 4-isobutylbenzaldehyde instead of 2-furaldehyde.
MS(ESI, m/z): 474 [M+NH$_4$]$^+$

Reference Example 41

4-(3-Benzyloxypropyl)benzaldehyde

To a solution of ethyl diethylphosphonoacetate (1.96 mL) in tetrahydrofuran (40 mL) was added sodium hydride (60%, 0.39 g) under ice-cooling, and the mixture was stirred for 10 minutes. To the reaction mixture was added a solution of terephthalaldehyde mono(diethylacetal) (1.86 g) in tetrahydrofuran (10 mL), and the mixture was stirred at room temperature for 5 hours. The reaction mixture was poured into a saturated aqueous ammonium chloride solution, and the resulting mixture was extracted with diethylether. The extract was washed with water twice and dried over anhydrous magnesium sulfate, and the solvent was removed under reduced pressure. To a solution of the residue in tetrahydrofuran (25 mL) was added 5% platinum-carbon powder (0.22 g), and the mixture was stirred at room temperature under a hydrogen atmosphere overnight. The insoluble material was removed by filtration, and the filtrate was concentrated under reduced pressure. A solution of the residue in diethyl ether (10 mL) was added to a suspension of lithium aluminum hydride (0.44 g) in diethyl ether (30 mL) under ice-cooling, and the mixture was heated for reflux for 1 hour. The reaction mixture was cooled in ice. To the mixture was added water (0.6 mL), 15% aqueous sodium hydroxide solution (0.6 mL) and water (1.8 mL) successively, and the resulting mixture was stirred at room temperature for 10 minutes. The insoluble material was removed by filtration, and the filtrate was concentrated under reduced pressure. To a solution of the residue in N,N-dimethylformamide (30 mL) was added sodium hydride (60%, 0.46 g) under ice-cooling, and the mixture was stirred for 10 minutes. To the mixture was added benzyl bromide (0.99 mL), and the mixture was stirred at room temperature overnight. To the reaction mixture was added ice water, and the resulting mixture was extracted with diethylether. The extract was washed with water and dried over anhydrous magnesium sulfate, and the solvent was removed under reduced pressure. To a solution of the residue in tetrahydrofuran (24 mL) was added 2 mol/L hydrochloric acid (4.1 mL) at room temperature, and the mixture was stirred for 1.5 hours. The reaction mixture was poured into water, and the resulting mixture was extracted with diethyl ether. The extract was washed with water twice and dried over anhydrous magnesium sulfate. The solvent was removed under reduced pressure to give the title compound (2.18 g).

$^1$H-NMR (CDCl$_3$) δ ppm: 1.9-2.0 (2H, m), 2.81 (2H, t, J=7.8 Hz), 3.49 (2H, t, J=6.0 Hz), 4.51 (2H, s), 7.25-7.4 (7H, m), 7.75-7.85 (2H, m), 9.97 (1H, s)

Reference Example 42

2',6'-Dihydroxy-4'-methylacetophenone

To a solution of orcinol (30 g) in pyridine (240 mL) was added acetic anhydride (91 mL) at room temperature, and the mixture was stirred for 16 hours. The reaction mixture was concentrated under reduced pressure, and the residue was dissolved in ethylacetate. The solution was washed with 1 mol/L hydrochloric acid, water, a saturated aqueous sodium hydrogen carbonate solution and brine successively, and dried over anhydrous sodium sulfate. The solvent was removed under reduced pressure to give orcinol diacetate (43.7 g). To a suspension of aluminum chloride (19.3 g) in chlorobenzene (50 mL) was added a solution of orcinol diacetate (10 g) in chlorobenzene (8 mL) in a dropwise manner at 90° C., and the mixture was stirred at the same temperature for 1 hour. The reaction mixture was poured into 0.5 mol/L hydrochloric acid cooled in ice, and the resulting mixture was stirred for 30 minutes. The mixture was extracted with ethyl acetate, and the extract was washed with water and dried over anhydrous sodium sulfate. The solvent was removed under reduced pressure. To the residue was added n-hexane (100 mL), and the mixture was stirred at room temperature for 30 minutes. The insoluble material was collected by filtration and dried under reduced pressure to give the title compound (7.2 g).

$^1$H-NMR (CDCl$_3$) δ ppm: 2.24 (3H, s), 2.7 (3H, s), 6.21 (2H, s), 8.8-9.85 (2H, br)

Reference Example 43

2'-(2,3,4,6-Tetra-O-acetyl-β-D-glucopyranosyloxy)-6'-hydroxy-4'-methylacetophenone The title compound was prepared in a similar manner to that described in Reference Example 24 using 2',6'-dihydroxy-4'-methylacetophenone instead of 2',6'-dihydroxyacetophenone.

$^1$H-NMR (CDCl$_3$) δ ppm: 2.04 (3H, s), 2.05 (3H, s), 2.06 (3H, s), 2.07 (3H, s), 2.31 (3H, s), 2.59 (3H, s), 3.85-3.95 (1H, m), 4.17 (1H, dd, J=12.4 Hz, 2.6 Hz), 4.26 (1H, dd, J=12.4 Hz, 5.5 Hz), 5.15-5.25 (1H, m), 5.25-5.4 (3H, m), 6.28 (1H, d, J=0.9 Hz), 6.52 (1H, d, J=0.9 Hz), 13.1 (1H, s)

Reference Example 44

2'-(2,3,4,6-Tetra-O-acetyl-β-D-glucopyranosyloxy)-6'-methoxycarbonyloxy-4'-methylacetophenone The title compound was prepared in a similar manner to that described in Reference Example 25 using 2'-(2,3,4,6-tetra-O-acetyl-β-D-glucopyranosyloxy)-6'-hydroxy-4'-methylacetophenone instead of 2'-(2,3,4,6-tetra-O-acetyl-β-D-glucopyranosyloxy)-6'-hydroxyacetophenone.

$^1$H-NMR (CDCl$_3$) δ ppm: 2.02 (3H, s), 2.05 (3H, s), 2.106 (3H, s), 2.111 (3H, s), 2.31 (3H, s), 2.46 (3H, s), 3.78 (3H, s), 3.85-3.9 (1H, m), 4.15-4.3 (2H, m), 4.62 (2H, s), 4.99 (1H, d, J=7.6 Hz), 5.05-5.15 (1H, m), 5.2-5.3 (2H, m), 6.35 (1H, s), 6.6 (1H, s)

Example 66

4-(β-D-Glucopyranosyloxy)-6-methyl-3-[2-(4-methylphenyl)ethyl]benzofuran

To a suspension of 2'-(2,3,4,6-tetra-O-acetyl-β-D-glucopyranosyloxy)-6'-methoxycarbonylmethoxy-4'-methylacetophenone (0.35 g) and p-tolualdehyde (81 mg) in ethanol (10 mL) were added water (1.7 mL) and potassium hydroxide (0.41 g), and the mixture was stirred at room temperature for 4 hours. The reaction mixture was poured into 1 mol/L hydrochloric acid (7.5 mL), and the resulting mixture was extracted with ethyl acetate twice. The extracts were combined and washed with brine, and dried over anhydrous magnesium sulfate. The solvent was removed under reduced pressure, and the residue was dissolved in methanol (6 mL)-tetrahydrofuran (1 mL). To the solution was added 10% palladium-carbon powder (0.11 g), and the mixture was stirred at room temperature under a hydrogen atmosphere for 2 hours. The insoluble material was removed by filtration, and the filtrate was concentrated under reduced pressure. To the residue were added sodium acetate (1.15 g), acetic acid (6 mL) and acetic anhydride (1.16 mL), and the mixture was stirred at 115° C. overnight. The reaction mixture was cooled to room temperature and poured into water, and the resulting mixture was extracted with ethyl acetate. The extract was washed with a saturated aqueous sodium hydrogen carbonate solution twice, water and brine successively, and dried over anhydrous magnesium sulfate. The solvent was removed under reduced pressure, and the residue was purified by column chromatography on silica gel (eluent: n-hexane/ethyl acetate=2/1) to give 4-(2,3,4,6-tetra-O-acetyl-β-D-glucopyranosyloxy)-6-methyl-3-[2-(4-methylphenyl)ethyl]benzofuran (0.11 g). This material was dissolved in methanol (5 mL). To the solution was added sodium methoxide (28% methanol solution, 0.036 mL), and the mixture was stirred at room temperature for 1 hour. The reaction mixture was purified by VARIAN BOND ELUT-SCX (eluent: methanol) to give the title compound (74 mg).

$^1$H-NMR (CD$_3$OD) δ ppm: 2.28 (3H, s), 2.42 (3H, s), 2.85-3.2 (4H, m), 3.35-3.6 (4H, m), 3.7 (1H, dd, J=12.1 Hz, 5.9 Hz), 3.91 (1H, dd, J=12.1 Hz, 2.2 Hz), 5.16 (1H, d, J=7.8 Hz), 6.8 (1H, s), 6.9 (1H, s), 7.0-7.15 (4H, m), 7.17 (1H, s)

Examples 67-71

The compounds described in Table 1 were prepared in a similar manner to that described in Example 12 or Example 66 using the corresponding starting materials.

TABLE 1
| Example No. | Structure | $^1$H-NMR (CD$_3$OD) δ ppm: |
|---|---|---|
| Example 67 | 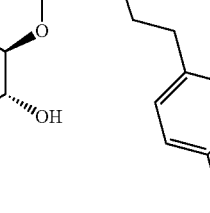 | 1.75-1.85 (2H, m), 2.63 (2H, t, J=7.7 Hz), 2.85-3.1 (3H, m), 3.1-3.25 (1H, m), 3.35-3.65 (6H, m), 3.71 (1H, dd, J=12.0 Hz, 5.5 Hz), 3.9 (1H, dd, J=12.0 Hz, 1.7 Hz), 5.18 (1H, d, J=7.6 Hz), 6.96 (1H, d, J=8.2 Hz), 7.05-7.15 (5H, m), 7.18 (1H, t, J=8.2 Hz), 7.25 (1H, s) |
| Example 68 | 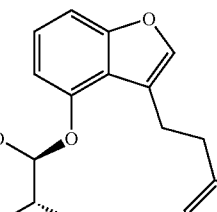 | 2.9-3.25 (4H, m), 3.35-3.55 (3H, m), 3.55-3.65 (1H, m), 3.65-3.75 (4H, m), 3.91 (1H, dd, J=12.0 Hz, 2.1 Hz), 5.19 (1H, d, J=8.1 Hz), 6.7 (1H, dd, J=8.1 Hz, 2.1 Hz), 6.75-6.85 (2H, m), 6.96 (1H, d, J=7.8 Hz), 7.05-7.25 (3H, m), 7.27 (1H, s) |
| Example 69 | 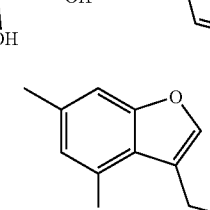 | 2.42 (3H, s), 2.9-3.2 (4H, m), 3.35-3.45 (1H, m), 3.45-3.6 (3H, m), 3.7 (1H, dd, J=12.1 Hz, 6.0 Hz), 3.91 (1H, dd, J=12.1 Hz, 2.0 Hz), 5.17 (1H, d, J=7.4 Hz), 6.81 (1H, s), 6.9 (1H, s), 7.1-7.3 (6H, m) |
| Example 70 | 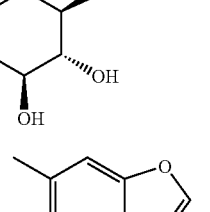 | 2.42 (3H, s), 2.85-3.2 (4H, m), 3.35-3.6 (4H, m), 3.7 (1H, dd, J=12.1 Hz, 5.7 Hz), 3.75 (3H, s), 3.91 (1H, dd, J=12.1 Hz, 2.2 Hz), 5.16 (1H, d, J=7.8 Hz), 6.75-6.85 (3H, m), 6.9 (1H, s), 7.1-7.15 (2H, m), 7.17 (1H, s) |
| Example 71 | 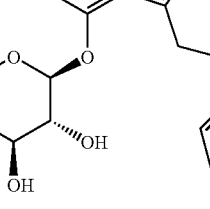 | 2.42 (3H, s), 2.8-3.2 (4H, m), 3.35-3.6 (4H, m), 3.7 (1H, dd, J=12.2 Hz, 5.7 Hz), 3.8-3.95 (3H, m), 3.95-4.05 (2H, m), 5.16 (1H, d, J=7.8 Hz), 6.75-6.95 (4H, m), 7.05-7.15 (2H, m), 7.17 (1H, s) |

Examples 72-81

The compounds described in Tables 2 and 3 were prepared in a similar manner to that described in Example 21 using the corresponding starting materials.

TABLE 2

| Example No. | Structure | $^1$H-NMR (CD$_3$OD) δ ppm: |
|---|---|---|
| Example 72 | 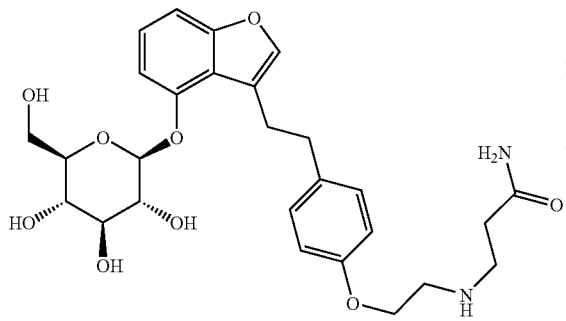 | 2.57 (2H, t, J=6.6 Hz), 2.85-3.25 (8H, m), 3.35-3.65 (4H, m), 3.71 (1H, dd, J=11.9 Hz, 5.7 Hz), 3.9 (1H, dd, J=11.9 Hz, 2.2 Hz), 4.14 (2H, t, J=5.1 Hz), 5.18 (1H, d, J=7.8 Hz), 6.85-6.9 (2H, m), 6.96 (1H, d, J=7.6 Hz), 7.08 (1H, d, J=8.0 Hz), 7.1-7.3 (4H, m) |
| Example 73 | 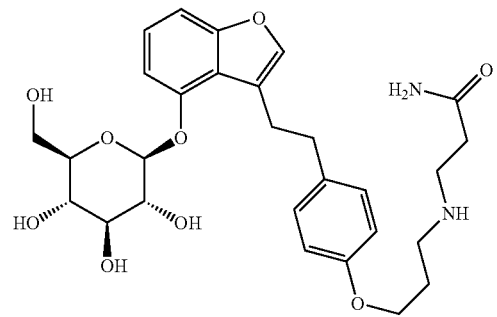 | 1.95-2.1 (2H, m), 2.53 (2H, t, J= 6.6 Hz), 2.85-3.25 (8H, m), 3.35-3.65 (4H, m), 3.71 (1H, dd, J=12.1 Hz, 5.6 Hz), 3.9 (1H, dd, J=12.1 Hz, 2.1 Hz), 3.95-4.1 (2H, m), 5.18 (1H, d, J=7.5 Hz), 6.8-6.9 (2H, m), 6.95 (1H, d, J=7.8 Hz), 7.05-7.3 (5H, m) |
| Example 74 | 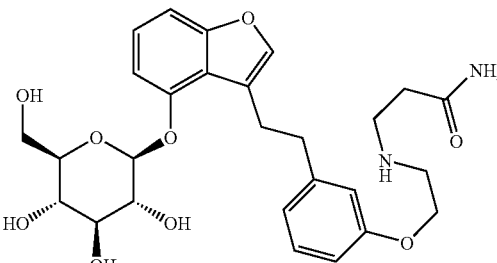 | 2.5 (2H, t, J=6.5 Hz), 2.85-3.25 (8H, m), 3.4-3.7 (4H, m), 3.72 (1H, dd, J=12.1 Hz, 5.5 Hz), 3.9 (1H, dd, J=12.1 Hz, 2.0 Hz), 4.05-4.15 (2H, m), 5.2 (1H, d, J=8.0 Hz), 6.75 (1H, dd, J=8.1 Hz, 2.1 Hz), 6.8-6.95 (2H, m), 6.96 (1H, d, J=7.9 Hz), 7.05-7.25 (3H, m), 7.31 (1H, s) |
| Example 75 | 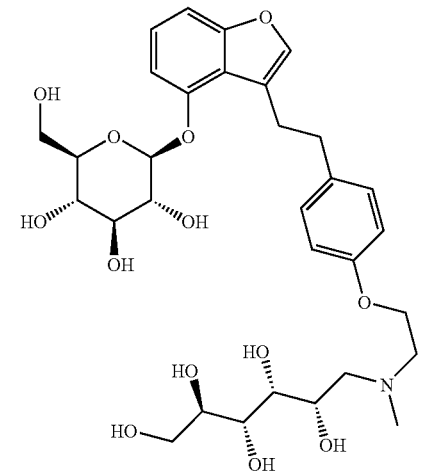 | 2.41 (3H, s), 2.63 (1H, dd, J=13.2 Hz, 7.0 Hz), 2.69 (1H, dd, J=13.2 Hz, 5.3 Hz), 2.85-3.1 (5H, m), 3.1-3.25 (1H, m), 3.35-3.55 (3H, m), 3.55-3.75 (5H, m), 3.75-3.85 (2H, m), 3.85-3.95 (2H, m), 4.07 (2H, t, J=5.7 Hz), 5.18 (1H, d, J=7.6 Hz), 6.8-6.9 (2H, m), 6.95 (1H, d, J=8.1 Hz), 7.08 (1H, d, J=8.1 Hz), 7.1-7.15 (2H, m), 7.18 (1H, t, J=8.1 Hz), 7.26 (1H, s) |

TABLE 2-continued

| Example No. | Structure | ¹H-NMR (CD₃OD) δ ppm: |
|---|---|---|
| Example 76 | 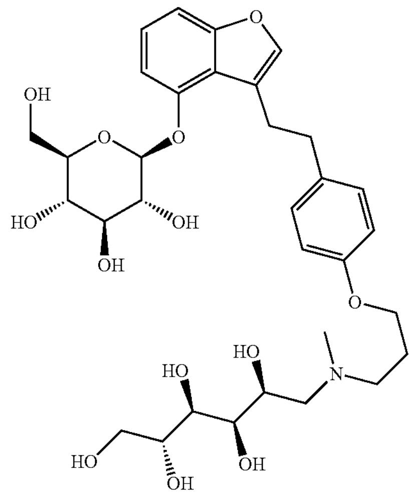 | 1.9-2.0 (2H, m), 2.34 (3H, s), 2.5-2.75 (4H, m), 2.85-3.1 (3H, m), 3.1-3.2 (1H, m), 3.35-3.55 (3H, m), 3.55-3.65 (3H, m), 3.65-3.75 (2H, m), 3.75-3.8 (2H, m), 3.85-3.95 (2H, m), 3.99 (2H, t, J=6.3 Hz), 5.18 (1H, d, J=7.7 Hz), 6.75-6.85 (2H, m), 6.95 (1H, d, J=8.1 Hz), 7.08 (1H, d, J=8.1 Hz), 7.1-7.15 (2H, m), 7.18 (1H, t, J=8.1 Hz), 7.26 (1H, s) |

TABLE 3

| Example No. | Structure | ¹H-NMR (CD₃OD) δ ppm: |
|---|---|---|
| Example 77 | 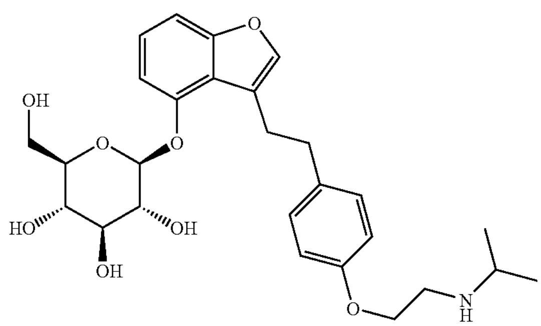 | 1.35 (6H, d, J=6.3 Hz), 2.85-3.1 (3H, m), 3.1-3.25 (1H, m), 3.35-3.65 (7H, m), 3.72 (1H, dd, J=12.2 Hz, 5.6 Hz), 3.91 (1H, dd, J=12.2 Hz, 2.3 Hz), 4.15-4.25 (2H, m), 5.19 (1H, d, J=7.6 Hz), 6.85-6.95 (2H, m), 6.96 (1H, d, J=7.8 Hz), 7.08 (1H, d, J=8.3 Hz), 7.1-7.25 (4H, m) |
| Example 78 | 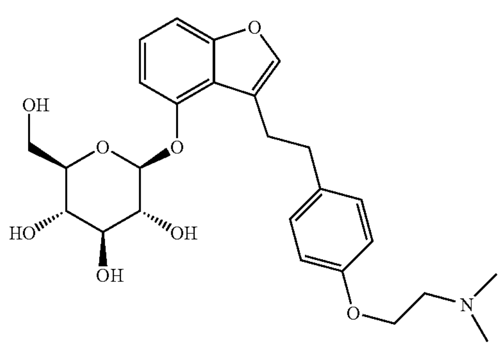 | 2.8-3.1 (9H, m), 3.1-3.25 (1H, m), 3.35-3.6 (6H, m), 3.71 (1H, dd, J=12.0 Hz, 5.5 Hz), 3.91 (1H, dd, J=12.0 Hz, 2.2 Hz), 4.2-4.3 (2H, m), 5.19 (1H, d, J=7.6 Hz), 6.85-6.95 (2H, m), 6.96 (1H, d, J=7.9 Hz), 7.08 (1H, d, J=8.3 Hz), 7.1-7.25 (4H, m) |

TABLE 3-continued

| Example No. | Structure | ¹H-NMR (CD₃OD) δ ppm: |
|---|---|---|
| Example 79 | 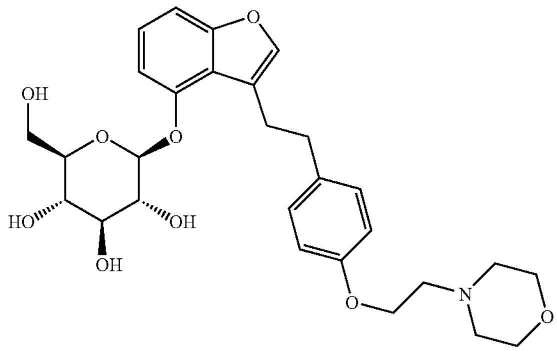 | 2.85-3.6 (14H, m), 3.71 (1H, dd, J=12.1 Hz, 5.7 Hz), 3.75-3.95 (5H, m), 4.2-4.3 (2H, m), 5.18 (1H, d, J=7.6 Hz), 6.85-6.95 (2H, m), 6.96 (1H, d, J=8.1 Hz), 7.08 (1H, d, J=8.3 Hz), 7.1-7.25 (4H, m) |
| Example 80 | 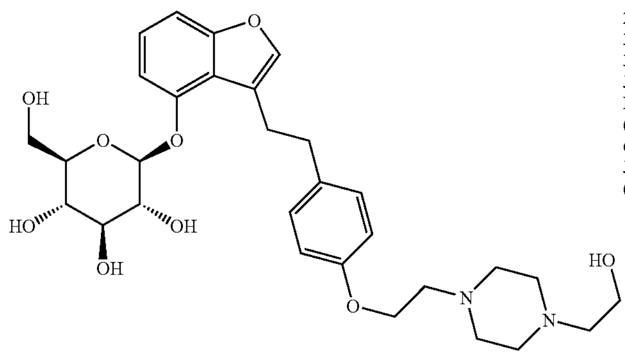 | 2.3-3.1 (15H, m), 3.1-3.25 (1H, m), 3.35-3.55 (3H, m), 3.55-3.65 (1H, m), 3.67 (2H, t, J=6.0 Hz), 3.71 (1H, dd, J=12.1 Hz, 5.7 Hz), 3.9 (1H, dd, J=12.1 Hz, 2.2 Hz), 4.09 (2H, t, J=5.5 Hz), 5.18 (1H, d, J=7.5 Hz), 6.8-6.85 (2H, m), 6.95 (1H, d, J=8.1 Hz), 7.08 (1H, d, J=8.1 Hz), 7.1-7.15 (2H, m), 7.18 (1H, t, J=8.1 Hz), 7.25 (1H, s) |
| Example 81 | 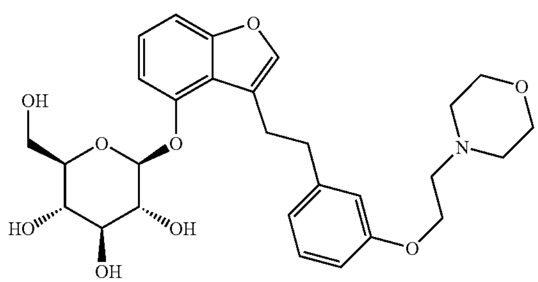 | 2.5-2.65 (4H, m), 2.7-2.8 (2H, m), 2.9-3.25 (4H, m), 3.35-3.75 (9H, m), 3.91 (1H, dd, J=12.1 Hz, 2.2 Hz), 4.0-4.15 (2H, m), 5.19 (1H, d, J=7.6 Hz), 6.72 (1H, dd, J=8.0 Hz, 2.1 Hz), 6.75-6.85 (2H, m), 6.97 (1H, d, J=8.1 Hz), 7.09 (1H, d, J=8.2 Hz), 7.1-7.25 (2H, m), 7.27 (1H, s) |

Reference Example 45

3-[2-(4-Benzyloxycarbonylphenyl)ethyl]-4-hydroxybenzofuran

To a solution of 3-[2-(4-carboxyphenyl)ethyl]-4-hydroxybenzofuran (0.25 g) in tetrahydrofuran (1 mL) were added benzyl alcohol (96 mg), triphenylphosphine (0.26 g) and diethyl azodicarboxylate (40% toluene solution, 0.43 mL), and the mixture was stirred at room temperature for 3 days. The reaction mixture was purified by column chromatography on silica gel (eluent: n-hexane/ethyl acetate=2/1) to give the title compound (0.26 g).

¹H-NMR (CDCl₃) δ ppm: 3.05-3.15 (4H, m), 5.07 (1H, s), 5.36 (2H, s), 6.55 (1H, dd, J=7.7 Hz, 0.8 Hz), 7.0-7.15 (2H, m), 7.19 (1H, s), 7.25-7.3 (2H, m), 7.3-7.5 (5H, m), 7.95-8.05 (2H, m)

Reference Example 46

3-{2-[4-(2-Benzyloxycarbonylethyl)phenyl]ethyl}-4-hydroxybenzofuran

The title compound was prepared in a similar manner to that described in Reference Example 45 using 3-{2-[4-(2-carboxyethyl)phenyl]ethyl}-4-hydroxybenzofuran instead of 3-[2-(4-carboxyphenyl)ethyl]-4-hydroxybenzofuran.

¹H-NMR (CDCl₃) δ ppm: 2.68 (2H, t, J=7.7 Hz), 2.9-3.15 (6H, m), 5.08 (1H, s), 5.12 (2H, s), 6.54 (1H, dd, J=7.5 Hz, 1.1 Hz), 7.0-7.2 (6H, m), 7.22 (1H, s), 7.25-7.4 (5H, m)

Example 82

4-(2,3,4,6-Tetra-O-acetyl-β-D-glucopyranosyloxy)-3-[2-(4-carboxyphenyl)ethyl]benzofuran 3-[2-(4-Benzyloxycarbonylphenyl)ethyl]-4-hydroxybenzofuran (0.26 g) and 2,3,4,6-tetra-O-acetyl-1-O-trichloroacetoimidoyl-α-D-glucopyranose (0.41 g) were dissolved in dichloromethane (5 mL)-ethyl acetate (3 mL). To the solution was added boron trifluoride-diethyl ether complex (0.44 mL), and the mixture was stirred at room temperature for 3 hours. The reaction mixture was poured into a saturated aqueous, sodium hydrogen carbonate solution, and the resulting mixture was extracted with ethyl acetate. The extract was washed with brine and dried over anhydrous sodium sulfate. The solvent was removed under reduced pressure, and the residue was purified by column chromatography on silica gel (eluent: n-hexane/ethyl acetate=3/2-2/3) to give 4-(2,3,4,6-tetra-O-acetyl-β-D-glucopyranosyloxy)-3-[2-(4-benzyloxycarbonylphenyl)ethyl]-benzofuran (0.44 g). This material was dissolved in tetrahydrofuran (5 mL). To the solution was added 10% palladium-carbon powder (0.2 g), and the mixture was stirred at room temperature under a hydrogen atmosphere for 1 hour. The insoluble material was removed by filtration, and the filtrate was concentrated under reduced pressure to give the title compound (0.37 g).

$^1$H-NMR (CD$_3$OD) δ ppm: 1.96 (3H, s), 1.98 (3H, s), 2.0 (3H, s), 2.04 (3H, s), 2.95-3.15 (4H, m), 4.05-4.2 (2H, m), 4.25-4.4 (1H, m), 5.1-5.25 (1H, m), 5.25-5.35 (1H, m), 5.4-5.5 (1H, m), 5.64 (1H, d, J=7.8 Hz), 6.9-7.0 (1H, m), 7.1-7.35 (5H, m), 7.85-7.95 (2H, m)

Example 83

4-(2,3,4,6-Tetra-O-acetyl-β-D-glucopyranosyloxy)-3-{2-[4-(2-carboxyethyl)phenyl]ethyl}benzofuran The title compound was prepared in a similar manner to that described in Example 82 using 3-{2-[4-(2-benzyloxycarbonylethyl)phenyl]ethyl}-4-hydroxybenzofuran instead of 3-[2-(4-benzyloxycarbonylphenyl)ethyl]-4-hydroxybenzofuran.

$^1$H-NMR (CDCl$_3$) δ ppm: 1.96 (3H, s), 2.02 (3H, s), 2.03 (3H, s), 2.06 (3H, s), 2.67 (2H, t, J=7.7 Hz), 2.85-3.1 (6H, m), 3.85-3.95 (1H, m), 4.16 (1H, dd, J=12.3 Hz, 2.3 Hz), 4.28 (1H, dd, J=12.3 Hz, 5.7 Hz), 5.15-5.25 (1H, m), 5.3-5.4 (3H, m), 6.75-6.85 (1H, m), 7.05-7.15 (5H, m), 7.15-7.25 (2H, m)

Example 84

4-(2,3,4,6-Tetra-O-acetyl-β-D-glucopyranosyloxy)-3-{2-[4-(carboxymethylcarbamoyl)phenyl]ethyl}benzofuran To a solution of 4-(2,3,4,6-tetra-O-acetyl-β-D-glucopyranosyloxy)-3-[2-(4-carboxyphenyl)ethyl]benzofuran (0.12 g) in N,N-diemthylformamide (2 mL) were added benzyl 2-aminoacetate hydrochloride (48 mg), 1-hydroxybenzotriazole (32 mg), 1-ethyl-3-(3-dimethylaminopropyl)carbodiimide hydrochloride (77 mg) and triethylamine (0.11 mL), and the mixture was stirred at room temperature for three days. The reaction mixture was poured into 1 mol/L hydrochloric acid, and the resulting mixture was extracted with ethyl acetate. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=1/1-1/2) to give 4-(2,3,4,6-tetra-O-acetyl-β-D-glucopyranosyloxy)-3-{2-[4-(benzyloxycarbonylmethylcarbamoyl)phenyl]ethyl}benzofuran (94 mg). This material was dissolved in methanol (3 mL). To the solution was added 10% palladium-carbon powder (40 mg), and the mixture was stirred at room temperature under a hydrogen atmosphere for 1 hour. The insoluble material was removed by filtration, and the solvent of the filtrate was removed under reduced pressure to give the title compound (82 mg).

$^1$H-NMR (CD$_3$OD) δ ppm: 1.95 (3H, s), 1.98 (3H, s), 2.0 (3H, s), 2.04 (3H, s), 2.95-3.15 (4H, m), 4.07 (2H, s), 4.1-4.2 (2H, m), 4.32 (1H, dd, J=12.8 Hz, 5.6 Hz), 5.1-5.2 (1H, m), 5.25-5.35 (1H, m), 5.4-5.5 (1H, m), 5.63 (1H, d, J=7.9 Hz), 6.93 (1H, d, J=8.2 Hz), 7.1-7.35 (5H, m), 7.7-7.8 (2H, m)

Example 85

4-(2,3,4,6-Tetra-O-acetyl-β-D-glucopyranosyloxy)-3-(2-{4-[2-(carboxymethylcarbamoyl)ethyl]phenyl}ethyl)benzofuran The title compound was prepared in a similar manner to that described in Example 84 using 4-(2,3,4,6-tetra-O-acetyl-β-D-glucopyranosyloxy)-3-{2-[4-(2-carboxyethyl)phenyl]ethyl}benzofuran instead of 4-(2,3,4,6-tetra-O-acetyl-β-D-glucopyranosyloxy)-3-[2-(4-carboxyphenyl)ethyl]-benzofuran.

$^1$H-NMR (CD$_3$OD) δ ppm: 1.95 (3H, s), 1.96 (3H, s), 2.0 (3H, s), 2.04 (3H, s), 2.45-2.55 (2H, m), 2.8-3.05 (6H, m), 3.87 (2H, s), 4.1-4.2 (2H, m), 4.25-4.35 (1H m), 5.1-5.2 (1H, m), 5.25-5.35 (1H, m), 5.35-5.45 (1H, m), 5.62 (1H, d, J=7.9 Hz), 6.93 (1H, d, J=8.3 Hz), 7.05-7.25 (7H, m)

Reference Example 47

Benzyl 2-amino-2-methylpropionate hydrochloride

To a solution of 2-(tert-butoxycarbonylamino)-2-methylpropionic acid (4.06 g) in N,N-dimethylformamide (40 mL) were added potassium carbonate (4.15 g) and benzyl bromide (2.85 mL), and the mixture was stirred at room temperature for 2 hours. The reaction mixture was poured into water, and the resulting mixture was extracted with ethylacetate. The extract was washed with water and brine, and dried over anhydrous sodium sulfate. The solvent was removed under reduced pressure. The residue (solid) was treated with n-hexane and collected by filtration. The crystals were dried under reduced pressure to give benzyl 2-(tert-butoxycarbonylamino)-2-methylpropionate (4.44 g). To the obtained benzyl 2-(tert-butoxycarbonylamino)-2-methylpropionate (4.44 g) was added 4 mol/L hydrochloric acid (1,4-dioxane solution, 15 mL), and the mixture was stirred at room temperature overnight. The reaction mixture was diluted with diethyl ether, and the mixture was stirred for 1 hour. The insoluble material was collected by filtration, washed with diethyl ether and dried under reduced pressure to give the title compound (3.4 g).

$^1$H-NMR (DMSO-d$_6$) δ ppm: 1.49 (6H, s), 5.25 (2H, s), 7.3-7.45 (5H, m), 8.54 (3H, brs)

Example 86

4-(2,3,4,6-Tetra-O-acetyl-β-D-glucopyranosyloxy)-3-[2-(4-(2-[1-carboxy-1-(methyl)ethylcarbamoyl]ethyl)phenyl)ethyl]-benzofuran The title compound was prepared in a similar manner to that described in Example 84 using 4-(2,3,4,6-tetra-O-acetyl-β-D-glucopyranosyloxy)-3-{2-[4-(2-carboxyethyl)phenyl]ethyl}benzofuran and benzyl 2-amino-2-methylpropionate hydrochloride instead of 4-(2,3,4,6-tetra-O-acetyl-β-D-glucopyranosyloxy)-3-[2-(4-carboxyphenyl)ethyl]benzofuran and benzyl 2-aminoacetate hydrochloride, respectively.

$^1$H-NMR (CD$_3$OD) δ ppm: 1.4 (6H, s), 1.95 (3H, s), 1.97 (3H, s), 2.0 (3H, s), 2.04 (3H, s), 2.44 (2H, t, J=7.8 Hz), 2.75-3.1 (6H, m), 4.1-4.2 (2H, m), 4.31 (1H, dd, J=12.6 Hz, 5.4 Hz), 5.1-5.2 (1H, m), 5.25-5.35 (1H, m), 5.4-5.5 (1H, m), 5.62 (1H, d, J=7.9 Hz), 6.92 (1H, d, J=7.8 Hz), 7.05-7.15 (5H, m), 7.15-7.25 (2H, m)

Example 87

4-(2,3,4,6-Tetra-O-acetyl-β-D-glucopyranosyloxy)-3-[(E)-2-(4-bromophenyl)vinyl]benzofuran To a suspension of 2'-(2,3,4,6-tetra-O-acetyl-β-D-glucopyranosyloxy)-6'-(methoxycarbonylmethoxy)acetophenone (0.55 g) and 4-bromobenzaldehyde (0.19 g) in ethanol (9 mL) were added water (3 mL) and potassium hydroxide (0.67 g), and the mixture was stirred at room temperature for three days. To the reaction mixture was added 2 mol/L hydrochloric acid (7 mL), and the resulting mixture was extracted with ethyl acetate twice. The extracts were combined and dried over anhydrous magnesium sulfate. The solvent was removed under reduced pressure. To the residue were added sodium acetate (1.97 g), acetic acid (5 mL) and acetic anhydride (2.08 mL), and the mixture was stirred at 115° C. overnight. The reaction mixture was cooled to room temperature and poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1-3/2) to give the title compound (0.2 g).

$^1$H-NMR (CDCl$_3$) δ ppm: 1.84 (3H, s), 2.05 (3H, s), 2.065 (3H, s), 2.073 (3H, s), 3.9-4.0 (1H, m), 4.18 (1H, dd, J=12.5 Hz, 2.4 Hz), 4.34 (1H, dd, J=12.5 Hz, 5.6 Hz), 5.15-5.4 (3H, m), 5.45-5.55 (1H, m), 6.75-6.85 (1H, m), 6.9 (1H, d, J=16.6 Hz), 7.2-7.35 (3H, m), 7.4-7.45 (2H, m), 7.45-7.55 (2H, m), 7.81 (1H, s)

Example 88

4-(2,3,4,6-Tetra-O-acetyl-β-D-glucopyranosyloxy)-3-[(E)-2-{4-[(E)-3-carboxyprop-1-enyl]phenyl}vinyl]benzofuran A mixture of 4-(2,3,4,6-tetra-O-acetyl-β-D-glucopyranosyloxy)-3-[(E)-2-(4-bromophenyl)vinyl]benzofuran (0.2 g), 3-butenoic acid (0.053 mL), triethylamine (0.22 mL), palladium (II) acetate (7 mg) and tris(2-methylphenyl)phosphine (19 mg) in acetonitrile (4 mL) was heated for reflux under an argon atmosphere for 8 hours. The reaction mixture was cooled to room temperature, and the insoluble material was removed by filtration. The filtrate was diluted with ethyl acetate. The solution was washed with 0.5 mol/L hydrochloric acid, water and brine successively, and dried over anhydrous sodium sulfate. The solvent was removed under reduced pressure, and the residue was purified by column chromatography on silica gel (eluent: n-hexane/ethyl acetate=1/1-dichloromethane/methanol=20/1) to give the title compound (0.17 g).

$^1$H-NMR (CDCl$_3$) δ ppm: 1.83 (3H, s), 2.05 (3H, s), 2.06 (3H, s), 2.07 (3H, s), 3.3-3.35 (2H, m), 3.9-4.0 (1H, m), 4.19 (1H, dd, J=12.3 Hz, 2.4 Hz), 4.33 (1H, dd, J=12.3 Hz, 5.4 Hz), 5.2-5.4 (3H, m), 5.45-5.55 (1H, m), 6.25-6.4 (1H, m), 6.5-6.6 (1H, m), 6.75-6.85 (1H, m), 6.94 (1H, d, J=16.7 Hz), 7.15-7.35 (3H, m), 7.35-7.45 (2H, m), 7.45-7.55 (2H, m), 7.81 (1H, s)

Reference Example 48

1-(2-Amino-2-methylpropionyl)-4-(benzyloxycarbonyl)piperazine hydrochloride

To a solution of 2-(tert-butoxycarbonylamino)-2-methylpropionate (4.06 g) in N,N-dimethylformamide (40 mL) were added 1-(benzyloxycarbonyl)piperazine (6.6 g), 1-hydroxybenzotriazole (3.24 g), 1-ethyl-3-(3-dimethylaminopropyl)carbodiimide hydrochloride (7.67 g) and triethylamine (11.2 mL), and the mixture was stirred at room temperature overnight. The reaction mixture was poured into 1 mol/L hydrochloric acid, and the resulting mixture was extracted with ethyl acetate. The extract was washed with water, 1 mol/L aqueous sodium hydroxide solution, water and brine successively, and dried over anhydrous sodium sulfate. The solvent was removed under reduced pressure. To the residue was added 4 mol/L hydrochloric acid (1,4-dioxane solution, 25 mL), and the mixture was stirred at room temperature for 4 hours. To the reaction mixture was added diethyl ether (50 mL), and the insoluble material was collected by filtration. The collected solid was washed with diethyl ether and dried under reduced pressure to give the title compound (4.65 g).

$^1$H-NMR (DMSO-d$_6$) δ ppm: 1.55 (6H, s), 3.35-3.5 (4H, m), 3.5-3.65 (4H, m), 5.1 (2H, s), 7.3-7.45 (5H, m), 8.24 (3H, brs)

Example 89

4-(β-D-Glucopyranosyloxy)-3-{2-[4-(2-{1-[(piperazin-1-yl)carbonyl]-1-(methyl)ethylcarbamoyl}ethyl)phenyl]ethyl}-benzofuran To a solution of 4-(2,3,4,6-tetra-O-acetyl-β-D-glucopyranosyloxy)-3-{2-[4-(2-carboxyethyl)phenyl]ethyl}benzofuran (0.13 g) in N,N-dimethylformamide (2 mL) were added 1-(2-amino-2-methylpropionyl)-4-(benzyloxycarbonyl)piperazine hydrochloride (82 mg), 1-hydroxybenzotriazole (32 mg), 1-ethyl-3-(3-dimethylaminopropyl)carbodiimide hydrochloride (77 mg) and triethylamine (0.11 mL), and the mixture was stirred at room temperature overnight. The reaction mixture was poured into 1 mol/L hydrochloric acid, and the resulting mixture was extracted with ethylacetate. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: dichloromethane/methanol=30/1-15/1) to give 4-(2,3,4,6-tetra-O-acetyl-β-D-glucopyranosyloxy)-[2-(4-{2-[1-{[4-(benzyloxycarbonyl)piperazin-1-yl]-carbonyl}-1-(methyl)ethylcarbamoyl]ethyl}phenyl)ethyl]-benzofuran (0.1 g). This material was dissolved in methanol (3 mL). To the solution was added 10% palladium-carbon powder (40 mg), and the mixture was stirred at room temperature under a hydrogen atmosphere for 1 hour. The insoluble material was removed by filtration. The solution of the filtrate was removed under reduced pressure to give 4-(2,3,4,6-tetra-O-acetyl-β-D-glucopyranosyloxy)-{2-[4-(2-{1-[(piperazin-1-yl)carbonyl]-1-(methyl)ethylcarbamoyl}ethyl)phenyl]ethyl}-benzofuran (85 mg). This material was dissolved in methanol (3 mL). To the solution was added sodium methoxide (28% methanol solution, 0.03 mL), and the mixture was stirred at room temperature for 1 hour. To the reaction mixture was added acetic acid (0.015 mL), and the resulting mixture was concentrated under reduced pressure. The residue was purified by solid phase extraction on ODS (washing solvent: distilled water, eluent: methanol) to give the title compound (41 mg).

$^1$H-NMR (CD$_3$OD) δ ppm: 1.36 (6H, s), 2.49 (2H, t, J=7.5 Hz), 2.7-3.25 (10H, m), 3.35-3.7 (8H, m), 3.72 (1H, dd, J=12.1 Hz, 5.5 Hz), 3.91 (1H, dd, J=12.1 Hz, 1.9 Hz), 5.18 (1H, d, J=7.6 Hz), 6.96 (1H, d, J=8.2 Hz), 7.05-7.25 (6H, m), 7.27 (1H, s)

Example 90

4-(β-D-Glucopyranosyloxy)-3-[2-(4-{2-[1-{[4-(2-hydroxyethyl)piperazin-1-yl]carbonyl}-1-(methyl)ethylcarbamoyl]-ethyl}phenyl)ethyl]benzofuran To a solution of 4-(2,3,4,6-tetra-O-acetyl-β-D-glucopyranosyloxy)-3-[2-(4-{2-[1-carboxy-1-(methyl)ethylcarbamoyl]ethyl}phenyl)ethyl]benzofuran (0.14 g) in N,N-dimethylformamide (2 mL) were added 1-(2-hydroxyethyl)piperazine (30 mg), 1-hydroxybenzotriazole (31 mg), 1-ethyl-3-(3-dimethylaminopropyl)carbodiimide hydrochloride (74 mg) and triethylamine (0.11 mL), and the mixture was stirred at room temperature for three days. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol =10/1-5/1) to give 4-(2,3,4,6-tetra-O-acetyl-β-D-glucopyranosyloxy) -[2-(4-{2-[1-{[4-(2-hydroxyethyl)piperazin-1-yl]carbonyl}-1'-(methyl)ethylcarbamoyl]ethyl}phenyl)ethyl]-benzofuran (0.11 g). This material was dissolved in methanol (4 mL). To the solution was added sodium methoxide (28% methanol solution, 0.03 mL), and the mixture was stirred at room temperature for 1 hour. To the reaction mixture was added acetic acid (0.015 mL), and the resulting mixture was concentrated under reduced pressure. The residue was purified by solid phase extraction on ODS (washing solvent: distilled water, eluent: methanol) to give the title compound (60 mg).

$^1$H-NMR (CD$_3$OD) δ ppm: 1.36 (6H, s), 2.3-2.55 (8H, m), 2.85 (2H, t, J=7.7 Hz), 2.9-3.25 (4H, m), 3.35-3.7 (10H, m), 3.71 (1H, dd, J=12.2 Hz, 5.5 Hz), 3.91 (1H, dd, J=12.2 Hz, 2.2 Hz), 5.18 (1H, d, J=7.8 Hz), 6.96 (1H, d, J=7.7 Hz), 7.0-7.3 (7H, m)

Examples 91-99

The compounds described in Tabled 4 and 5 were prepared in a similar manner to that described in Example 89 or Example 90 using the corresponding starting materials.

TABLE 4

| Example No. | Structure | $^1$H-NMR (CD$_3$OD) δ ppm: |
|---|---|---|
| Example 91 | 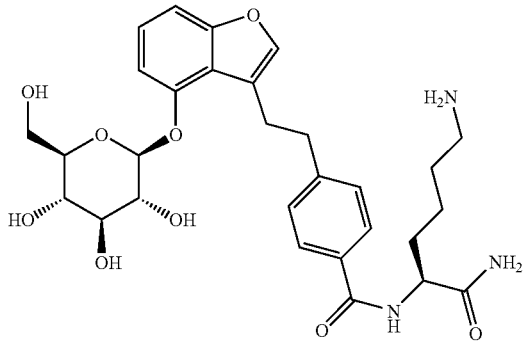 | 1.35-2.1 (6H, m), 2.8-2.95 (2H, m), 3.0-3.65 (8H, m), 3.72 (1H, dd, J=11.8 Hz, 5.6 Hz), 3.85-3.95 (1H, m), 4.5-4.65 (1H, m), 5.19 (1H, d, J=7.4 Hz), 6.97 (1H, d, J=8.4 Hz), 7.08 (1H, d, J=8.1 Hz), 7.15-7.3 (2H, m), 7.33 (2H, d, J=8.2 Hz), 7.77 (2H, d, J=8.2 Hz) |
| Example 92 | 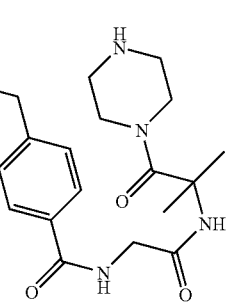 | 1.47 (6H, s), 2.75-2.9 (4H, m), 3.0-3.3 (4H, m), 3.35-3.8 (9H, m), 3.91 (1H, dd, J=12.0 Hz, 2.3 Hz), 3.99 (2H, s), 5.19 (1H, d, J=7.7 Hz), 6.97 (1H, d, J=8.1 Hz), 7.08 (1H, d, J=8.1 Hz), 7.19 (1H, t, J=8.1 Hz), 7.26 (1H, s), 7.33 (2H, d, J=8.2 Hz), 7.77 (2H, d, J=8.2 Hz) |

TABLE 4-continued

| Example No. | Structure | $^1$H-NMR (CD$_3$OD) δ ppm: |
|---|---|---|
| Example 93 | 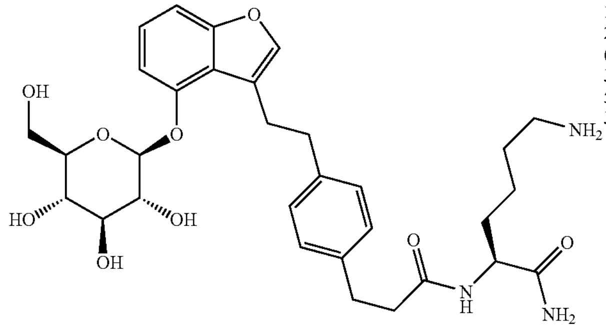 | 1.1-1.85 (6H, m), 2.56 (2H, t, J=7.3 Hz), 2.7-3.25 (8H, m), 3.35-3.6 (4H, m), 3.73 (1H, dd, J=12.0 Hz, 5.6 Hz), 3.9 (1H, dd, J=12.0 Hz, 2.1 Hz), 4.2-4.35 (1H, m), 5.19 (1H, d, J=7.5 Hz), 6.96 (1H, d, J=8.3 Hz), 7.05-7.25 (6H, m), 7.28 (1H, s) |
| Example 94 | 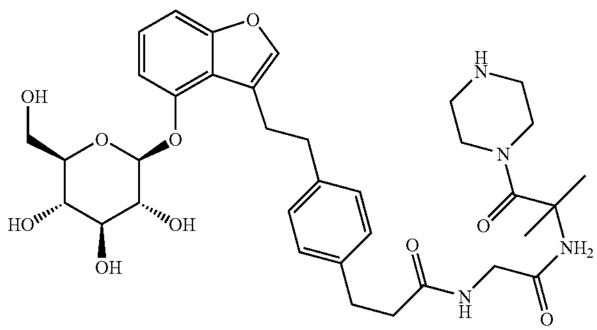 | 1.43 (6H, s), 2.55 (2H, t, J=7.6 Hz), 2.75-3.25 (10H, m), 3.35-3.8 (11H, m), 3.9 (1H, dd, J=11.9 Hz, 1.8 Hz), 5.18 (1H, d, J=7.4 Hz), 6.96 (1H, d, J=8.2 Hz), 7.05-7.25 (6H, m), 7.27 (1H, s) |
| Example 95 | 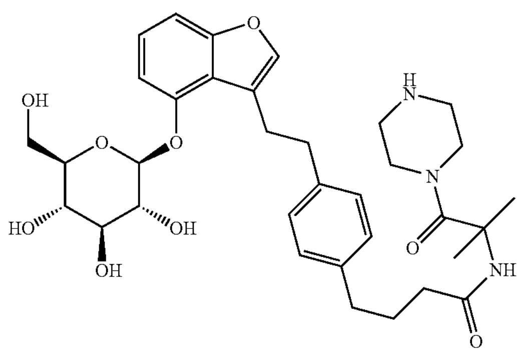 | 1.43 (6H, s), 1.8-1.95 (2H, m), 2.1-2.25 (2H, m), 2.5-2.85 (6H, m), 2.85-3.25 (4H, m), 3.3-3.75 (9H, m), 3.85-3.95 (1H, m), 5.19 (1H, d, J=7.9 Hz), 6.96 (1H, d, J=8.1 Hz), 7.0-7.25 (6H, m), 7.28 (1H, s) |
| Example 96 | 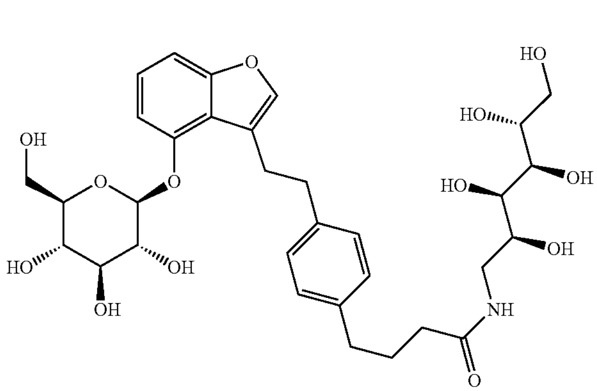 | 1.85-2.0 (2H, m), 2.22 (2H, t, J=7.6 Hz), 2.6 (2H, t, J=7.5 Hz), 2.85-3.0 (1H, m), 3.0-3.1 (2H, m), 3.1-3.3 (2H, m), 3.35-3.85 (12H, m), 3.9 (1H, dd, J=12.3 Hz, 2.0 Hz), 5.19 (1H, d, J=7.3 Hz), 6.96 (1H, d, J=7.8 Hz), 7.05-7.25 (6H, m), 7.28 (1H, s) |

TABLE 5

| Example No. | Structure | $^1$H-NMR (CD$_3$OD) δ ppm: |
|---|---|---|
| Example 97 | 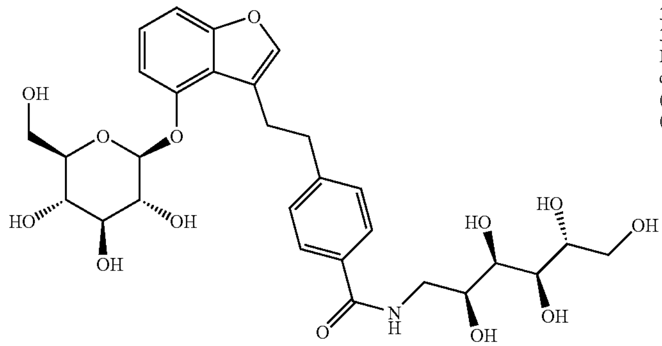 | 3.0-3.35 (4H, m), 3.35-3.85 (12H, m), 3.85-4.0 (2H, m), 5.19 (1H, d, J=7.7 Hz), 6.97 (1H, d, J=7.7 Hz), 7.08 (1H, d, J=8.2 Hz), 7.15-7.25 (1H, m), 7.26 (1H, s), 7.32 (2H, d, J=8.2 Hz), 7.73 (2H, d, J=8.2 Hz) |
| Example 98 | 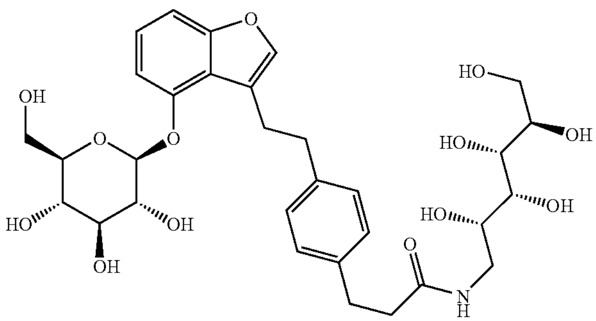 | 2.49 (2H, t, J=7.6 Hz), 2.87 (2H, t, J=7.6 Hz), 2.9-3.25 (5H, m), 3.4-3.85 (12H, m), 3.9 (1H, dd, J=12.3 Hz, 1.9 Hz), 5.18 (1H, d, J=7.6 Hz), 6.95 (1H, d, J=7.6 Hz), 7.05-7.25 (6H, m), 7.27 (1H, s) |
| Example 99 | 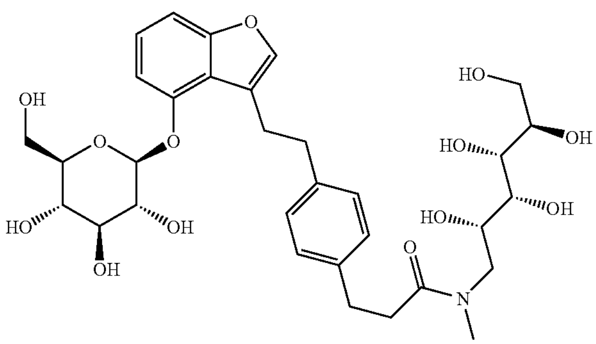 | 2.55-3.25 (11H, m), 3.3-3.75 (11H, m), 3.77 (1H, dd, J=11.0 Hz, 3.5 Hz), 3.85-4.0 (2H, m), 5.18 (1H, d, J-7.6 Hz), 6.96 (1H, d, J=8.0 Hz), 7.05-7.3 (7H, m) |

Reference Example 49

3-Ethynyl-4-methoxybenzo[b]thiophene

To a solution of 2,3-dihydro-4-methoxybenzo[b]-thiophen-3-one (Ref. Chandrani, Mukherjee.; Sukanta, Kamila.; Asish, De. Tetrahedron 2003, 59, 4767-4774) (0.25 g) and triethylamine (0.73 mL) in dichloromethane (5 mL) was added trifluoromethanesulfonic acid anhydride (0.28 mL) under ice-cooling, and the mixture was stirred at the same temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate =9/1) to give 3-trifluoromethanesulfonyloxy-4-methoxybenzo[b]thiophene (0.37 g). This material was dissolved in triethylamine (4 mL). To the solution were added (trimethylsilyl)acetylene (0.34 mL), tetrakis(triphenylphosphine)palladium (0) (0.14 g) and copper (I) iodide (45 mg), and the mixture was heated for reflux under an argon atmosphere for 12 hours. The reaction mixture was cooled to room temperature and diluted with diethyl ether, and the insoluble material was removed by filtration. The filtrate was washed with 1 mol/L hydrochloric acid, water and brine successively, and dried over anhydrous sodium sulfate. The solvent was removed under reduced pressure, and the residue was purified by column chromatography on silica gel (eluent: n-hexane/ethyl acetate=20/1) to give 4-methoxy-3-(2-trimethylsilylethynyl)benzo[b]thiophene (0.3 g). This material was dissolved in tetrahydrofuran (5 mL). To the solution was added tetra(n-butyl)ammonium fluoride (0.34 g), and the mixture was stirred at room temperature for 1 hour. The reaction mixture was poured into 0.5 mol/L hydrochloric acid, and the resulting mixture was extracted with diethyl ether. The extract was washed with water and brine, and dried over anhydrous sodium sulfate. The solvent was removed under reduced pressure, and the residue was purified by column chromatography on silica gel (eluent: n-hexane/ethyl acetate=15/1) to give the title compound (0.2 g).

¹H-NMR (CDCl₃) δ ppm: 3.21 (1H, s), 3.97 (3H, s), 6.75-6.85 (1H, m), 7.25-7.35 (1H, m), 7.4-7.45 (1H, m), 7.6 (1H, s)

Reference Example 50

3-[2-(4-Benzyloxycarbonylphenyl)ethynyl]-4-methoxybenzo-[b]thiophene

3-Ethynyl-4-methoxybenzo[b]thiophene (0.2 g) was dissolved in triethylamine (4mL). To the solution were added 4-iodobenzoic acid (0.29 g), tetrakis(triphenylphosphine)palladium (0) (0.12 g) and copper (I) iodide (41 mg), and the mixture was heated for ref lux under an argon atmosphere overnight. The reaction mixture was poured into ethyl acetate-1 mol/L hydrochloric acid, and the insoluble material was removed by filtration. The organic layer was separated from the filtrate, washed with water and brine. The organic layer was dried over anhydrous sodium sulfate, and the solvent was removed under reduced pressure, and the residue was purified by column chromatography on silica gel (eluent: n-hexane/ethyl acetate=1/1-1/2) to give 3-[2-(4-carboxyphenyl)ethynyl]-4-methoxybenzo[b]thiophene (0.32 g). This material was dissolved in N,N-dimethylformamide (10 mL). To the solution were added potassium carbonate (0.29 g) and benzyl bromide (0.16 mL), and the mixture was stirred at room temperature for three hours. The reaction mixture was poured into water, and the resulting mixture was extracted with diethylether. The extract was washed with water and brine, and dried over anhydrous sodium sulfate. The solvent was removed under reduced pressure, and the residue was purified by column chromatography on silica gel (eluent: n-hexane/ethyl acetate=10/1) to give the title compound (0.2 g).

¹H-NMR (CDCl₃) δ ppm: 4.02 (3H, s), 5.38 (2H, s), 6.8-6.85 (1H, m), 7.3-7.5 (7H, m), 7.55-7.65 (3H, m), 8.05-8.1 (2H, m)

Reference Example 51

3-[2-(4-Benzyloxycarbonylphenyl)ethyl]-4-hydroxybenzo[b]-thiophene

3-[2-(4-Benzyloxycarbonylphenyl)ethynyl]-4-methoxybenzo[b]thiophene (0.2 g) was dissolved in tetrahydrofuran (3 mL)-ethanol (3 mL). To the solution was added 10% palladium-carbon powder (40 mg), and the mixture was stirred at room temperature under a hydrogen atmosphere for 14 hours. The insoluble material was removed by filtration, and the filtrate was concentrated under reduced pressure. The residue was purified by column chromatography on silica gel (eluent: n-hexane/ethyl acetate=10/1) to give 3-[2-(4-benzyloxycarbonylphenyl)ethyl]-4-methoxybenzo[b]thiophene (0.15 g). This material was dissolved in dichloromethane (4 mL). To the solution was added boron tribromide (0.038 mL) at −78° C., and the mixture was stirred at ambient temperature for 2 hours. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1-1/1) to give 3-[2-(4-carboxyphenyl)ethyl]-4-methoxybenzo[b]thiophene (85 mg). This material was dissolved in dichloromethane (4 mL). To the solution was added boron tribromide (0.057 mL) at −78° C., and the mixture was stirred at the same temperature for 1 hour. Then the mixture was stirred for 1 hour under ice-cooling. The reaction mixture was poured into water, and the resulting mixture was extracted with ethyl acetate. The extract was washed with water and brine, and dried over anhydrous sodium sulfate. The solvent was removed under reduced pressure to give 3-[2-(4-carboxyphenyl)ethyl]-4-hydroxybenzo[b]thiophene (80 mg). This material was dissolved in tetrahydrofuran (1 mL). To the solution were added benzyl alcohol (29 mg), triphenylphosphine (79 mg) and diethyl azodicarboxylate (40% toluene solution, 0.13 mL), and the mixture was stirred at room temperature for 1 hour. The reaction mixture was purified by column chromatography on silica gel (eluent: n-hexane/ethyl acetate=5/1-3/1) to give the title compound (35 mg).

¹H-NMR (CDCl₃) δ ppm: 3.05-3.15 (2H, m), 3.3-3.4 (2H, m), 5.14 (1H, s), 5.36 (2H, s), 6.65 (1H, d, J=7.4 Hz), 6.85 (1H, s), 7.1-7.2 (1H, m), 7.25-7.5 (8H, m), 7.95-8.05 (2H, m)

Example 100

4-(2,3,4,6-Tetra-O-acetyl-β-D-glucopyranosyloxy)-3-[2-(4-carboxyphenyl)ethyl]benzo[b]thiophene To a solution of 3-[2-(4-benzyloxycarbonylphenyl)ethyl]-4-hydroxybenzo[b]thiophene (35 mg) and 2,3,4,6-tetra-O-acetyl-1-O-trichloroacetoimidoyl-α-D-glucopyranose (53 mg) in dichloromethane (3 mL) was added boron trifluoride-diethyl ether complex (0.006 mL), and the mixture was stirred at room temperature overnight. The reaction mixture was poured into a saturated aqueous sodium hydrogen carbonate solution, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=2/1-3/2) to give 4-(2,3,4,6-tetra-O-acetyl-β-D-glucopyranosyloxy)-3-[2-(4-benzyloxycarbonylphenyl)ethyl]benzo[b]thiophene (38 mg). This material was dissolved in dichloromethane (1 mL). To the solution were added dimethyl sulfide (0.15 mL) and boron trifluoride-diethyl ether complex (0.067 mL), and the mixture was stirred at 35° C. for 4 hours. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=20/1) to give the title compound (25 mg).

¹H-NMR (CDCl₃) δ ppm: 1.99 (3H, s), 2.01 (3H, s), 2.04 (3H, s), 2.06 (3H, s), 3.0-3.25 (3H, m), 3.35-3.45 (1H, m), 3.85-3.95 (1H, m), 4.16 (1H, dd, J=12.4 Hz, 2.3 Hz), 4.3 (1H, dd, J=12.4 Hz, 5.5 Hz), 5.15-5.25 (1H, m), 5.3-5.4 (2H, m), 5.4-5.45 (1H, m), 6.72 (1H, s), 6.85-6.95 (1H, m), 7.15-7.3 (3H, m), 7.5-7.6 (1H, m), 7.95-8.05 (2H, m)

Example 101

3-{2-[4-(Carbamoylmethylcarbamoyl)phenyl]ethyl}-4-(β-D-glucopyranosyloxy)benzo[b]thiophene The title compound was prepared in a similar manner to that described in Example 90 using 4-(2,3,4,6-tetra-O-acetyl-β-D-glucopyranosyloxy)-3-[2-(4-carboxyphenyl)ethyl]-benzo[b]thiophene and glycinamide hydrochloride instead of 4-(2,3,4,6-tetra-O-acetyl-β-D-glucopyranosyloxy)-3-[2-(4-{2-[1-carboxy-1-(methyl)ethylcarbamoyl]ethyl}phenyl)ethyl]-benzofuran and 1-(2-hydroxyethyl)piperazine, respectively.

¹H-NMR (CD₃OD) δ ppm: 3.0-3.7 (8H, m), 3.72 (1H, dd, J=11.9 Hz, 5.8 Hz), 3.91 (1H, dd, J=11.9 Hz, 2.2 Hz), 4.02

(2H, s), 5.22 (1H, d, J=7.4 Hz), 6.91 (1H, s), 7.11 (1H, d, J=7.9 Hz), 7.2-7.35 (3H, m), 7.48 (1H, d, J=7.7 Hz), 7.75-7.85 (2H, m)

Reference Example 52

4-Hydroxy-3-[2-(4-methylphenyl)ethyl]benzo[b]thiophene

3-Ethynyl-4-methoxybenzo[b]thiophene (0.15 g) was dissolved in triethylamine (10 mL). To the solution were added 4-bromotoluene (0.11 mL), tetrakis(triphenylphosphine)palladium (0) (92 mg) and copper (I) iodide (30 mg), and the mixture was heated for reflux under an argon atmosphere for 10 hours. The reaction mixture was diluted with diethyl ether, and the insoluble material was removed by filtration. The filtrate was concentrated under reduced pressure, and the residue was purified by column chromatography on silica gel (eluent: n-hexane-n-hexane/ethyl acetate=50/1) to give 4-methoxy-3-[2-(4-methylphenyl)ethynyl]benzo[b]thiophene (27 mg). This material was dissolved in ethanol (1.5 mL). To the solution was added 10% palladium-carbon powder (10 mg), and the mixture was stirred at room temperature under a hydrogen atmosphere overnight. The insoluble material was removed by filtration, and the filtrate was concentrated under reduced pressure to give 4-methoxy-3-[2-(4-methylphenyl)ethyl]-benzo[b]thiophene (27 mg). This material was dissolved in dichloromethane (1.5 mL). To the solution was added boron tribromide (0.011 mL) at $-78°$ C., and the mixture was stirred at the same temperature for 1 hour. Then the mixture was stirred under ice-cooling for 1 hour. The reaction mixture poured into water, and the resulting mixture was extracted with ethyl acetate. The extract was washed with a saturated aqueous sodium hydrogen carbonate solution and brine, and dried over anhydrous magnesium sulfate. The solvent was removed under reduced pressure, and the residue was purified by column chromatography on silica gel (eluent: n-hexane/ethyl acetate=15/1) to give the title compound (10 mg).

$^1$H-NMR (CDCl$_3$) δ ppm: 2.33 (3H, s), 2.95-3.05 (2H, m), 3.25-3.4 (2H, m), 5.2 (1H, s), 6.64 (1H, d, J=7.6 Hz), 6.89 (1H, s), 7.05-7.2 (5H, m), 7.41 (1H, d, J=7.6 Hz)

Example 102

4-(β-D-Glucopyranosyloxy)-3-[2-(4-methylphenyl)ethyl]-benzo[b]thiophene

The title compound was prepared in a similar manner to that described in Example 1 using 4-hydroxy-3-[2-(4-methylphenyl)ethyl]benzo[b]thiophene instead of 4-hydroxy-3-[2-(4-methylphenyl)ethyl]benzofuran.

$^1$H-NMR (CD$_3$OD) δ ppm: 2.28 (3H, s), 2.85-3.0 (1H, m), 3.0-3.1 (1H, m), 3.2-3.35 (1H, m), 3.35-3.45 (1H, m), 3.45-3.65 (4H, m), 3.71 (1H, dd, J=12.1 Hz, 5.8 Hz), 3.91 (1H, dd, J=12.1 Hz, 2.4 Hz), 5.21 (1H, d, J=8.1 Hz), 6.9 (1H, s), 7.0-7.15 (5H, m), 7.25 (1H, t, J=8.1 Hz), 7.47 (1H, dd, J=8.1 Hz, 0.8 Hz)

Test Example 1

Assay for Inhibitory Effects on Human SGLT1 Activity

1) Cloning and Construction of the Vector Expressing Human SGLT1

The cDNA library was prepared for PCR amplification by reverse transcription from total RNA deprived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT1

The expression vector of human SGLT1 was digested by Sca I into a linear DNA. The linear DNA was transfected into CHO-KL cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-αD-glucopyranoside was measured by the method described below. The cell line, which showed the greatest uptake activity, was selected and designated as CS1-5-11D. CS1-5-11D cells were cultured in the presence of G418 at 200 μg/mL.

3) Measurement of the Inhibitory Activity Against the Uptake of Methyl-α-D-glucopyranoside (α-MG)

CS1-5-11D cells were seeded into a 96-well culture plate at a density of $3 \times 10^4$ cells/well and cultured for 2 days, and were used in the uptake assay. A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of CS1-5-11D cells, 180 μL of the pre-treatment buffer (the basal uptake buffer without α-MG) was added to each well and incubated at 37° C. for 10 minutes. After repeating the same treatment, the pre-treatment-buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter Top-Count (Packard). One hundred was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited (IC$_{50}$ value), was calculated using logit plot. The results are shown in Table 6.

TABLE 6

| Test compound | IC$_{50}$ value (nM) |
|---|---|
| Example 7 | 15 |
| Example 24 | 25 |

Test Example 2

Assay for Inhibitory Effects on Human SGLT2 Activity

1) Cloning and Construction of the Vector Expressing Human SGLT2

The cDNA library was prepared for PCR amplification by reverse transcription from total RNA deprived from human kidney (Ori gene) using oligo-dT as a primer. Using this cDNA library as a template, the DNA fragment coding 2 to 2039 bp of human SGLT2 (ACCESSION: M95549, M95299), which was reported by R. G. Wells et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT2

The expression vector of human SGLT2 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS2-5E. CS2-5E cells were cultured in the presence of G418 at 200 µg/mL.

3) Measurement of the Inhibitory Activity Against the Uptake of Methyl-α-D-glucopyranoside (α-MG)

CS2-5E cells were seeded into a 96-well culture plate at a density of $3\times10^4$ cells/well and cultured for 2 days, and were used in the uptake assay. A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of CS1-5-11D cells, 180 µL of the pre-treatment buffer (the basal uptake buffer without α-MG) was added to each well and incubated at 37° C. for 10 minutes. After repeating the same treatment, the pre-treatment buffer was removed. To each well was added 75 µL of the measurement buffer or the basal uptake buffer was added and incubated at 37° C. for 1 hour. After removing the measurement buffer, cells were washed twice with 180 µL per well of the washing buffer (the basal uptake buffer containing 10 mM non-labeled α-MG). The cells were solubilized by 75 µL per well of 0.2 mol/L sodium hydroxide. The cell lysates were transferred into PicoPlates (Packard), and then added 150 µL of MicroScint-40 (Packard) and mixed. Radioactivity was measured by means of micro-scintillation counter Top-Count (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited ($IC_{50}$ value), was calculated using logit plot. The results are shown in Table 7.

TABLE 7

| Test compound | $IC_{50}$ value (nM) |
|---|---|
| Example 2 | 6 |
| Example 3 | 41 |
| Example 43 | 12 |

INDUSTRIAL APPLICABILITY

The fused heterocyclic derivatives represented by the above general formula (I) of the present invention, pharmaceutically acceptable salts thereof and prodrugs thereof exert an inhibitory activity in human SGLT and can suppress increase of blood glucose level or lower blood glucose level by inhibiting absorption of carbohydrate such as glucose at the small intestine or by inhibiting reabsorption of glucose at the kidney. Therefore, the present invention can provide excellent agents for the prevention or treatment of a disease associated with hyperglycemia such as diabetes, postprandial hyperglycemia, impaired glucose tolerance, diabetic complications, obesity or the like.

The invention claimed is:

1. A fused heterocyclic derivative represented by the following general formula (I):

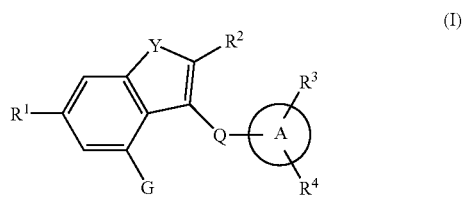

wherein $R^1$ represents a hydrogen atom, a halogen atom, a hydroxy group, an amino group, a mono or di($C_{1-6}$ alkyl)amino group, a $C_{1-6}$ alkyl group, a $C_{1-6}$ alkoxy group, a halo ($C_{1-6}$ alkyl) group, a halo($C_{1-6}$ alkoxy) group, a hydroxy ($C_{1-6}$ alkyl) group, a hydroxy($C_{1-6}$ alkoxy) group, a mono or di[hydroxy($C_{1-6}$ alkyl)]amino group, a carboxy group, a $C_{2-7}$ alkoxycarbonyl group, a carbamoyl group or a carbamoyl($C_{1-6}$ alkyl) group;

$R^2$ represents a hydrogen atom, a halogen atom or a $C_{1-6}$ alkyl group;

$R^3$ and $R^4$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo ($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group, a hydroxy($C_{1-6}$ alkylthio) group, a carboxy group, a carboxy($C_{1-6}$ alkyl) group, a carboxy($C_{2-6}$ alkenyl) group, a carboxy($C_{1-6}$ alkoxy) group, a carboxy($C_{1-6}$ alkylthio) group, a $C_{2-7}$ alkoxycarbonyl group, a $C_{2-7}$ alkoxycarbonyl-substituted ($C_{1-6}$ alkyl) group, a $C_{2-7}$ alkoxycarbonyl-substituted ($C_{2-6}$ alkenyl) group, a $C_{2-7}$ alkoxycarbonyl-substituted ($C_{1-6}$ alkoxy) group, a $C_{2-7}$ alkoxycarbonyl-substituted ($C_{1-6}$ alkylthio) group, a $C_{1-6}$ alkylsulfinyl group, a $C_{1-6}$ alkylsulfonyl group, —U—V—W—N($R^5$)-Z or any of the following substitutes (i) to (xxviii) which may have 1 to 3 substituents selected from the following substituent group α on the ring;

(i) a $C_{6-10}$ aryl group, (ii) $C_{6-10}$ aryl-O—, (iii) $C_{6-10}$ aryl-S—, (iv) a $C_{6-10}$ aryl-substituted ($C_{1-6}$ alkyl) group, (v) a $C_{6-10}$ aryl-substituted ($C_{1-6}$ alkoxy) group, (vi) a $C_{6-10}$ aryl-substituted ($C_{1-6}$ alkylthio) group, (vii) a heteroaryl group, (viii) heteroaryl-O—, (ix) heteroaryl-S—, (x) a heteroaryl($C_{1-6}$ alkyl) group, (xi) a heteroaryl($C_{1-6}$ alkoxy) group, (xii) a heteroaryl($C_{1-6}$ alkylthio) group, (xiii) a $C_{3-8}$ cycloalkyl group, (xiv) $C_{3-8}$ cycloalkyl-O—, (xv) $C_{3-8}$ cycloalkyl-S—, (xvi) a $C_{3-8}$ cycloalkyl-substituted ($C_{1-6}$ alkyl) group, (xvii) a $C_{3-8}$ cycloalkyl-substituted ($C_{1-6}$ alkoxy) group, (xviii) a $C_{3-8}$ cycloalkyl-substituted ($C_{1-6}$ alkylthio) group, (xix) a heterocycloalkyl group, (xx) heterocycloalkyl-O—, (xxi) heterocycloalkyl-S—, (xxii) a heterocycloalkyl($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group or (xxvii) an aromatic cyclic amino($C_{1-6}$ alkoxy) group, (xxviii) an aromatic cyclic amino($C_{1-6}$ alkylthio) group, U represents —O—, —S— or a single bond and with the proviso that at least one of V and W is not a single bond, when U is —O— or —S—;

V represents a $C_{1-6}$ alkylene group which may have a hydroxy group, a $C_{2-6}$ alkenylene group or a single bond;

W represents —CO—, —SO$_2$—, —C(=NH)— or a single bond;

Z represents a hydrogen atom, a $C_{2-7}$ alkoxycarbonyl group, a $C_{6-10}$ aryl-substituted ($C_{2-7}$ alkoxycarbonyl) group, a formyl group, —$R^A$, —COR$^B$, —SO$_2$R$^B$, —CON($R^C$)$R^D$, —CSN($R^C$)$R^D$, —SO$_2$NHR$^A$ or —C(=NR$^E$)N($R^F$)$R^G$;

$R^5$, $R^A$, $R^C$ and $R^D$ independently represent a hydrogen atom, a $C_{1-6}$ alkyl group which may have 1 to 5 substituents selected from the following substituent group β or any of the following substitutes (xxix) to (xxxii) which may have 1 to 3 substituents selected from the following substituent group α;

(xxix) a $C_{6-10}$ aryl group, (xxx) a heteroaryl group, (xxxi) a $C_{3-8}$ cycloalkyl group or (xxxii) a heterocycloalkyl group or both of Z and $R^5$ bind together with the neighboring nitrogen atom to form an aliphatic cyclic amino group which may have 1 to 3 substituents selected from the following substituent group α;

or both of $R^C$ and $R^D$ bind together with the neighboring nitrogen atom to form an aliphatic cyclic amino group which may have 1 to 3 substituents selected from the following substituent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have 1 to 5 substituents selected from the following substituent group β or any of the following substitutents (xxxiii) to (xxxvi) which may have 1 to 3 substituents selected from the following substituent group α;

(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl-substituted ($C_{2-7}$ alkoxycarbonyl) group, a nitro group, a $C_{1-6}$ alkylsulfonyl group, a sulfamoyl group, a carbamimidoyl group or a $C_{1-6}$ alkyl group which may have 1 to 5 substituents selected from the following substituent group β;

or both of $R^E$ and $R^F$ bind together to form an ethylene group;

or both of $R^F$ and $R^G$ bind together with the neighboring nitrogen atom to form an aliphatic cyclic amino group which may have a substituent selected from the following substituent group α;

Y represents —O—, —S—, or —NH— which may be substituted by a $C_{1-6}$ alkyl group or a halo($C_{1-6}$ alkyl) group;

Q represents —$C_{1-6}$ alkylene-, —$C_{2-6}$ alkenylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene- or —$C_{1-6}$ alkylene-S—$C_{1-6}$ alkylene-;

ring A represents a $C_{6-10}$ aryl group or a heteroaryl group;

G represents a group represented by the formula:

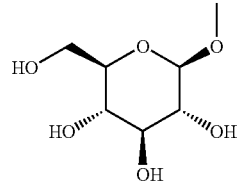

(G1)

or the formula:

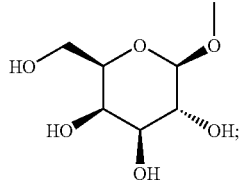

(G2)

[substituent group α]

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl-substituted ($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino-substituted ($C_{1-6}$ alkyl) group, a carboxy group, a $C_{2-7}$ alkoxycarbonyl group, a sulfamoyl group and —CON($R^H$)$R^I$

[substituent group β]

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$ alkylthio) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy ($C_{1-6}$ alkyl)]-sulfamide group, a $C_{2-6}$ acylamino group, an amino($C_{2-6}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, —CON($R^H$)$R^I$, and any of the following substitutes (xxxvii) to (xxxxviii) which may have 1 to 3 substituents selected from the above substituent group α on the ring;

(xxxvii) a $C_{6-10}$ aryl group, (xxxviii) $C_{6-10}$ aryl-O—, (xxxix) a $C_{6-10}$ aryl-substituted ($C_{1-6}$ alkoxy) group, (xxxx) a $C_{6-10}$ aryl-substituted ($C_{1-6}$ alkylthio) group, (xxxxi) a heteroaryl group, (xxxxii) heteroaryl-O—, (xxxxiii) a $C_{3-8}$ cycloalkyl group, (xxxxiv) $C_{3-8}$ cycloalkyl-O—, (xxxxv) a heterocycloalkyl group, (xxxxvi) heterocycloalkyl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have 1 to 3 substituents selected from the following substituent group γ;

or both of $R^H$ and $R^I$ bind together with the neighboring nitrogen atom to form an aliphatic cyclic amino group which may have 1 to 3 substituents selected from the following substituent group δ;

[substituent group γ]

a halogen atom, a hydroxy group, an amino group, a $C_{1-6}$ alkoxy group, a halo($C_{1-6}$ alkoxy) group, a hydroxy($C_{1-6}$ alkoxy) group, an amino($C_{1-6}$ alkoxy) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl) sulfamide group, a mono or di[hydroxy($C_{1-6}$ alkyl)]sulfamide group, a $C_{2-6}$ acylamino group, an amino($C_{2-6}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group and —CON($R^J$)$R^K$

[substituent group δ]

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl-substituted ($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino-substituted ($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di($C_{1-6}$ alkyl)amino group, a $C_{2-7}$ alkoxycarbonyl group or a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl) amino group, a $C_{1-6}$ alkyl group, a hydroxy($C_{1-6}$ alkyl) group, a $C_{2-7}$ alkoxycarbonyl group, a $C_{2-7}$ alkoxycarbonyl-substituted ($C_{1-6}$ alkyl) group or a carbamoyl group, or a pharmaceutically acceptable salt thereof, or a prodrug thereof.

2. A frised heterocyclic derivative as claimed in claim 1, wherein $R^2$ represents a hydrogen atom; Y represents —O—, —S— or —NH—; Q represents an ethylene group, or a pharmaceutically acceptable salt thereof, or a prodrug thereof.

3. A fused heterocyclic derivative as claimed in claim 1, wherein the ring A represents a group derived from a benzene ring, a pyridine ring, a pyrimidine ring, a pyrazine ring or a pyridazine ring, or a pharmaceutically acceptable salt thereof, or a prodrug thereof.

4. A fused heterocyclic derivative as claimed in claim 3, wherein the ring A represents a phenyl group, or a pharmaceutically acceptable salt thereof, or a prodrug thereof.

5. A fused heterocyclic derivative as claimed in claim 3, wherein the ring A represents a pyridyl group, or a pharmaceutically acceptable salt thereof, or a prodrug thereof.

6. A pharmaceutical composition comprising as an active ingredient a fused heterocyclic derivative as claimed in claim 1, or a pharmaceutically acceptable salt thereof, or a prodrug thereof.

7. A pharmaceutical composition as claimed in claim 6, wherein the dosage form is sustained release formulation.

8. A method for the inhibition of postprandial hyperglycemia, which comprises administering to a patient in need thereof an effective amount of a fused heterocyclic derivative as claimed in claim 1, or a pharmaceutically acceptable salt thereof, or a prodrug thereof.

9. A method for the treatment of a disease associated with hyperglycemia, which comprises administering to a patient in need thereof an effective amount of a fused heterocyclic derivative as claimed in claim 1, or a pharmaceutically acceptable salt thereof, or a prodrug thereof.

10. A method for the treatment as claimed in claim 9, wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout.

11. A method for the inhibition of advancing impaired glucose tolerance into diabetes in a subject, which comprises administering to a patient in need thereof an effective amount of a fused heterocyclic derivative as claimed in claim 1, or a pharmaceutically acceptable salt thereof, or a prodrug thereof.

12. A pharmaceutical composition as claimed in claim 6 which comprises combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1 B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an anti-platelets agent, a uric acid synthesis inhibitor, a uricosuric agent and a urinary alkalinizer.

13. A method as claimed in claim 8 which comprises administering the fused heterocyclic derivative as claimed in claim 1 in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an anti-platelets agent, a uric acid synthesis inhibitor, a uricosuric agent and a urinary alkalinizer.

14. A fused heterocyclic derivative as claimed in claim 2, wherein the ring A represents a group derived from a benzene ring, a pyridine ring, a pyrimidine ring, a pyrazine ring or a pyridazine ring, or a pharmaceutically acceptable salt thereof, or a prodrug thereof.

15. A fused heterocyclic derivative as claimed in claim 1, wherein Y is —O— or —S—.

* * * * *